US011692199B2

(12) United States Patent
Medford et al.

(10) Patent No.: US 11,692,199 B2
(45) Date of Patent: Jul. 4, 2023

(54) SYNTHETIC DESALINATION GENETIC CIRCUIT IN PLANTS

(71) Applicant: COLORADO STATE UNIVERSITY RESEARCH FOUNDATION, Fort Collins, CO (US)

(72) Inventors: June Medford, Fort Collins, CO (US); Kevin Morey, Fort Collins, CO (US); Tessema Kassaw, Fort Collins, CO (US); Mauricio Antunes, Fort Collins, CO (US)

(73) Assignee: COLORADO STATE UNIVERSITY RESEARCH FOUNDATION, Fort Collins, CO (US)

( * ) Notice: Subject to any disclaimer, the term of this patent is extended or adjusted under 35 U.S.C. 154(b) by 270 days.

(21) Appl. No.: 16/492,584

(22) PCT Filed: Mar. 23, 2018

(86) PCT No.: PCT/US2018/024053
§ 371 (c)(1),
(2) Date: Sep. 9, 2019

(87) PCT Pub. No.: WO2018/175900
PCT Pub. Date: Sep. 27, 2018

(65) Prior Publication Data
US 2020/0048650 A1 Feb. 13, 2020

Related U.S. Application Data

(60) Provisional application No. 62/475,642, filed on Mar. 23, 2017.

(51) Int. Cl.
C12N 15/82 (2006.01)
C02F 3/32 (2023.01)
C07K 14/415 (2006.01)
C02F 103/08 (2006.01)

(52) U.S. Cl.
CPC .......... C12N 15/8259 (2013.01); C02F 3/327 (2013.01); C07K 14/415 (2013.01); C02F 2103/08 (2013.01)

(58) Field of Classification Search
None
See application file for complete search history.

(56) References Cited

U.S. PATENT DOCUMENTS 6,416,985 B1 7/2002 Loescher et al.
2003/0227724 A1 12/2003 Li et al.

FOREIGN PATENT DOCUMENTS

CN 103224294 7/2013
CN 103224294 A * 7/2013

OTHER PUBLICATIONS

Doerks et al., (TIG, 14:248-250, 1998).*
Smith et al. (Nature Biotechnology, 15:1222-1223, 1997).*
Bork et al. (TIG, 12:425-427, 1996).*
Wang et al. (Cell Research, 16:277-286, 2006).*
Kosma et al. (Plant J., 80:216-229, 2014).*
Kamiya et al. (PNAS, 112:10533-10538, 2015).*
Chen, et al., "Casparian Strip Development and its Potential Function in Salt Tolerance," Plant Signaling & Behavior, 2011, 1499-1502, 6(10).
Drapek, et al., "Minimum Requirements for Changing And Maintaining Endodermis Cell Identity in the Arabidopsis Root," Nature Plants, 2018, 586-595, 4(8).
Gaedeke, et al., "The Arabidopsis Thaliana ABC Transporter AtMRP5 Controls Root Development and Stomata Movement," EMBO Journal, 2001, 1875-1887, 20(8).
Fodor-Dunai, et al., "The phosphomimetic mutation of an evolutionarily conserved serine residue affects the signaling properties of Rho of plants (ROPs)," The Plant Journal, 2011, 669-679, (66).
Gou, et al., "The MYB107 Transcription Factor Positively Regulates Suberin Biosynthesis," Plant Physiol., 2017, 1045-1058, 173(2).
Hoang, et al., "Phosphorylation by AtMPK6 is Required for the Biological Function of AtMYB41 in Arabidopsis," Biochem Biophys Res Commun., 2012, 181-186, 422(1).
International Search Report and Written Opinion regarding PCT Application No. PCT/US2018/24053, dated Sep. 18, 2019, 10 pages.
Jeong and Jung, "Rice Tissue-Specific Promoters and Condition-Dependent Promoters for Effective Translational Application," J Integr Plant Biol, 2015, 913-924, 57(11).
Juchaux-Cachau, et al., "Characterization of AgMaT2, a Plasma Membrane Mannitol Transporter from Celery, Expressed in Phloem Cells, Including Phloem Parenchyma Cells," Plant Physiol., 2007, 62-74, 145(1).
Jyohti-Prakash, "Molecular and Physiological Studies of Salt Tolerance in the Salt Secretor Mangrove Avicennia Officinalis," Ph.D. Dissertation National University of Singapore, 2015, 1-218 [online]. [Retrieved on Aug. 18, 2018]. Retrieved from the internet: URL: https://scholarbank.nus.edu.sg/bitstream/10635/120082/1/Pavithra%20A%20J.pdf>.
Kamiya, et al., "The MYB36 Transcription Factor Orchestrates Casparian Strip Formation," Proc Natl Acad USA, 2015, 10533-10538, 112(33).
Kamiya, et al., Supporting Information for "The MYB36 Transcription Factor Orchestrates Casparian Strip Formation," Proc Natl Acad USA, 2015, 1-9.
Kosma, et al., "AtMYB41 Activates Ectopic Suberin Synthesis and Assembly in Multiple Plant Species and Cell Types," The Plant Journal, 2014, 216-229, 80(2).

(Continued)

Primary Examiner — Vinod Kumar
(74) Attorney, Agent, or Firm — Dentons US LLP

(57) ABSTRACT

The present disclosure provides compositions and methods for generating plants that can grow in saline conditions, or remove a salt or other impurity from water, for example plants that can remove sodium chloride from salt or sea water, and plants that can produce purified water from salt or sea water.

6 Claims, 9 Drawing Sheets

Specification includes a Sequence Listing.

(56) References Cited

OTHER PUBLICATIONS

Lashbrooke, et al., "MYB107 and MYB9 Homologs Regulate Suberin Deposition in Angiosperms," The Plant Cell, 2016, 2097-2116, 28(9).

Leger, et al., "Conversion of Serine to Aspartate Imitates Phosphorylation-Induced Changes in the Structure and Function of Microtubule-Associated Protein Tau," Journal of Biological Chemistry, 1997, 8441-8446, 272(13).

Li, et al., "Construction of a Functional Casparian Strip in Non-endodermal Lineages Is Orchestrated by Two Parallel Signaling Systems in *Arabidopsis Thaliana*," Current Biology, 2018, 2777-2786, 28(17).

Li, et al., "Spatial Expression and Functional Analysis of Casparian Strip Regulatory Genes in Endodermis Reveals the Conserved Mechanism in Tomato," Frontiers in Plant Science, 2018, 832.

Liberman, et al., "MYB36 Regulates the Transition from Proliferation to Differentiation in the *Arabidopsis* Root," Proc Natl Acad Sci USA, 2015, 12099-12104, 112(39).

Meyer and Peterson, "Casparian Bands Occur in the Periderm of Pelargonium Hortorum Stem and Root," Annals of Botany, 2011, 591-598, 107(4).

Parida and Jha, "Salt Tolerant Mechanisms in Mangroves: a Review," Trees-Structure and Function, 2010, 199-217, 24(2).

Schreiber, "Transport Barriers Made of Cutin, Suberin and Associated Waxes," Trends in Plant Science, 2010, 546-553, 15(10).

Vishwanath, et al., "Suberin; Biosynthesis, Regulation, and Polymer Assembly of a Protective Extracellular Barrier," Plant Cell Reports, 2015, 573-586, 34(4).

Wang, et al., "The Thellungiella Salsuginea Tonoplast Aquaporin TsTIP1;2 Functions in Protection Against Multiple Abiotic Stresses," Plant & Cell Physiology, 2014, 148-161, 55(1).

Yaneff, et al., "Heteromerization of PIP Aquaporins Affects Their Intrinsic Permeability," Proc Natl Acad Sci USA, 2014, 231-236, 111(1).

Ruzicka, et al., "*Arabidopsis* PIS1 encodes the ABCG37 transporter of auxinic compounds including the auxin precursor indole-3-butyric acid," Proc Natl Acad USA, 2010, 10747-10753, 107(23).

Zhifang, et al., "Expression of a celery mannose 6-phosphate reductase in *Arabidopsis thaliana* enhances salt tolerance and induces biosynthesis of both mannitol and a glucosyl-mannitol dimer," Plant, Cell and Environment, 2003, 275-283, (26).

* cited by examiner

```
                        SEQUENCE LISTING

<160> NUMBER OF SEQ ID NOS: 46

<210> SEQ ID NO 1
<211> LENGTH: 870
<212> TYPE: DNA
<213> ORGANISM: Avicennia officinalis

<400> SEQUENCE: 1
atggcggagg gtaaagaaga agatgttaga cttggtgcca acaagttcac agaaggccag        60
cctctgggaa ctaccgcaca aacagataag gattataaag aggaacctcc cgctcccctc       120
tttgagcctg gagagcttaa atcctggtca ttttacagag ctggaattgc cgagtttatg       180
gctacttttc ttttcctata tatctccatt ctcacagtga tggggggttgg gagatccacc      240 tctaagtgcg cttccgtggg tattcaaggt attgcttggg catttggtgg gatgatcttc       300
gttttagtgt actgtacggc tggaatctct ggggtcaca ttaacccggc tgtaacattc        360
ggcttattct tggctagaaa gctaagcctt acccgagctc ttttctacat ggtgatgcaa       420
tgtctgggag ccatctgcgg agctggtgtt gttaaagggt ttatggaagg accatatcag       480
cgtcttaagg gaggtgccaa tatggtatct cacggttata caaaagggga tgggttaggc       540
gcagaaattg ttgggacatt tgttttagtc tatacagtct tctctgcaac ggatgcaaag       600
agaaacgcta gggactccca cgttccgatc ttagctcctc tccctattgg atttgcagtg       660
tttctagtgc atcttgctac aatccctgtt acaggaacag ggatcaaccc cgctagaagc       720
ttaggagcgg caataatcta caataaagat caggcgtggg atgaccattg gatattctgg       780 gttggaccctt ttattggagc tgctttagca gcagtgtacc accaattgat cattagagct      840
ataccattta aaagtaatcg agcatgctga                                        870

<210> SEQ ID NO 2
<211> LENGTH: 867
<212> TYPE: DNA
<213> ORGANISM: Aegiceras corniculatum
```

<400> SEQUENCE: 2

```
atggagggaa aggaggagga tgtaagactc ggagctaaca aatttgctga gcgacaacct      60
attggtactg ccgctcaggg ggctggagat aaagattaca aagagccgcc ggcagcacca     120
cttttttgagc cgggagaatt aagttcttgg tccttctacc gagctggcat cgctgaattt    180
atggcgacgt ttttattcct ctatatcaca gttttaacag taatgggggt ctcccgttca     240
ggctcaaaat gtgcatccgt tgggattcaa gggatagctt gggctttcgg ggaatgatt     300
ttcgctctgg tttattgcac agcgggaatt tctgggggcc acattaaccc ggcggtgaca     360
tttggacttc tcctggctcg taaacttagc cttacccgag ctgttttta catgatcatg     420
caatgtttgg gagctatttg cggcgctggt gtcgtaaagg gttttgaagg atcaagtagg     480
tttacaatcg ctggaggcgg tgctaacgtc gtgcaacccg gacatacaaa aggtgatgga     540
ctcggtgcag aaattgttgg aactttcgtt cttgtttata cagtattctc agcaacagac     600
gctaagagga acgcaaggga ttcacacgtt ccaattttag caccactgcc aattggattt     660
gcagtgttcc ttgtacactt ggctaccatc cccatcacag ggaccggtat taatcctgca     720
aggtctttgg gtgccgctat tatatacaat aaggaccagg cctgggacga acattggatc     780
ttctgggtcg gaccattcat tggagcggcc ttagctgccc tctatcatca agttgtcatt     840
agagccatcc cattcaaatc aaaatga                                         867
```

<210> SEQ ID NO 3
<211> LENGTH: 843
<212> TYPE: DNA
<213> ORGANISM: Bruguiera gymnorhiza

<400> SEQUENCE: 3

```
atggctaaag aagtctctga agagggacat gcacctcatg gtaaggacta cgtcgatccg      60
ccaccggccc ccctcataga ttgggctgaa gttaaacttt ggtcttttta tagagctgtg     120
attgccgagt ttatagctac ccttctgttc ctttatgtta caattgcaac agttattggt     180
cacaaaaagc aaactgggcc ttgtgatgga gtaggattgc tcggtattgc ctggcatttt     240
ggtggtatga tcttcatttt ggtttactgt accgcaggta ttagtggtgg acatatcaac     300
cccgcagtga cctttggtct tttttttggca aggaaagtct ccttgatcag agccttagct     360
tacatggtag ctcaatgcct cggagcaata tgtggagtgg actcgtcaa agcttttatg       420
aagcacagct acaattcact gggaggtggt gcaaactttg taaatgcagg atacaataaa     480
ggtacggccc taggagcaga aataattgga actttcgtct tggtttatac tgttttttagt    540
gcgactgatc caaagaggtc tgcaagagat agtcatgtcc ctgtccttgc acctttacct    600
atcggatttg cagttttcat ggtccatctt gccacgatcc caattactgg cacaggaatc     660
aacccggcga ggtcattcgg agctgcagtt atccacaaca atgataaaat tgggatgac      720
caatggattt tttgggttgg tccttttgtt ggagctttag cagcagccgc ttaccatcaa     780
tatatactac gagctgctgc cattaaagct ctagggagtt tccgtagtaa tagatcgaat    840
tga                                                                   843
```

<210> SEQ ID NO 4
<211> LENGTH: 855
<212> TYPE: DNA
<213> ORGANISM: Aegiceras corniculatum

<400> SEQUENCE: 4

```
atggcgaagg atattgaggt tggacctggc gctaacgctc caaaggatta ccaagaccca      60
```

-continued

| | |
|---|---|
| ccgccagctc cacttattga tgctgaagaa ttgactaagt ggtctcttta tagagccgtt | 120 |
| attgcagaat tcattgctac tctactttt ctgtacatta cagttcttac tgtgatcgga | 180 |
| tattcctctc agaccgatcc tgataagaac ccgatgatt gtggaggagt tggaattctt | 240 |
| ggtattgcgt gggccttcgg tggaatgata tttgtcctgg tatattgtac agctggaatc | 300 |
| agcggtggac atataaatcc tgccgttact cttggactt ttttagccca gaaagtttct | 360 |
| cttgtgcgag ctatgttata tatgatggct cagtgtttgg gtgctatctg cggatgtgga | 420 |
| ctagttaagg cttttcagaa atcttattat actaagtacg gcgggggagc taactatctg | 480 |
| catgacggtt acaataaagg cactggactt ggcgctgaga taataggcac ttttgtactc | 540 |
| gtatataccg tgtttagtgc taccgatcct aagcgttctg ctcgagacag ccatgttccc | 600 |
| gttttagcac cattgcctat tggtttcgcg gtgttcatgg tacatctcgc tactatacca | 660 |
| attacaggta caggaataaa ccctgctagg tcacttggag ccgctgtcat ttatggtaaa | 720 |
| aaaaagacgt gggatgatca gtggatattc tggggtggtc catttatagg tgcgcctatt | 780 |
| gctgctttct atcaccaatt cattcttcgt gctggtgcca tcaaagctct tggctcttac | 840 |
| cgatcaaacg cctga | 855 |

<210> SEQ ID NO 5
<211> LENGTH: 849
<212> TYPE: DNA
<213> ORGANISM: Avicennia officinalis

<400> SEQUENCE: 5

| | |
|---|---|
| atgacaaaag agctcagcga ggaaccaccg gtctaccagc aacgagatta tgttgaccca | 60 |
| cctccggcac cactttttaga taaggagaa ctaatgtctt ggtcgtttta cagagcactc | 120 |
| attgcagagt ttatagctac gcttctgttc ttgtatgtca gtattgctac cgtgatcggc | 180 |
| cataaaaagc tatccagcgt tgatcaatgc gatggtgtgg gtatattggg gatcgcgtgg | 240 |
| gcattcggag gaatgatttt tatactggtt tattgtactg ccggtattag cggcggtcac | 300 |
| atcaaccctg ccgttacact cgggttgttc ttggcaagga agtctctttt aataagagca | 360 |
| gtggcgtata tggttgccca atgtttggga gcaaatatgtg gagttggatt ggtcaaagca | 420 |
| ttcatgaaaa gttttttataa cggctttgat ggaggtgtta acatggttgc gtccggatac | 480 |
| aacaagggaa cagcacttgg cgccgaaatt attgggactt tgtttttggt ttacacagtt | 540 |
| tttagcgcta ctgatccgaa aagatcagca agagattctc atgttccggt tttagctcca | 600 |
| cttccgattg gattcgccgg attcatggtt catctcgcta ctatcccaat aacaggtact | 660 |
| ggaattaacc ccgcgaggag cttcggtgcc gcagtcatct ataataacga taaggcctgg | 720 |
| gacgatcatt ggattttctg ggttggacct tttgccggag ccttagcagc ggcaatttat | 780 |
| catcaatatg tccttcgtgc tgcagctata aaagcccttg cagcttccg ttcaaatcca | 840 |
| actaactga | 849 |

<210> SEQ ID NO 6
<211> LENGTH: 762
<212> TYPE: DNA
<213> ORGANISM: Thellungiella salsuginea

<400> SEQUENCE: 6

| | |
|---|---|
| atgccaatac gtaatatcgc aataggaggt gttcaagagg aagtcactca cccatcagct | 60 |
| ttacgtgcag cactcgctga gttcatctct acgctgattt tgttttttgc aggtagtggt | 120 |

| | |
|---|---|
| agtggtatcg cgttcaacaa gctcacggat aatggagcta caaccccatc cgggttggtc | 180 |
| gcagctgctc ttgctcatgc tttcggtctg tttgttgctg tatctgttgg agcaaacatc | 240 |
| tctggaggac acgttaatcc tgctgtaaca ttcggtgctt ttctcggtgg caacataaca | 300 |
| ctcctgaggg gaattcttta ctggatcgcc cagctcctgg gtagcgtggt cgcctgcttc | 360 |
| cttttaactt ttgccaccgg cggactcgcg gtgcctgctt tgggctctc tgcagggagtt | 420 |
| ggctctttga cgccttcgt ctttgagatt gttatgacat cgggctcgt gtataccgta | 480 |
| tatgcaaccg ctattgatcc aaaaaatggt tcacttggta ctatagcacc gatagctata | 540 |
| ggatttattg ttggtgctaa cattttagct gggggtgcct tctcaggtgc ttcaatgaac | 600 |
| ccagctgttg catttggtcc tgcagttgtt agttggagct ggagcaatca ctgggtctac | 660 |
| tgggcaggtc cactggtggg tggaggtcta gctggactta tttacgagtt tgtttttatt | 720 |
| ggtggaaatg ctcacgaaca gcttcctaca acagactact aa | 762 |

<210> SEQ ID NO 7
<211> LENGTH: 639
<212> TYPE: DNA
<213> ORGANISM: Bruguiera gymnorhiza

<400> SEQUENCE: 7

| | |
|---|---|
| atggcattca acaaattgac tgataatggt tcaactacgc cggcaggatt ggtagctgcg | 60 |
| agcctcgcac acgctcttgc actgtttgtc gcagtttcag tcggagcaaa catctctggg | 120 |
| ggtcatgtta accctgctgt gacatttggt gcttttgtag gtggtcatat aacgctcatc | 180 |
| cgttctcttc tttactgggt tgctcaactc cttggatctg tggttgcctg tttactctta | 240 |
| agactcgcaa ccgcagggct tgagacatct gcttttcac tttctagtgg cgttggtgcc | 300 |
| ggaaacgctt tggttttcga aattgttatg acattcggtc tagtttacac tgtatatgca | 360 |
| acagctctag accccaagaa aggaaatata ggtattattg cccctatagc tataggtttc | 420 |
| atagttggtg ccaacatttt ggctggcggc gcttttgacg tgcatcgat gaacccagct | 480 |
| gtttctttg gccggctgt tgtctcttgg acatgggaca accattgggt ctattgggtc | 540 |
| ggtccatttg tgggagcagc tatcgctgct gtagtctacg aagtttctt tattaatccg | 600 |
| tctacgcatg aacagctccc tatatcagcg gattactga | 639 |

<210> SEQ ID NO 8
<211> LENGTH: 759
<212> TYPE: DNA
<213> ORGANISM: Kandelia candel

<400> SEQUENCE: 8

| | |
|---|---|
| atgccgataa ggcagatagc tgtcggacat cctcatgaag cgacaaggcc cgatgttctc | 60 |
| aaggctgctc tggctgagtt catttctacc ttgatatttg tatttgctgg ggaaggaagc | 120 |
| ggtatggcat ttaacaagct taccgataac gggtctacta cacccgcagg acttattgct | 180 |
| gcttctatag ctcatgcgtt tggtttattc gttggtgtga gcgtatcagc taacatttct | 240 |
| ggaggccacg taaatcctgc tgtgaccttt ggagccttca taggaggcaa tataacgctt | 300 |
| ttacgaggta ttctgtactg gatcggtcaa ctattgggaa gtacagtagc atgtttgctt | 360 |
| cttaagtttt ctactggagg tcttaccacg agcgccttca gcctttcctc gggagtttca | 420 |
| gtatggaatg catttgtttt cgaaatcgtt atgactttg gtcttgtgta tacggtctat | 480 |
| gcaacagcta ttgatcctaa gaaggtaat ctcgggacaa tcgctccttc cccttctgtt | 540 |
| agtctctggg ttccctctgt gtggaccgga ggtgcattcg atggggcttc aatgaatccg | 600 |

| | |
|---|---:|
| gcggtctctt tcggacctgc attggtgagt tggacatggg agaaccattg ggtgtattgg | 660 |
| gctggaccct tgattgggag cgctatcgct gctctgattt cgactctttt tttcatcggt | 720 |
| tacggcaccc atgaacaact tcctaccgcg gattactga | 759 |

<210> SEQ ID NO 9
<211> LENGTH: 757
<212> TYPE: DNA
<213> ORGANISM: Thellungiella salsuginea

<400> SEQUENCE: 9

| | |
|---|---:|
| atgcctatac gtaacatcgc ggtgggaaga cctgaggagg caactaagcc tgacgcacta | 60 |
| aaagcagctc tcgcggagtt catctcaaca atgatttcg tctttgctgg ttcaggtagt | 120 |
| ggcatggcat tcaataaact gactgaaaat ggtgcaacga caccttcagg tctagttgcg | 180 |
| gctgcgctag cccacgcttt tggtctgttt gtggctgtat ccgttggagc taacatctca | 240 |
| ggcggacacg ttaatcctgc cgtcactttt ggagcatttg taggtggtaa catcacttta | 300 |
| ctacgtggaa tattgtattg gatcgcccag cttgcaggat cagttgttgc ttgccttctc | 360 |
| ctcaagttcg ctactggagg gcttgttgtg cctgctttcg gtctatcagc gggagttggc | 420 |
| gtgttgaacg cgtttgtgtt tgaaatagtt atgacattcg gcttggtata caccgtgtat | 480 |
| gctacagcca ttgaccctaa gaatggatca cttggcacca ttgctcctat tgctattggg | 540 |
| tttattgttg gagctaatat actcgctgga ggagcattct caggtgcaag tatgaacccg | 600 |
| gcagttgctt tcggaccagc agttgtgtca tggtcttggt cgaaccactg ggtgtactgg | 660 |
| gcaggtccct tggtcggcgg gggaattgca ggtctcatct atgaagtgtt ctttatcaac | 720 |
| acaacacatg agcaattacc tacaaccgac tatttag | 757 |

<210> SEQ ID NO 10
<211> LENGTH: 1002
<212> TYPE: DNA
<213> ORGANISM: Arabidopsis thaliana

<400> SEQUENCE: 10

| | |
|---|---:|
| atgggaagag caccatgctg cgacaaggca aacgtgaaga aaggaccttg gtccccggaa | 60 |
| gaagatgtga agctcaagga ttacatcgac aaatatggca ctggtggcaa ctggatcgca | 120 |
| ctgcctcaga aaattgggct gaagagatgt ggtaagagtt gcagactgag atggcttaat | 180 |
| tacttaagac caaacatcaa acatggtggt ttttctgagg aagaagatag aatcatcttg | 240 |
| agtctctaca ttagcattgg aagccggtgg tccataattg cagctcagct tcctggaagg | 300 |
| actgacaatg acatcaagaa ttattggaac acaaaactga agaagaaact tctaggaaga | 360 |
| cagaaacaaa tgaatcgtca agactccata accgattcta ctgagaacaa cctcagcaac | 420 |
| aataacaaca ataagagtcc tcagaatctg agcaattcgg cactggagag gctccagctt | 480 |
| cacatgcagc ttcagaatct acagagccct ttctctagtt tctacaacaa ccctatcttg | 540 |
| tggcccaagc tgcatccatt gctccagagc actacaacta atcaaaaccc taaacttgca | 600 |
| tctcaagaga gcttccaccc tttaggagtt aacgttgatc atcagcacaa caataccaaa | 660 |
| ctagctcaga taaacaatgg agcctcttct ctctattcgg agaacgtaga gcaatcccaa | 720 |
| aaccctgctc atgaatttca acctaatttc ggtttttcac aggaccttcg attagataat | 780 |
| cataacatgg acttttatgaa cagaggggtt tctaaagaac tgtttcaagt gggcaacgag | 840 |
| tttgagctaa cgaacggttc gagttggtgg tcagaggaag tggaactaga gaggaaaacg | 900 |

| | |
|---|---|
| acatcgtcga gttcttgggg gtcagcttct gtgcttgatc agacaactga gggaatggtt | 960 |
| atgcttcaag attacgctca gatgagctac cacagtgttt ga | 1002 |

<210> SEQ ID NO 11
<211> LENGTH: 1002
<212> TYPE: DNA
<213> ORGANISM: Eutrema salsugineum

<400> SEQUENCE: 11

| | |
|---|---|
| atgggaagag ctccatgctg cgacaaggca aacgtgaaga aagggccatg gtcgccggag | 60 |
| gaagatgtga agctcaagga ttacatcgac aaatatggca ctggtggcaa ctggatcgca | 120 |
| cttcctcaga aaatcgggtt gaagagatgt ggtaagagtt gccgactgag atggcttaat | 180 |
| tacttgagac caaacatcaa acacggtggc ttctctgagg aagaagatag tatcatcttg | 240 |
| agtctttaca tcagcattgg aagccggtgg tctataattg cagctcagct tcctggaagg | 300 |
| acagacaatg atatcaagaa ctactggaac acaaaactga gaagaaact actcggaaga | 360 |
| cagaaacaaa tgaatcgtca agactccatt accaattcaa atgaaaacaa tatcagcaac | 420 |
| aacaacaaca caagagtcc tcaaaatctg agtaattcgg ctctagagag gctccagcta | 480 |
| cacatgcagc ttcagaatct tcagagccct ttctctagtt tctacaacaa ccctatcttg | 540 |
| tggcccaagc ttcacccatt gctgcagagt actacccatg atcaaaatcc taagcttgca | 600 |
| tctcaagaaa ccttccaccc ttcaggagtt aacgttaatc atcagaacaa tcatatcaag | 660 |
| ctagctgaga tcaacaatgg atcctcccct ctctattcag agaacataga gcaatcccta | 720 |
| aaccctgctc acgaatttca acctaatttc ggttttcgc aggaccttcg attagataat | 780 |
| catcataaca tggatcttat gaacagaggt gattctaaag aattgtttca agtgggaaat | 840 |
| gagtttgagc taacgaccgg ttctagttgg tggtccgagg aagtggagct agagaggaaa | 900 |
| acgacttcga cgagttcttg gggatcagct tctgttcttg atcagactac tgaaggaatg | 960 |
| gttatgcttc aagattacgc tcagatgagc taccacagtg tg | 1002 |

<210> SEQ ID NO 12
<211> LENGTH: 996
<212> TYPE: DNA
<213> ORGANISM: Brassica napus

<400> SEQUENCE: 12

| | |
|---|---|
| atgggaagag ctccatgctg cgacaaggca aacgtgaaaa aagggccatg gtcgcctgaa | 60 |
| gaagatgtga agctcaagga ctacatcgac aaatatggca ctggtggcaa ctggatcgca | 120 |
| ctgcctcaga aaattgggtt gaagagatgt ggtaagagtt gcagactgag atggcttaat | 180 |
| tacttaagac caaacatcaa acatggtggc ttttcagagg aagaagatag tatcatcttg | 240 |
| agtctttaca tcagcattgg aagccggtgg tctataattg cagctcagct tcctggaagg | 300 |
| acagacaatg atataaaaaa ttactggaac acaaaactga gaagaagct gctcggaaga | 360 |
| cagaaacaaa tgaatcgtca agactcgatt gctgattcga atgaaaacaa tatcagcagc | 420 |
| aacaacaaca agagtcctca aaatcttagt aattcggcac tagagaggct tcaacttcac | 480 |
| atgcagcttc agaatctaca aagccctttc tctagtttct ataacaaccc tatgttgtgg | 540 |
| cccaagcttc atccactact gcagagcact cctgatcaaa actctaaact tggatcccaa | 600 |
| gaaagcttcc accctctagg agttaacgtt gttcatcaga acaataatat caagctagct | 660 |
| gagatcaacg atggagtctc tcctctctat tcagagaacg tagagcaatc cctaaaccct | 720 |
| actcacggat ttcaacctaa ttctcggtttt tcgcaggatc ttcagttaga taatcataac | 780 |

| | |
|---|---|
| atggacctta tgaacagagg tggttctaaa gaattgtttc aagtgggcaa cgagtttgag | 840 |
| ctaacgaacg gttcgagttg gtggtcggag gaagtcgagt tagagaggaa aacaatatcg | 900 |
| tcgagttctt ggggatcagc ttctgttctt gatcagacga ctgacggagt ggttatgctt | 960 |
| caagattatg gtcagatgag ctaccatagt gtgtaa | 996 |

<210> SEQ ID NO 13
<211> LENGTH: 849
<212> TYPE: DNA
<213> ORGANISM: Arabidopsis thaliana

<400> SEQUENCE: 13

| | |
|---|---|
| atgggaagat caccttgttg tgataaaaat ggagtgaaga agggaccttg gactgctgag | 60 |
| gaggatcaga aactcatcga ttatattcga tttcatggtc ctggcaactg gcgtacgctc | 120 |
| cccaaaaatg ctggactcca tagatgtgga aaaagctgcc gtcttcgatg gaccaattat | 180 |
| ctaagaccgg acatcaagag aggaagattc tcgttcgagg aagaagaaac tatcattcag | 240 |
| ctacacagtg ttatgggaaa caagtggtca gcaatagccg ctcgtctacc agggaggacc | 300 |
| gataacgaaa taaaaaacca ttggaacact cacatccgca agagacttgt aaggagtggt | 360 |
| atcgaccctg ttactcattc tccacgcctt gatcttcttg atttgtcctc acttttgagt | 420 |
| gcacttttca accagccaaa cttttcagca gttgcaacac atgcgtcttc tcttcttaat | 480 |
| cctgatgtat tgaggttggc ctctctacta ctgccacttc aaaaccctaa tccagtttac | 540 |
| ccatcgaacc tcgaccaaaa tcttcaaact ccaaatacat catcagaatc gtctcaacca | 600 |
| caagctgaaa ccagtacagt cccaacaaac tatgaaactt catcattgga gcctatgaac | 660 |
| gcaagactcg acgacgttgg tcttgcagat gtattaccac ctttgtcaga gagttttgac | 720 |
| ttagactcgc tcatgtcaac gccaatgtct gatccacgac aaaatagcat tgaagcagaa | 780 |
| accaactcca gcactttctt cgactttggt attccggaag atttcatctt agatgacttt | 840 |
| atgttttga | 849 |

<210> SEQ ID NO 14
<211> LENGTH: 867
<212> TYPE: DNA
<213> ORGANISM: Brassica napus

<400> SEQUENCE: 14

| | |
|---|---|
| atgggaagat taccttgttg tgacaagaat ggagtgaaga agggaccatg gacgcctgag | 60 |
| gaggatcaga aactcatcga ttatattcga gttcatggtc cgggcaactg gcgtattctc | 120 |
| cctaaaaatg ctggactcca aggtgtggaa aaagctgcc gtcttcgatg gaccaattat | 180 |
| ctaagaccag acatcaagag aggaagattc tccttcgagg aagaagaaac tatcattcag | 240 |
| ctacacagtg ttatgggaaa caagtggtcc gcaatagcag ctcgtctacc tggaaggact | 300 |
| gacaacgaaa ttaaaaacca ttggaacact cacatccgca agcgacttgt aaggagtggc | 360 |
| atcgaccctg taactcactc cccgcgcctt gatcttcttg acttgtcctc acttctagcc | 420 |
| gcgattttca atcaaccaaa cttttcatca gttgcaacaa atgcatcgtc tctgcttaat | 480 |
| cctgatgtat tgaggttagc ttctcttctc ttgcgccctc aacaaccact tcaaaacccct | 540 |
| aatacacttt acgaatcgaa cctcgaccaa atcttcaaa ctccaaacac atcagtatcg | 600 |
| tctcaagaca ctcaaccaca agccgagtgt acagctccaa caaaggatga acttcatat | 660 |
| tttgagccta tgaacgcaag gctagaggac ggtccttcag atgtactacc acctttgtca | 720 |

```
gagagttttg acttagactc actcatgtca acgccaaatt attctccaca acaaaataac    780
attgaagcag aagccaactc cagcagttta tttgacttta ggtttccgga taattttacc    840
tttgatgact ttatggggtt gctttaa                                         867
```

<210> SEQ ID NO 15
<211> LENGTH: 867
<212> TYPE: DNA
<213> ORGANISM: Eutrema salsugineum

<400> SEQUENCE: 15

```
atgggaagat caccttgttg tgacaagaat ggagtgaaga agggaccatg gacgcctgaa     60
gaggatcaga aactcatcga ttatattcga tttcatggtc ccggtaattg gcgtattctc    120
cctaaaaatg ctggactcca aaggtgtgga aaaagctgcc gtcttcgatg gaccaattat    180
ctaagaccgg acatcaagag aggaagattc tccttcgagg aagaagaaac tatcattcaa    240
ttacacagtg tcatgggaaa caagtggtca gcaatagcag ctcgtctacc aggaagaacc    300
gataacgaaa taaaaaacca ttggaataca catatccgta agagacttat aaagagtggc    360
attgaccctg ttactcactc tccgcgcctt gatcttcttg atgtatcttc acttttagca    420
gcactattca accaaccaaa cttttcagcg gttgcagcac acgcatcatc cctgctcaat    480
cctgatgtat tgaggttggc ctctctactc ttggcccctc aacagccact tcaaaaccct    540
aatccaattt actcatcgaa cctcgaccaa tatcttcaaa ctccagtcac atcagtgtct    600
tctcaagact ctcaaccaca agctgagtgt acaatcccaa caaacaatga tcaaacttca    660
tctttcgagt ctataaacgc aaagctcaac gtcggtcctg cagatgtatt acctcctctg    720
tcagagagtt tggacttaga ctcactcatg tcgacgccga agtcttctcc acagcaaaat    780
agcactgaag cagaagccaa ctccagcagt tccttcgact tggttttcc ggataatttc    840 acctttgatg aatttatgtt aatttaa                                         867
```

<210> SEQ ID NO 16
<211> LENGTH: 1575
<212> TYPE: DNA
<213> ORGANISM: Apium graveolens

<400> SEQUENCE: 16

```
atggctggag cctttaacgt gtctggagat gatagcgggg gctcaaagga tgttggaagc     60
ccagtcatat tcgacgctgt taagaagcct aagcgtaaca agtatgcatt cggatgcgct    120
attttggcat ctatgacttc cgtgctctta gggtacgata tcggtgttat gagcggtgct    180
gctatctata ttaaggacca gctccacgtg tccgatgtta aacttgagat tgtagttggg    240
ataattaact ttttctcatt ggttggttca gctctagcag gtcgaacatc agattggatc    300
ggtagacgat atactatggt attggccggg gccatctttt tgtcggtgc gatcctaatg    360 ggatttgcaa caaattactc atttctgatg ttcggtagat tgtggcagg tatcggcgtg    420 ggttacgctc ttatgatagc gcctgtgtac acagctgagg ttagtagcgc tagctccaga    480
ggtttcctaa ctagcttccc ggaggtgttc attaatatcg gagtgctctt gggttatgtt    540
tccaattacg cgttctccaa attgcctgca aacctgggat ggagattcat gcttggtatt    600
ggagcgatcc catcaatagg attggcaatt ggtgtgctag gatgcccga gtccctaga    660 tggcttgtga tgaaaggaag attaggagag ccagacagg ttttggataa gacttctgac    720
agcaaggagg agtctaggtt gaggttgtca gatatcaaac aagcagcagg aatccctgag    780
gagtgcaacg atgatattgt cgtgatgcct aaaaggagaa acgacgaggc tgtgtggaaa    840
```

```
gaacttctat tacatcctac accttcggta cgacacgcat tcatagcagg agttggtctt      900
catttttttc aacaatcgtc tggtattgat gcaggtggcc tctactcgcc cagaatcttc      960
gagaaagctg gtatcacttc cacggatttg aagttgcttg ctacaattgc cgtgggcatt     1020
tcaaagacgc tgtttatcct cgtcgccaca tttctcctag acagaatcgg tcgtagaccc     1080
ctattgttga catcgatggg aggtatgatt atctccctca cattactggg cacatcactt     1140
gctgttatag accattcaga ccacactgtc cattgggctg tggcattggc tattttggga     1200
gtgctggctt acgtcggaac tttctcgatc ggcctcggac ctatagcgtg gggatacagt     1260
tcagaagttt ttccgctccg attgcgtgct cagggctgta gtatcggtgt cgcagttaat     1320
cgaggaacgt ccggaataat ttctatgaca ttcctctcac tctacaaagc aatctcaatc     1380
gctgcgcttt tttatctatt tgccgcaatt gcgggagtag cttggatttt catttttacc     1440
ttgctccctg agacacaagg tcgttctctc gaagaaatgg gtttgttgtt cggaacgtac     1500
tttggttgga gaaaaactct caaggggcta aagaaccgag aggcggaaga ggctaaaaat     1560
gctaacgtta tctga                                                      1575
```

<210> SEQ ID NO 17
<211> LENGTH: 1443
<212> TYPE: DNA
<213> ORGANISM: Olea europaea

<400> SEQUENCE: 17

```
atgacttccg ttttgcttgg ttatgatatt ggagtgatga gtggagcagc aatttacata      60
aaagatcagc tccatgtgtc ggacgtcaaa ctggagattg ttgtcggaat aattaacttc     120
ttttcacttg ttgggtctgc tcttgccgga agaacctccg actggattgg caggcgttac     180
acaatggtgc tagccggtgc tatatttttt gttggagcaa tacttatggg atttgcaacc     240
aactattcat ttctgatgtt tggtcgattc gtcgccggaa tcggagtagg ttatgccctc     300
atgattgctc cggtgtacac ggccgaggtt tctccagcat catctcgtgg atttcttact     360
tcattcccgg aagttttcat taatatcggt gtactgctcg gatatgtctc gaattatgca     420
ttttccaaac tccctgccaa cttgggctgg cgattcatgc ttggaatcgg agcaatacct     480
tcaatcggtt tagcgattgg tgtcctaggc atgcccgaat cacctcgttg gctcgtcatg     540
aaaggccgtc tcggcgaagc tagacaagtc ctagacaaaa cctcagattc caaagaagaa     600
tctcgcctta gattatccga catcaaacag gctgctggca tacccgaaga atgcaacgac     660
gatatcgttg taatgcctaa acggaggaat gacgaggcag tgtggaaaga gttgcttctc     720
catcctacac catcagtccg tcacgcgttc attgctggcg ttggtctaca ttttttccaa     780
caatcaagtg gcatagacgc tgttgttttg tacagtcctc gaattttcga aaaggctgga     840
atcacgagta ccgacttaaa actgctagca acaatagctg ttggaatctc gaagacactc     900
ttcatcctag tagctacatt tttactcgat cgaatcggac gacgtccatt gcttctcaca     960
agcatgggag gaatgatcat atccttaact ctcctgggaa catccttggc tgttattggc    1020
cactcagatc acacagttca ttgggccgtg gcattggcaa tcttcggagt tttagcatac    1080
gtgggcacgt tttctattgg gctaggtcca attgcatggg tttatagttc agaggtgttc    1140
ccattaagac taagggccca aggatgtagc attggagtag ctgttaacag gggtacaagt    1200
ggaattatct cgatgacatt tttgtcgcta tacaaagcca taagtatagc aggggcattc    1260
tatttatttg cagctattgc aggagtggca tggatattta tattcacatt acttcctgaa    1320
```

| | | |
|---|---|---|
| acacaaggga ggagccttga agaaatgggg ttactgtttg aacctatttt ggttggaga | 1380 | |
| aaaactttga agggtttgaa gaacagagaa gctgaggaag ctaaaaatgc taatgtcata | 1440 | |
| tag | 1443 | |

<210> SEQ ID NO 18
<211> LENGTH: 1584
<212> TYPE: DNA
<213> ORGANISM: Daucus carota

<400> SEQUENCE: 18

| | | |
|---|---|---|
| atggccggag ctttcagcgt ttccggtgac gattccggca acccgaaaaa tgttgcttcc | 60 | |
| cctgtcatat ttgatgctgt gaagaaacct aagagaaaca agtatgcttt tggctgtgcc | 120 | |
| attttagctt ccatgacttc cgtcttactt ggatacgata ttggagtgat gagtggagca | 180 | |
| gccatctaca taaaaaaaga actcgatgtc tccgaagtga agctcgaaat tctcgtcgga | 240 | |
| ataatcaacc tctactctct cgtgggctcc ggtttcgccg aagaacctc cgactggatc | 300 | |
| ggcaggcgtt acactatggt cttagccggt gccatatttt tgcgggagc cttactcatg | 360 | |
| ggattcgcca caactatgc atttctcatg ttcggtcgat tgtcgccgg acttggagta | 420 | |
| gggtatgccc tcatgattgc tccggtgtac acggcggagg tttctccggc ctcgtcgcgg | 480 | |
| ggatttctca cgtcgttccc ggaagtttc attaatttcg gtgtacttct gggatacgtt | 540 | |
| tcaaacttcg gcttctccaa gctccccgaa atctcggct ggcgcttcat gctcggaatc | 600 | |
| ggagccatcc cctccatcgg cctcgccatc ggcgtcctcg gcatgccgga atcccctcgc | 660 | |
| tggctcgtca tgaaaggccg cctcggcgaa gcccgacaag tcctcgacaa aacctccgac | 720 | |
| tccaaagaag aggctcgcct ccgcttatcc gacatcaaag ccgccgccgg catccccgaa | 780 | |
| gactgcaacg acgacgtcgt cgaagtccct cgccggaaaa acgacgacgc cgtctggaaa | 840 | |
| gagctcctcc tccgcccac cgcctccgtc cgtcacgcat tcatcgccgg cgttgggctc | 900 | |
| cacttctttc aacagtccag tggcatagac gccgtcgttt tgtacagtcc ccgaatcttc | 960 | |
| gaaaaagccg ggattaaaag cgatagtatg aaattactcg cgacaatcgc ggttggattc | 1020 | |
| tcgaaaacga ttttttatttt agtcgcgact tttttgctcg ataaaatcgg gagaagaccg | 1080 | |
| ttgttgttga ccagcatggg cggaatggta atttcactaa ctctcctcgg gacttcatta | 1140 | |
| gcagttattg accattctga ccacacggtc cattgggccg taacgttagc gatcttcggg | 1200 | |
| gttttagcca atgtggcgat gttttccatt gggctgggcc cgatcgcgtg ggtctacaat | 1260 | |
| tcggaggtgt ttccgctgag gctgcgggcc caggggtgca gcattgggt cgcggtgaac | 1320 | |
| agggggtacaa gtgggattat ttcgatgacg ttttgtcct tgtacgaggc gatttcgatt | 1380 | |
| gcggggggcgt tttatttata tgcggcgatt gcggcggtgg ggtgggtgtt tgtgttcacg | 1440 | |
| ttgctgccgg agacgcaggg gcggagcctg gaggagatgg ggttattgtt tgggaattat | 1500 | |
| tttgggtgga ggacgacttt gagggatttg aagcacaaag aagctgagga ggcaaagaat | 1560 | |
| gctagtgttg tgtccagttt ataa | 1584 | |

<210> SEQ ID NO 19
<211> LENGTH: 930
<212> TYPE: DNA
<213> ORGANISM: Apium graveolens

<400> SEQUENCE: 19

| | | |
|---|---|---|
| atggctataa cattgaacag tggatttaaa atgcctgtgt taggtctcgg ggtgtggcgt | 60 | |
| atggaccgaa acgaaataaa aaacctttg ctatcggcaa ttaatctcgg gtataggcac | 120 | |

```
tttgattgtg cagcggatta taagaacgaa cttgaggtgg gagaggcttt caaagaagca    180
ttcgacactg acctcgttaa acgtgaggat ctcttcatta caacaaaact gtggaactcc    240
gatcatggtc atgtgataga agcatgtaag aactccctta agaaattgca gcttgaatac    300
cttgacctct accttattca ttttccaatg gcttctaagc actctggtat tggaaccact    360
agatcaatct tggatgatga aggagtttgg gaagtagatg cgactatatc tcttgaagct    420
acttggcatg agatggaaaa actcgttgag atggggttag ttagatctat cggaatctct    480
aattacgatg tttatctcac gcgagatatc ttgagctata gcaagatcaa gcctgccgtc    540
aatcagatag agacgcatcc ttacttccaa cgtgactcat tgattaagtt ctgccaaaag    600
tacggtattg caataactgc gcatacgcca ctgggtggag ccctagccaa cactgagaga    660
ttcggttccg ttagttgcct tgacgaccca gttctgaaga agctgtctga taaacataac    720
aagagcccag cgcaaattgt gctgagatgg ggggtacaac gaaacaccat tgtgattcct    780
aagagttcca aaaccaaaag gcttgaggaa aacataaata tctttgactt tgagttgagc    840
aaggaagata tggaactgat caaaactatg gaaagaaatc aacgtagtaa cacgcctgct    900
aaagcatggg gtatcgatgt ctacgcttga                                     930

<210> SEQ ID NO 20
<211> LENGTH: 930
<212> TYPE: DNA
<213> ORGANISM: Arabidopsis thaliana

<400> SEQUENCE: 20
atggagataa cactgaacag tggcttcaag atgccgatcg tcggcttagg agtatggaga    60
atggagaagg aagggattcg agaccttatc ctcaatgcca tcaagatcgg ctatcgccat    120
ctcgactgtg ctgctgatta taggaatgag accgaagttg gtgatgctct tacagaagca    180
ttcaagactg gtctggttaa gagggaggat ctcttcatta caaccaagct atggaattca    240
gaccatggcc atgtcattga ggcctgcaaa gacagtctca agaaacttca acttgattac    300
ctcgatctct cctcgttca ttttcccgta gcaacgaaac acaccggagt agggacaacc    360
gatagtgctt gggcgatga cggggtattg acatagaca cgaccatctc tctgaaaact    420
acatggcacg acatggaaaa gcttgtttct atgggtttag tccgcagcat tggaatcagt    480
aactatgatg tctttctaac gagagattgc ttggcttact ccaagatcaa acctgctgtg    540
aatcagatcg agacacatcc ttacttccaa cgtgattctc ttgtcaaatt ctgccagaaa    600
catggtatct gtgtcactgc tcatactcct ctcggaggtg ccacagccaa tgccgagtgg    660
tttggcaccg tgtcatgcct ggatgatcca gttctcaaag atgtggccga agtacaaa     720
gagacagtgg cacaagttgt cctgaggtgg ggaatccaga gaaaacggt ggtgatacca    780
aagacatcaa agcctgcgag attggaagag aactttcagg ttttcgactt cgaactatcg    840
aaagaggaca tggaagtgat caaaagcatg gagaggaaat accacgcgaa ccaaccagcc    900
aagttttgga acattgatct ctacgcttga                                     930

<210> SEQ ID NO 21
<211> LENGTH: 930
<212> TYPE: DNA
<213> ORGANISM: Daucus carota

<400> SEQUENCE: 21
atggcgataa ctctgaacag tggcttcaaa atgcccgttt tgggtctcgg tgtctggcgt    60
```

| | |
|---|---|
| atggaccgca aagacatcaa gaatctcctc cccaccgcca ttaagatcgg ttaccgtcac | 120 |
| ttcgactgtg ctgctgacta caagaatgag ttagaagtag gggaggcact taaagaggcg | 180 |
| ttcgatttag agcttgtcaa gagggaggat cttttatta ctaccaagct ctggaattca | 240 |
| gaccatggac atgtcattga ggcctgcaag aacagtctga agaagcttca gctagactat | 300 |
| ctcgatcttt acctcattca cttccctata gcatctaaac actctggagt tggaaccact | 360 |
| cgcagtatct tggacgagga aggtgtgttg gagattgata caaccatttc cctggaaacc | 420 |
| acatggcatg acatggaaaa gctggttgac atgggcttag tgagaagcat aggaatcagc | 480 |
| aactacgatc tttacttaac cagagactgc ttggcatatg ccaatgtcaa gcctgctgtg | 540 |
| aaccagatcg agacgcaccc ttacttccaa cgggagtctc ttgtgaaatt ctgtcagaag | 600 |
| aacggcattg ctatcacggc gcacacaccg ctcggtggtg cactggcgaa tactgagcga | 660 |
| ttcggaacta tttcgtgctt ggatgatccg actcttaaga aattaggcga caaacacaag | 720 |
| aagtcaccag ctcagattgt tctccgctgg ggtatacagc gcaacacgat tgtgatcccc | 780 |
| aagtcgtcga aaacaaaacg acttgaggaa aatatagaca ttttcgactt tgagctgagc | 840 |
| aaggaagata tggagctgat tcgaagcatg gagcgcaagt acaggactaa ttcgcctgct | 900 |
| aaagcttggg gaatcgatgt ttatgcttga | 930 |

<210> SEQ ID NO 22
<211> LENGTH: 1320
<212> TYPE: DNA
<213> ORGANISM: Arabidopsis thaliana

<400> SEQUENCE: 22

| | |
|---|---|
| atggatacga gtgaagcaag gaaccgtaaa gttgttgcag ttgaacaatt cgatctcgaa | 60 |
| gtccctgaga ctgctcatca gattagcagc gattcatggt ttcaggtagc ttttgttcta | 120 |
| acgaccggta taaacagtgc ctatgtgttg ggatattccg ggacagtcat ggttcctttg | 180 |
| ggttggattg gtggtgtggt tggactcatt cttgctaccg caatctctct ttacgcaaac | 240 |
| actcttatcg ccaaacttca tgagtttggt ggcaaaagac acattcgtta tagggatctt | 300 |
| gcaggcttca tctatggtaa aaagatgtat cgtgttacat ggggattgca atatgtcaat | 360 |
| cttttcatga ttaattgtgg cttcatcata cttgctggtt cagccttaaa ggctgtttat | 420 |
| gtacttttta gagatgatag tctcatgaaa ctgcctcact tcatcgccat cgcgggtgtt | 480 |
| gtatgcgcga ttttcgcaat cggtattcct catttatcag ctcttggaat ctggctagga | 540 |
| gtttcaacaa tcctcagcat aatctacatt attgttgcaa tagttctatc agctaaagat | 600 |
| ggagtaaaca agcctgaaag agattacaac atacaaggat catcaataaa caaactcttt | 660 |
| accataacag gagcagctgc aaatctagtt ttcgcattca acacgggaat gctcccggaa | 720 |
| atacaggcca cggtgaagca accggtcgtt aaaaacatga tgaaggctct gtattttcaa | 780 |
| ttcactgttg gtgttttacc tatgtacgcg gttacattca tcggatattg gcttacgggt | 840 |
| tcctcgacat cgacttatct cttaaacagc gtcagtggac ctgtttgggt caaagcactc | 900 |
| gctaacattt cagcttttct ccaatctgtt atctctttac atattttgc aagtccgact | 960 |
| tatgagtata tggacacaaa gtatggagtc aaaggaagtc cattggcaat gaagaatctg | 1020 |
| ttgtttagaa cagtagcaag aggaagctac attgcggtga gcactcttct ctctgcgctt | 1080 |
| ttaccgtttc tcggagattt catgagcctt accggagcga taagcacgtt ccctctcaca | 1140 |
| ttcatattag cgaatcacat gtatcttgtt gctatgaatg atgagcttag tcttgtgcaa | 1200 |
| aagctatggc attggctcaa tgtttgcttc tttggattaa tgtctcttgc tgctgctatt | 1260 |

```
gctgctgtta gactcatctc tgttgactcc aagaacttcc atgttttgc tgatgtttga    1320
```

<210> SEQ ID NO 23
<211> LENGTH: 1320
<212> TYPE: DNA
<213> ORGANISM: Brassica napus

<400> SEQUENCE: 23

```
atggatacga gtgaggctag gaaccgtaaa gtcgtctcag tggaaaagtt cgatcttgaa     60
atccctgaga ctgctcatca gatcagcagc gattcatggt tcaggtagc atttgttctg    120
acaaccggta taaacagcgc ctatgtgttg ggatattccg ggacagtcat ggttcctttg    180
ggttggattg gtggtgtggt tggtctcctt ctcgctaccg caatatccct ttacgcaaac    240
tctcttatag ccaagcttca tgagtttggt ggaaaacgac acattcgtta tagagatctc    300
gctggcttca tctacggtaa aaagatgtat cgtgttacat ggggattgca atatgtcaat    360
cttttcatga ttaattgtgg ctacatcata cttgctggtt ccgctttaaa ggcggtttat    420
gtacttttta gagatgacag tgtaatgaaa ctgcctcact ttatcgccat gcgggtgtt    480
gtatgtgcgc ttttcgcaat cggtattcct catttatcag ctcttggaat atggctagga    540
gtatcaacaa tcctcagcct gatttacatt gttgttgcaa tagttctatc agttaaagat    600
ggagtaaaca aaccttcaag agattacaac atacaaggat catcagtaga caaaatcttt    660
accataacag gagcagcagc aaatctagtt ttcgcattca acacgggtat gctcccagaa    720
atacaggcca ctgtgaagca accggtggtt aaaaacatga tgaaggctct gtatttcaa    780
ttcactgctg gtgtattacc aatgtatgcc gttacattca tcggttattg ggcttacggc    840
tcctcaacat caactatct gttaaacagt gtcagtggac tctctgggt taaagctcta    900
gctaacattt cagcctttct ccaatccgtt atctctttac acattttgc aagtccgacg    960
tatgagttta tggacacaaa gtatggaatc aaaggaagtc cattagcact gaagaatctg   1020
ttgtttagaa cagtagcgcg aggaagctac atcgcggtga gcactcttct ctcagcgctt   1080
ttaccgtttc ttggagattt catgagcctc acgggagcta taagcacttt ccctctcacg   1140
ttcatattag caaatcacat gtatgtcgta gctatgaacg ataagcttag tcctgttcaa   1200
aagctatggc attggcttaa cgtttgcttc tttgggttaa tgtctcttgc tgctgcaatt   1260
gctgctgtta gactcattgc tgttgactcc aagaacttcc atgtttttgc tgatgtctga   1320
```

<210> SEQ ID NO 24
<211> LENGTH: 792
<212> TYPE: DNA
<213> ORGANISM: Methanohalophilus portucalensis

<400> SEQUENCE: 24

```
atgaaccaat acggcaaaca agatttcggc gacaaccccta tcgaagtaag agagtctgac     60
cattacgagg aggagtatgt tttgggattc gtggataagt gggatgagct aattgactgg    120
gagtctcgag ctgagtctga gggagacacc atcatcaata tactaaaaga acgaggagtc    180
aagaaggttt tagatgtagc aacaggaacc ggtttcaatt ccgtgaggct actacaggca    240
ggatttgacg tggtcagcgc ggacggatca gccgagatgc tagtaaaggc ttttgacaac    300
gcccgtgacc acggttatct catgaggaca gttcaagcgg actggaggtg gatgaacaaa    360
gatatacatg acaagtttga tgcaatagta tgtttgggaa actccttcac tcacctgttt    420
gatgaaggag acagaagaaa agcgttggca gagttttatg ctctgctaaa gcatgacgga    480
```

```
gtgctgttat tagatcagag gaattatgat gcaattctag acgatgggta cagtagcaaa      540
cacgctcatt actattgcgg cgacactgtt tcagtttacc ccgagcatgt agatgaggga      600
ctggcgcgat ttaagtacga gttcagcgat ggctccgttt acaaccttaa catgttccct      660
cttaggaaag attacactag gcagctactg cacgaagtag ggttccagga aattaacaca      720
ttgggagatt tcaaggagac gtacaaggag gacgagcccg acttcttcct gcacgtcgcg      780
gaaaaaaatt ga                                                          792
```

```
<210> SEQ ID NO 25
<211> LENGTH: 837
<212> TYPE: DNA
<213> ORGANISM: Methanohalophilus portucalensis

<400> SEQUENCE: 25
atgagcgaga atcaaaagac tgcggtagat aaggcgcagg aatactataa ctcagacgat      60
gctgacaact tctatttcac gatctggggt ggtgaagaca tacacgtggg cctatataac     120
agtgaggacg agcctatctt tgacgccagt cgaaggacaa tcgaacgaat ggcctctaag     180
attagtaact tggacaagga ttctaagata ttggatatag gagcgggata tggaggcgcc     240
gccagatatt tagccaagaa atatgggtgc caagttgtcg cttttgaactt gtcagaggta     300 gaaaatgaaa gagatcgtaa gatgaatgaa gaccagggcc tcgaccatct cattaccgtc     360
gtggatgggt cctttgaaga atacccctac cccgatttta gcttcgatgt tgtttggagc     420
caggatgcga tcttgcactc tggaaataga gagcaagtca ttaaggaagt cgcacgagtt     480
ttgaaaagtg ggggagattt tgttttcact gatccaatgc agacggatga ttgtccggaa     540
ggagtgttac agccaatatt agatcgtatc cacctagaaa cactaggaag cccaggtttc     600
tatagagaat cagcgaagaa gtacggtatg aagaaaatag agttcgagaa gcacgcttca     660
cagttgccga cacattatgg tagggtactg aaggagaccg agtctcaaga agatgagttg     720
tccaaagtag ttagtcagaa ctatatcaac aatatgaagc aaggacttaa tcactgggtc     780
aacggcggca ataacggata cttgacctgg ggcatattcc acctaaggaa gaagtga       837
```

```
<210> SEQ ID NO 26
<211> LENGTH: 2154
<212> TYPE: DNA
<213> ORGANISM: Arabidopsis thaliana

<400> SEQUENCE: 26
atggaggagc tagatcgttc acgtgctttt gccagagacg tcaaacgtat cgtcgttaag      60
gttgggacag cagttgttac tggaaaaggt ggaagattgg ctcttggtcg tttaggagca     120
ctgtgtgaac agcttgcgga attaaactcg gatggatttg aggtgatatt ggtgtcatct     180
ggtgcggttg gtcttggcag gcaaaggctt cgttatcgac aattagtcaa tagcagcttt     240
gcggatcttc agaagcctca gactgaactt gatgggaagg cttgtgctgg tgttggacaa     300
agcagtctta tggcttacta tgagactatg tttgaccagc ttgatgtgac ggcagctcaa     360
cttctggtga atgacagtag ttttagagac aaggatttca ggaagcaact taatgaaact     420
gtcaagtcta tgcttgattt gagggttatt ccaattttca atgagaatga tgctattagc     480
acccgaagag ccccatatca ggattcttct ggtatttct gggataacga tagcttagct     540
gctctactgg cgttggaact gaaagctgat cttctgattc ttctgagcga tgttgaaggt     600
ctttacacag gccctccaag tgatcctaac tcaaagttga tccacacttt tgttaaagaa     660
aaacatcaag atgagattac attcggcgac aaatcaagat tagggagagg gggtatgact     720
```

```
gcaaaagtca aagctgcagt caatgcagct tatgctggga ttcctgtcat cataaccagt    780
gggtattcag ctgagaacat agataaagtc ctcagaggac tacgtgttgg aaccttgttt    840
catcaagatg ctcgtttatg ggctccgatc acagattcta atgctcgtga catggcagtt    900
gctgcgaggg aaagttccag aaagcttcag gccttatctt cggaagacag gaaaaaaatt    960
ctgcttgata ttgccgatgc ccttgaagca aatgttacta caatcaaagc tgagaatgag   1020
ttagatgtag cttctgcaca agaggctggg ttggaagagt caatggtggc tcgcttagtt   1080
atgacacctg aaagatctc gagccttgca gcttcagttc gtaagctagc tgatatggaa   1140
gatccaatcg gccgtgtttt aaagaaaaca gaggtggcag atggtcttgt cttagagaag   1200
acctcatcac cattaggcgt acttctgatt gttttgaat cccgacctga tgcacttgta   1260
cagatagctt cacttgccat ccgtagtgga atggtcttc tgctgaaggg tggaaaggag   1320
gcccggcgat caaatgctat cttacacaag gtgatcactg atgcaattcc agagactgtt   1380
gggggtaaac tcattggact tgtgacttca agagaagaga ttcctgatt tgcttaagctt   1440 gatgacgtta tcgatcttgt gatcccaaga ggaagcaaca agcttgttac tcagataaaa   1500
aatactacaa aaatccctgt gctaggtcat gctgatggaa tctgtcatgt atatgtcgac   1560
aaggcttgtg atacggatat ggcaaagcgc atagtttctg atgcaaagtt ggactatcca   1620
gcagcctgta atgcgatgga aacccttctt gtgcataagg atctagagca gaatgctgtg   1680
cttaatgagc ttattttgc tctgcagagc aatggagtca ctttgtatgg tggaccaagg   1740
gcaagtaaga tactgaacat accagaagca cggtcattca accatgagta ctgtgccaag   1800
gcttgcactg ttgaagttgt agaagacgtt tatggtgcta tagatcacat tcaccgacat   1860
gggagtgcac acacagactg cattgtgaca gaggatcacg aagttgcaga gctattcctt   1920
cgccaagtgg atagcgctgc tgtgttccac aacgccagca caagattctc agatggtttc   1980
cgatttggac ttggtgcaga ggtggggta agcacgggca ggatccatgc tcgtggtcca   2040 gtcgggtcg aaggattact tacaacgaga tggataatga gaggaaaagg acaagttgtc   2100
gacggagaca atggaattgt ttacacccat caggacattc ccatccaagc ttaa          2154
```

<210> SEQ ID NO 27
<211> LENGTH: 1873
<212> TYPE: DNA
<213> ORGANISM: Arabidopsis thaliana

<400> SEQUENCE: 27

```
ctgaagttta tagaaattcg tgtatttttt tgccgttgaa aatgtttaca gtagttaaaa     60
atgaatgata aacggttttc gtagatggta gaactcaatc tctagacttg atcctctaca    120
cactcaaaca aaccacttgg ttacacgttc ttggttgagc ggatttcaaa tgtgaaacat    180
tttaactcat tttttttggt gaacctgacc aaaagaatat tgattgtaca agaaccaaag    240
ttaaaacttg ttttggtcgt tgttgaataa gaaaaccgtg ctctcagaag tctttatata    300
ggcaaacata taaattgtga attttgtttt ctttattatc aattacaatt tattttaaaa    360
tataaataaa gatataataa agctatatat tcacgaataa ttctaaaaaa gtggtaacaa    420
aaaatgactt gaaacatttt ttctagtttc aatttcaagt cattctaaga agttaaaatt    480
aaggaatatc acatgcatga agttacattg aaagtgtctt cttacaaaat agaaaaaaaa    540
taaaaaataa aaacatagta aatgttgtgc attattcttt caataattag ggaaaacaat    600
aatacagtat cttagatgtt tataagacca gtatttattc atccaggcct aacaaaactg    660
```

| | |
|---|---|
| cccgccgcga tttctcatgt aagtatgtaa ccttagttat taaacaaaat tgcatttctt | 720 |
| agacgttaac caacttaatt atttgtctta tagtcaacgt gatttttta ctttataata | 780 |
| atgcttcgat cgtaagttga atctcaatca atgtcttgat tcccgagaga aagtagagc | 840 |
| gttaaaattg ccgtacagaa catgatggag acattaatga attcaataaa atcggcgaag | 900 |
| ttggaggttt agctgaggga ggcctgtgtc atgctgattc gtttagttac caactcttct | 960 |
| ttcaaacatc tttagtatgt tactgctttc atcctcttta tttgatctac tgattatata | 1020 |
| tatatatatt ttttttttac tacattcgac attcgttgct aagagaatag aaaacaattt | 1080 |
| tcttttttcaa aattatcctt agtttgatat tggtatgaga gatttacatg taatttcgac | 1140 |
| tcttgaaaat agataaatgt atgttgagta ttgttgacta aagaaacta gatgaatgca | 1200 |
| tcaaatagaa gtgtcttttt gctttatgta cttccccact tgaaaacatg acgattctat | 1260 |
| gaacgatttc attcgtcata acgatagaat tagtttgtcc tacgaaaaca aatgtaaaac | 1320 |
| tactataatt ttcttgacgt aatattggtg ggtttcatgc tgcggctgtt ggttgggaaa | 1380 |
| cgtccaatat aaacatttct aattatgtat atacctgaaa atttgtaaaa gctaatctaa | 1440 |
| attgtgaaac atacataaca aatactttaa gaagaaaaag tcatcaagca aacaagaaga | 1500 |
| catgacctag aaccatttcc gagacattat attaatataa aattgatatt caaatcctcc | 1560 |
| acgatcttac agcttcaac tttgagtatt tcaacgtttt ctctgattac acataaacta | 1620 |
| aaatttgttt ttttgttttt ttaatagttg atagcatgtg ttaattatta gtttatatca | 1680 |
| tacaatgacc ttagaatccg cagatcattt caagaactca gaacaaaagc tgatgtattc | 1740 |
| acttacatca ttgaattgtg tcagtttgag taacccataa tataaatata cgcaagtcaa | 1800 |
| aatgcattga gcttatctct catttagact ttaaatttct gatttcagag aggtcaactc | 1860 |
| tttaagccaa gcc | 1873 |

<210> SEQ ID NO 28
<211> LENGTH: 1330
<212> TYPE: DNA
<213> ORGANISM: Arabidopsis thaliana

<400> SEQUENCE: 28

| | |
|---|---|
| gcattttttt tgcactttcc accgaaaaaa ttgggtctac acgatcaccc ggaatgtttc | 60 |
| gcccacccgg cccaaatgaa atgtggtgag atcttcttat aatcttggcc caaatttcca | 120 |
| tcatggatct taaacgttcg tttcattgtt tcttggattt tttttcatta actggtccat | 180 |
| ctcaaaatgg gcttccataa aaatgggctt ttttacaaaa gggttttgtt tcattaattg | 240 |
| atttcgtgt tttttatcc gtaacaatta tgctttcgtt tcctaattta tacgagcaaa | 300 |
| cgtaaaaatg tatagtattt gactatttgg ttttacgtat caacaatcaa caacatactg | 360 |
| tacatcagta catacacaat ttttttttaa catacacaaa cttactttat gtacaaatga | 420 |
| actattaaga aatggcttta gccttgttat tgcatgcatc ttcttaattt gtgtatgtga | 480 |
| aattcttcat aggagctaat taagggacga agacaaagtg tatccccctt catgtattac | 540 |
| ctaaacgtat cttagaattt caaaacattg ttttccttag aattttttaa aaaaattgta | 600 |
| aacatgcaca tccaacactg gaaagtggaa agaagtatat atatatgata tgttatctca | 660 |
| aaaaaactga aatgattgta ttaaaaacat actaaattct gactgatgat agatattgat | 720 |
| acgtaattca tttgtttatt attgttcgtt ttgttttcaa cactactatt cctgtcacgg | 780 |
| tctcatttaa taacaacaac aaaaaagacg tcaagatttg acttttgagt tcctcaattt | 840 |
| tttcaactcc agtatttaaa cagctaatta ttacataatt tatcgtaaga aaaaaaaaaa | 900 |

| | | | | |
|---|---|---|---|---|
| aaaaaacctt | atcccctga | tattgtagat | ctcgattgta | atcactacac | ctgatgccac | 960 |
| attaaataca | cacagagacg | taaataagag | tcaaaaaagt | cgatgaagcc | ttctgcatat | 1020 |
| ataacaacaa | agttgaatat | ataaagagta | aaattcatca | tactacaatc | ttgaaaaatt | 1080 |
| ataatttatt | agatggttaa | gtaaatttgt | tttatagtat | tgttatattc | ttttttttcca | 1140 |
| aaaaatatag | ggaaaacaaa | aaccagtaaa | aaaaaaagtc | aacttaattt | gctcaccacc | 1200 |
| ttcttgatca | tctaaacacc | tctttaataa | ttcaaaacta | aaaaaaaaag | gtataaatga | 1260 |
| aagagacaaa | agagggaagt | atatatcatc | aagcttgaag | aagagagaga | agaagaagaa | 1320 |
| ggaaaaaaga | | | | | 1330 |

<210> SEQ ID NO 29
<211> LENGTH: 900
<212> TYPE: DNA
<213> ORGANISM: Arabidopsis thaliana

<400> SEQUENCE: 29

| | | | | | |
|---|---|---|---|---|---|
| ggttttgtat | tgataggtgc | aagagactca | aaattctggt | ttcgatgtta | acagaattca | 60 |
| agtagctgcc | cacttgattc | gatttgtttt | gtatttggaa | acaaccatgg | ctggtcaagg | 120 |
| cccagcccgt | tgtgcttctg | aacctgccta | gtcccatgga | ctagatcttt | atccgcagac | 180 |
| tccaaaagaa | aaaggattgg | cgcagaggaa | ttgtcatgga | aacagaatga | acaagaaagg | 240 |
| gtgaagaaga | tcaaaggcat | atatgatctt | tacattctct | ttagcttatg | tatgcagaaa | 300 |
| attcacctaa | ttaaggacag | ggaacgtaac | ttggcttgca | ctcctctcac | caaaccttac | 360 |
| cccctaacta | attttaattc | aaaattacta | gtattttggc | cgatcacttt | atataataag | 420 |
| ataccagatt | tattatattt | acgaattatc | agcatgcata | tactgtatat | agtttttttt | 480 |
| ttgttaaagg | gtaaaataat | aggatccttt | tgaataaaat | gaacatatat | aattagtata | 540 |
| atgaaaacag | aaggaaatga | gattaggaca | gtaagtaaaa | tgagagagac | ctgcaaagga | 600 |
| taaaaaagag | aagcttaagg | aaaccgcgac | gatgaaagaa | agacatgtca | tcagctgatg | 660 |
| gatgtgagtg | atgagtttgt | tgcagttgtg | tagaaatttt | tactaaaaca | gttgttttta | 720 |
| caaaaaagaa | ataatataaa | acgaaagctt | agcttgaagg | caatggagac | tctacaacaa | 780 |
| actatgtacc | atacagagag | agaaactaaa | agcttttcac | acataaaaac | caaacttatt | 840 |
| cgtctctcat | tgatcaccgt | tttgttctct | caagatcgct | gctaatctcc | ggccgtccct | 900 |

<210> SEQ ID NO 30
<211> LENGTH: 1000
<212> TYPE: DNA
<213> ORGANISM: Arabidopsis thaliana

<400> SEQUENCE: 30

| | | | | | |
|---|---|---|---|---|---|
| cttgaatagt | atacatgtgt | gtggtcctgt | tgagattgac | ccacaaatat | tagagtaaac | 60 |
| tggggaattg | aaatcaatca | tggtggggat | ttcggaatct | atgtgtgttt | ctaagatatt | 120 |
| attgtttctt | ggaaattaat | tgttgttgca | ccataatata | atttatatta | tatagatagt | 180 |
| ctaggaaaat | aactcaagac | aaagagtgtg | taacacactc | caacctcagt | gacttccacc | 240 |
| cgtcaagctt | tcggctaca | tagcctttat | atacgattat | tttacatata | gttcagata | 300 |
| tatacagtac | tgcttgtata | ttttggtct | tataatacta | ccttatgtca | ttatatatag | 360 |
| tacatattat | acaagtttc | aatcttttca | tttataagca | tcgttcggta | tgtagaaggc | 420 |
| gaaacaaacc | cttaaaccta | atatttttt | ctggtccaaa | aactttctct | atcaagcttt | 480 |

```
tgcatttttt cttttaaaat agtaacagct cctccattgt tgggtggtcc cataaaaata     540
catcataacc atcatcagca acatataata gcgatagcct taagcttaaa gatccaagct     600
tttggatata atatctagtt acatgtatat atatatatat gtgtttgtat atttataggt     660
atatagtata ttatcgtgtg cgtccgtgtg taacatcact atcattaccc aacatacagc     720
ttttggaatt tcattggacc caagagccat tcgatccctt tcttataatt aaatataacg     780
aagcttgtaa taggctttgg ttttggtccc aaatacaaaa ctttaaggtt gtgccttgtt     840
tgtctaaggt tttcgcaata gcttccaaaa agacacgctt atgtttatat acatttcatt     900
ttccttcata tcattctctt ctctgccact tctccatctt gtttcttact catttctcta     960 acaatttttcc aaattaaata cgtttatagg atcatcgtgg                         1000
```

<210> SEQ ID NO 31
<211> LENGTH: 312
<212> TYPE: DNA
<213> ORGANISM: Arabidopsis thaliana

<400> SEQUENCE: 31

```
aaattttaag cctctacgta attttttta taaaacaccc ctccggatat tttaataatc      60
attaactgtc tgaacgtgaa gctgtatgtt gaaaattgca cgcttagaac aaaaggctta    120
accaaaaatg atccaaccgt gaagactcgg agaccggcgt acttagtttt taaattaatc    180
attgtctttg cttcaaagcc aatcctatga gactttgtct tgtctccaac ttgtatataa    240
gctctattcc tctactctgt ttcacaccat ctcttcttct tcttcctctt ctctcagtga    300
acaaatttgg ct                                                        312
```

<210> SEQ ID NO 32
<211> LENGTH: 412
<212> TYPE: DNA
<213> ORGANISM: Artificial sequence
<220> FEATURE:
<223> OTHER INFORMATION: Promoter

<400> SEQUENCE: 32

```
ttaaatgtat agctacaaac atttcgaact ctacgcttct gtaacatgct caactatgta     60
gctcgcacat cttgtgctag gctacataac aaccttacaa cctacattcg aggtagctcg    120
taacattaac tctcgcctaa tgtactccat aaaacataca ggagtttaat gagcttgcaa    180
cgatcagatt ctctgttgag ctgtgatgat ggttagagag agacatagaa ctgatataac    240
ggagatcttg attccaattg tttaaccacc ctcagagatt cctcttgcct ctctttcttg    300
atggtgtata tatgtattga ccggagaggt attgagaagg cagaacaaac atctttatct    360
ctctcaacat aatcttcttg atcaataaca aagagtctaa tatcaataaa aa            412
```

<210> SEQ ID NO 33
<211> LENGTH: 445
<212> TYPE: DNA
<213> ORGANISM: Artificial sequence
<220> FEATURE:
<223> OTHER INFORMATION: Promoter

<400> SEQUENCE: 33

```
ttaaatgtat agcttgcaaa aaaaaaactc tacgcttctg taacatgctc aactatgtag     60
ctcgcacatc ttgtgctagg ctacataaca accttacaac ctataattac attttagtct    120
ttacgtttaa ctctcgccta atgtactcca taaaacatac aggagtttaa tgagcttgca    180
acgatcagaa tgtcttaatt gtcactcgtg caaaaagtaa attctctgtt gagctgtgat    240
```

-continued

| | |
|---|---|
| gatggttaga gagagacata gaactgatat aacggagatc ttgattccaa ttgtttaacc | 300 |
| accctcagag attcctcttg cctctctttc ttgatggtgt atatatgtat tgaccggaga | 360 |
| ggtattgaga aggcagaaca aacatcttta tctctctcaa cataatcttc ttgatcaata | 420 |
| acaaagagtc taatatcaat aaaaa | 445 |

<210> SEQ ID NO 34
<211> LENGTH: 1802
<212> TYPE: DNA
<213> ORGANISM: Oryza sativa

<400> SEQUENCE: 34

| | |
|---|---|
| gaaacacctc gtgaacgaaa tacctagcaa actctgtaag gcctgagatt ttcaccaagt | 60 |
| cgagtggctg atctgcaacg agctgtaccg atcaaaatat gggttctttc attctttgtg | 120 |
| atgtgtgctg attttccaat cgaaaatcat tgtggcaaga ttttgtcagg gcatcgccgt | 180 |
| ccacactctg ctcccccacc ggggatgcct accaagggaa gaagaggcgt cataactgcc | 240 |
| atacacttgt gctgtctacg gccatcagag cattgaccat acgggcctac ttcacagaac | 300 |
| atgattgacc tgtaaaaatc agcttcgac tttgagttcc gaatcctgtt gatttttcat | 360 |
| tgagtttaat taggagtagg tggcattgct cttcagatga tatgtcgatt tctggcattg | 420 |
| ctcttttttaa tacaaggtga tgaaaattca gctgcctgaa ttggagtttt gttttcctga | 480 |
| actgtagtat ctgaactctg aagacagtta ctgatagtgg tagtacaaga tagtactccc | 540 |
| tccgttttga aatgtttgac gccgttgact ttttatcaca tgtttgatca ttcgtcttat | 600 |
| tcaaaaaatt taagtaatta ttaattatttt tcctatcatt tgattcatta ttaaatatat | 660 |
| ttttatgtag acatataatt ttacatatct cacaaaagtt tttgaataag acgaacagtt | 720 |
| aaacatgtgc taaaaagtca acggtgtcaa acatttcgaa ctggagggag tatcctacag | 780 |
| gtacagtacg gcaaaaaaag aaaaactgaa tgtgagctaa gctcaatgag agaagctagg | 840 |
| attgcaaatt gctgaagtac tccaactgac atgagatttt tcaatagtag caggtcagtt | 900 |
| ttgacagtga ccatccaagt gcaacgtcct ctgctctgac attgcttagc attgctaacc | 960 |
| gaagcatgca cactgcgtaa tagagtggtt aggataaccc cttattgtaa tgtcaccttt | 1020 |
| gcaaatcctt aactgctcgg atatttcaat ttggtcacca gagatggcaa tcctacaatt | 1080 |
| gaaaatttgt tcagttgcca cggatccatc attaatctgg caatggcggc aacctctgac | 1140 |
| agggacaatg gcaaattcgg ccaatagtaa atttcggtac ggtttatcct agttggcatt | 1200 |
| ggcacacatg gttcgtctct tctacgagta tagattatga aaaatgtcaa cttacaacag | 1260 |
| gtgacgaatt tcgcaaaaaa aacgtattaa cattcggcat ggaaaacgta cgtagaatga | 1320 |
| ccaaaaatat ccatccctat agtatcattt ctttcagggg agcccccaat ctacaaaaga | 1380 |
| aaaagaattt gttcgtcacc catatatcgg cgtcatgacc tcgacgtcgc gctttatcca | 1440 |
| ggcatatagt ttacaacacc ttgtgaattg aaaacccaca attatttcag tctaacagca | 1500 |
| gacagaggca acgttgctct cgttgtcgtt cacggggga tgacgcgcgg ttttatgccc | 1560 |
| tcgacgagaa tacaaaatca agtatgcgtt tctgtttctc ggccaatgct gatccgacaa | 1620 |
| cgtgtttgaa cggattaaac aaaatctgaa tccccgtcga aaaattagac cagaaacaat | 1680 |
| gatcttatgc tgattaatta gggctaatga gctatgcatg caagcactgt acccagtggt | 1740 |
| gctccgacaa gtaggcctgc ctaatcaaaa ggcagtgagg actgtaacta ctagtacctg | 1800 |
| cc | 1802 |

<210> SEQ ID NO 35
<211> LENGTH: 1847
<212> TYPE: DNA
<213> ORGANISM: Oryza sativa

<400> SEQUENCE: 35

| | | | | | | |
|---|---|---|---|---|---|---|
| tccttcatat | tataaaacag | tttgatcttt | ttcctattca | aaatttatta | agggctagtt | 60 |
| tgatttgaag | tcaaattaaa | cttgccatac | caaatatcgg | cattttaaat | agtgattttg | 120 |
| gcaatgtttg | gtttgctacc | aatagttgct | aataccacac | aaatattacc | aacagattgg | 180 |
| cattggcaaa | aatttgtcta | tgatttggca | ttgccaatag | tttggcatgg | ttgcaaatta | 240 |
| accaaacaag | ccctaaaaaa | cacggtaata | tttaacacaa | aataaatata | gtattaaaat | 300 |
| aattcaaata | ttagatttag | taacactaat | taggtattgt | agatgttttg | ctaattttt | 360 |
| tgttgtggtt | gttgttgttg | ttgtgtgtgt | gagatgccta | aatgcacaca | tgtagaaacc | 420 |
| aaagaaaaca | gaaagatatt | taaattaaca | gatataaata | tatacagcac | atatgtatat | 480 |
| atctagctag | tttagttaag | ggcgcggcgg | tgatgatgca | tgatctgaaa | gagacagtgt | 540 |
| gcaagctgat | tattgtatgt | tagatttaat | taaatagtta | ataatggca | acatttaact | 600 |
| gctccatatc | gatatggata | tatctaatcc | tacatgtcac | atgtgcatac | gtacttgtta | 660 |
| ttaacgctga | gactgaatta | atatacgccc | tccgtttcaa | aatgtttgat | accgttaact | 720 |
| tttcagtacg | tgtttgacta | ttcatcttat | taaaaaaatc | aagtagttat | ttattctttt | 780 |
| catattattt | gatttattgt | taaatatatt | ttcatgtaca | gatatagttt | tacatatttc | 840 |
| ataattttt | taataagacg | aacggttaaa | catgtgctaa | aaagccaacg | gtgtcaaata | 900 |
| ttttgaaacg | gagggagtat | tgcagctagc | tcgcgattaa | ccaaggtagc | tatggccggc | 960 |
| cgacgcttct | aactggcgcg | cgtgccaact | ctcgatcgac | tgctaatcat | gcttgcttaa | 1020 |
| tttggaaggc | cacgacaatc | cattttaagt | cgtataatta | accttttgta | attttgagtg | 1080 |
| agaccacaag | tagatcgacg | gagacattct | acttggcatg | catgcaatgc | agaaacgcgc | 1140 |
| agagctagca | ttatgtatgc | ttgtgaattg | tgtgagagag | aattagctag | attgataatg | 1200 |
| tacatatatg | aatttgtatg | cgatatatat | gctagtatat | ataatatgca | gttaagtgta | 1260 |
| caaattaaat | gcactaattt | gcattacaaa | attaattaat | acacatgtgg | ttattaattt | 1320 |
| gtcccgaagc | gagaataata | aagccgggtt | gcagtgtgac | gagaggggat | gatcgattag | 1380 |
| tttacattac | ccttttgatc | tcatggcttt | gactcttagg | gtttgtacgc | tacctagcta | 1440 |
| gctttgcttt | cggacagagc | tagaggtgat | tattactccc | tccgtttcaa | aatgtttgac | 1500 |
| accgttgact | ttttagtacg | tgtttgacca | ttcgtcttat | tcaaaaaatt | taagtaatta | 1560 |
| tttattcttt | tcatatcatt | tgattcattg | ttaaataaac | tttcatgtac | acatatagtt | 1620 |
| ttacatatttt | cacaattttt | tttaaataag | acaaatggtc | aaacatgtgc | taaaaagtca | 1680 |
| acggtatcaa | acatttttaa | acggagggag | tagtaattag | aaatgaataa | aaaccctagc | 1740 |
| tagctagcta | catgttgatg | cgtattagtt | attcatgaca | tcagctagct | aggcagacga | 1800 |
| gagtacgtcg | agtagtattt | atagccggca | tggaggaagc | gagagga | | 1847 |

<210> SEQ ID NO 36
<211> LENGTH: 1023
<212> TYPE: DNA
<213> ORGANISM: Oryza sativa

<400> SEQUENCE: 36

| | | | | | | |
|---|---|---|---|---|---|---|
| agcatcagca | gcgcatgcac | tagcagctta | gctactgcgc | gcgtaccaga | gagagatcat | 60 |

-continued

```
cagctcaagt agctaagcta gctataatct gctagctagc tcgatcagac acttaattac      120
ctgctaggtg gtggtcgatc gaagaagaag aagatggcgg agggtaaaga agaagatgtt      180
agacttggtg ccaacaagtt cacagaaggc cagcctctgg aactaccgc acaaacagat       240 aaggattata aagaggaacc tcccgctccc ctctttgagc ctggagagct aaatcctgg       300 tcattttaca gagctggaat tgccgagttt atggctactt ttcttttcct atatatctcc      360
attctcacag tgatgggggt tgggagatcc acctctaagt gcgcttccgt gggtattcaa      420
ggtattgctt gggcatttgg tgggatgatc ttcgttttag tgtactgtac ggctggaatc      480 tctggggtc acattaaccc ggctgtaaca ttcggcttat tcttggctag aaagctaagc       540
cttacccgag ctcttttcta catggtgatg caatgtctgg agccatctg cggagctggt       600 gttgttaaag ggtttatgga aggaccatat cagcgtctta agggaggtgc caatatggta      660
tctcacggtt atacaaaagg ggatgggtta ggcgcagaaa ttgttgggac atttgtttta      720
gtctatacag tcttctctgc aacgatgca aagagaaacg ctagggactc ccacgttccg       780
atcttagctc ctctccctat tggatttgca gtgtttctag tgcatcttgc tacaatccct      840
gttacaggaa cagggatcaa ccccgctaga tcattaggag cggcaataat ctacaataaa      900
gatcaggcgt gggatgacca ttggatattc tgggttggac cttttattgg agctgcttta      960
gcagcagtgt accaccaatt gatcattaga gctataccat ttaaaagtaa tcgagcatgc     1020
tga                                                                    1023
```

<210> SEQ ID NO 37
<211> LENGTH: 1059
<212> TYPE: DNA
<213> ORGANISM: Oryza sativa

<400> SEQUENCE: 37

```
acctcccagt tgctcaggct tctcaacctt agctagctcg atctccctat aaatactcct       60
gctcattacc acaacgagca agcgatcgac ggagcgagcg agctagccag ccagtgttag      120
agcttgagct gcttgttctt cttctacctc ctgcactcgc gtgctgcaca agtagctcag      180
ctagatagag cgtcagaaat ttaaatgaaa atgggaagat caccttgttg tgataaaaat      240
ggagtgaaga agggaccttg gactgctgag gaggatcaga aactcatcga ttatattcga      300
tttcatggtc ctggcaactg gcgtacgctc cccaaaaatg ctggactcca tagatgtgga      360
aaaagctgcc gtcttcgatg gaccaattat ctaagaccgg acatcaagag aggaagattc      420
tcgttcgagg aagaagaaac tatcattcag ctacacagtg ttatgggaaa caagtggtca      480
gcaatagccg ctcgtctacc agggaggacc gataacgaaa taaaaaacca ttggaacact      540
cacatccgca agagacttgt aaggagtggt atcgaccctg ttactcattc tccacgcctt      600
gatcttcttg atttgtcctc acttttgagt gcactttca accagccaaa cttttcagca      660
gttgcaacac atgcgtcttc tcttcttaat cctgatgtat tgaggttggc ctctctacta      720
ctgccacttc aaaaccctaa tccagtttac ccatcgaacc tcgaccaaaa tcttcaaact      780
ccaaatacat catcagaatc gtctcaacca caagctgaaa ccagtacagt cccaacaaac      840
tatgaaactt catcattgga gcctatgaac gcaagactcg acgacgttgg tcttgcagat      900
gtattaccac ctttgtcaga gagttttgac ttagactcgc tcatgtcaac gccaatgtct      960
gatccacgac aaaaatagcat tgaagcagaa accaactcca gcactttctt cgactttggt     1020
attccggaag atttcatctt agatgacttt atgttttga                             1059
```

<210> SEQ ID NO 38
<211> LENGTH: 996
<212> TYPE: DNA
<213> ORGANISM: Oryza sativa

<400> SEQUENCE: 38

| | | | | | |
|---|---|---|---|---|---|
| agcatcagca | gcgcatgcac | tagcagctta | gctactgcgc | gcgtaccaga | gagagatcat | 60 |
| cagctcaagt | agctaagcta | gctataatct | gctagctagc | tcgatcagac | acttaattac | 120 |
| ctgctaggtg | gtggtcgatc | gaagaagaag | aagatggcta | agaagtttc | cgaagaggga | 180 |
| catgctcctc | atgggaaaga | ttatgttgat | cctcctcctg | cacctctcat | cgactgggcg | 240 |
| gaggttaaat | tgtggtcgtt | ttatagagct | gttatcgctg | aattcatcgc | tacactactt | 300 |
| tttctctatg | taactatagc | aacggtgatt | ggccacaaga | agcagaccgg | tccttgtgat | 360 |
| ggagttgggc | ttctcggaat | tgcatgggcc | ttcggaggaa | tgatattcat | actcgtttat | 420 |
| tgtaccgccg | gaatatctgg | tgggcatatt | aaccccgctg | tgacatttgg | tctttttttg | 480 |
| gctaggaaag | ttagtctaat | cagggcgtta | gcttacatgg | tcgcgcaatg | tttaggtgct | 540 |
| atctgtggag | tcggactagt | aaaagcgttc | atgaaacatt | catacaactc | actgggaggg | 600 |
| ggagctaatt | ttgttaatgc | tggttataat | aaggggaccg | cgctaggagc | tgagataatt | 660 |
| ggtaccttcg | tgctggtcta | tactgtattt | tccgcgactg | atcctaagcg | ttcagctcga | 720 |
| gattctcacg | taccggtgct | tgctcctta | cctatcgggt | tcgctgtgtt | tatggttcac | 780 |
| cttgcaacga | tacctatcac | aggtacagga | atcaatcctg | ctaggtcatt | cggtgccgct | 840 |
| gttatacaca | caacgacaa | aatctgggac | gatcaatgga | ttttttgggt | tggacccttt | 900 |
| gtcggagcat | tagcggctgc | agcatatcac | cagtacattt | tgagagctgc | tgctatcaag | 960 |
| gcattgggta | gtttcagatc | aaatcgtagt | aattga | | | 996 |

<210> SEQ ID NO 39
<211> LENGTH: 915
<212> TYPE: DNA
<213> ORGANISM: Oryza sativa

<400> SEQUENCE: 39

| | | | | | |
|---|---|---|---|---|---|
| agcatcagca | gcgcatgcac | tagcagctta | gctactgcgc | gcgtaccaga | gagagatcat | 60 |
| cagctcaagt | agctaagcta | gctataatct | gctagctagc | tcgatcagac | acttaattac | 120 |
| ctgctaggtg | gtggtcgatc | gaagaagaag | aagatgccga | tcagaaacat | cgccatcggc | 180 |
| ggagtccaag | aagaagtgac | tcacccaagc | gcacttaggg | cggctctcgc | cgagtttatc | 240 |
| tcaacgttga | tatttgtttt | cgccggctca | ggctccggaa | ttgctttcaa | caagctcact | 300 |
| gacaatggag | ccaccactcc | ttccggcctc | gtcgccgctg | ccttagctca | tgctttcgga | 360 |
| ctcttcgtcg | ctgtttccgt | cggtgctaac | atctccggtg | gtcacgttaa | tcccgccgtt | 420 |
| accttcggtg | cctcctcgg | tggtaacatc | actctcctcc | gtggtattct | ctactggatc | 480 |
| gctcagcttc | ttggctccgt | cgtcgcttgt | ttcctcctta | ctttcgccac | cggtggcttg | 540 |
| gcggttccgg | cgttcggact | ctctgccgga | gttggatcat | taaacgcatt | cgtcttcgag | 600 |
| atcgtgatga | ccttcgggct | cgtctacaca | gtctacgcaa | ccgccatcga | ccccaaaaac | 660 |
| ggaagtctcg | gaacaatcgc | accaatcgcc | attggtttca | tcgtcggagc | aaacatcctc | 720 |
| gccggtggag | ctttcagtgg | agcctccatg | aacccagccg | tcgctttcgg | accagccgtc | 780 |
| gtgagctggt | cgtggagcaa | ccactgggtt | tactgggctg | tcctcttgt | cggtggtgga | 840 |
| ctcgccggac | tcatctacga | gtttgttttc | atcggcggaa | acgcccatga | gcaattgccc | 900 |

```
                                accactgatt attga                             915

<210> SEQ ID NO 40
<211> LENGTH: 1268
<212> TYPE: DNA
<213> ORGANISM: Oryza sativa

<400> SEQUENCE: 40
acctcccagt tgctcaggct tctcaacctt agctagctcg atctccctat aaatactcct            60
gctcattacc acaacgagca agcgatcgac ggagcgagcg agctagccag ccagtgttag           120
agcttgagct gcttgttctt cttctacctc ctgcactcgc gtgctgcaca agtagctcag           180
ctagatagag cgtcagaata tttttacaac aattaccaac aacaacaaac aacaaacaac           240
attacaatta ctatttacaa ttaaaaatgg gaagagcacc atgctgcgac aaggcaaacg           300
tgaagaaagg accttggtcc ccggaagaag atgtgaagct caaggattac atcgacaaat           360
atggcactgg tggcaactgg atcgcactgc ctcagaaaat tgggctgaag agatgtggta           420
agagttgcag actgagatgg cttaattact taagaccaaa catcaaacat ggtggttttt           480
ctgaggaaga agatagaatc atcttgagtc tctacattag cattggaagc cggtggtcca           540
taattgcagc tcagcttcct ggaaggactg acaatgacat caagaattat tggaacacaa           600
aactgaagaa gaaacttcta ggaagacaga aacaaatgaa tcgtcaagac tccataaccg           660
attctactga gaacaacctc agcaacaata acaacaataa gagtcctcag aatctgagca           720
attcggcact ggagaggctc cagcttcaca tgcagcttca gaatctacag agccctttct           780
ctagtttcta caacaaccct atcttgtggc ccaagctgca tccattgctc cagagcacta           840
caactaatca aaaccctaaa cttgcatctc aagagagctt ccacccttta ggagttaacg           900
ttgatcatca gcacaacaat accaaactag ctcagataaa caatggagcc tcttctctct           960
attcggagaa cgtagagcaa tcccaaaacc ctgctcatga atttcaacct aatttcggtt          1020
tttcacagga ccttcgatta gataatcata acatggactt tatgaacaga ggggtttcta          1080
aagaactgtt tcaagtgggc aacgagtttg agctaacgaa cggttcgagt tggtggtcag          1140
aggaagtgga actagagagg aaaacgacat cgtcgagttc ttgggggtca gcttctgtgc          1200
ttgatcagac aactgaggga atggttatgc ttcaagatta cgctcagatg agctaccaca          1260
gtgtttga                                                                    1268

<210> SEQ ID NO 41
<211> LENGTH: 1107
<212> TYPE: DNA
<213> ORGANISM: Oryza sativa

<400> SEQUENCE: 41
atggggcggg cgccgtgctg cgagaagagc gggctgaaga aggggccgtg gacgcccgag            60
gaggacgaga agctcatcgc ctacatcaag gagcacggcc agggcaactg gcgcacgctc           120
cccaagaatg ccgggctctc gaggtgcggg aagagctgcc ggctgcggtg gacgaactac           180
cttaggccgg acatcaagcg tggtcgcttc tccttcgagg aggaggaggc catcatccag           240
ctccacagca tcctcggcaa caagtggtca gcgatcgcgg cgcggctgcc gggccggacg           300
gacaacgaga tcaagaacta ctggaacacg cacatccgca agcgcctcct ccgcatgggc           360
atagaccccg tgacccacgc gccgcgtctc gacctcctcg atctcacctc cctcctcaag           420
cccgccgccg ccgccgcgta ctaccccacg caggccgacc tcgacacgct ccgcgcgctc           480
```

```
gagccgctcg ccggctaccc ggacctgctc cgcctcgcct ccgccatcct ccccgccgcc    540
acgacgaccg gcgcagccgc cgccgccgcc gccgagcagg cgcagcttct cctgccgtgg    600
ctgcttcagg cgcagatggc gcagcagcaa cagcaggtga cgccgccgcc gccgccgccg    660
ccgcaggccg cggcgaccga acagttcttg caggccacca gcaccgcctg ccaccaaatg    720
ccaggcctgg ttcacgccag cccgacgcag cagctggcgc agcaaccgca ggatcacatg    780
gcggcggcga cctgccaccg ccgcggcgcc gtgcagcacc cgagctacga caaccagctc    840
gactacgtgc cggcgctgat gcagatggcg tccgacgcgt ccaacctgca gcagtggagc    900
agcacggtct cgagtagcaa caaccacaac gtcaactccg gcgtgtccac gccgtcgtcg    960
agcccagcag ccgccggaca gatcaactca tcctctacga cgacgacgac gacgtatggc   1020
ttgaacgcga gcggtgacgt cgacgacgct gggctgctca tcaacatgca cctatccgag   1080
ctcctcgacg tgagcgacta catgtaa                                       1107
```

<210> SEQ ID NO 42
<211> LENGTH: 1116
<212> TYPE: DNA
<213> ORGANISM: Oryza sativa

<400> SEQUENCE: 42

```
atggggaagg gccgggcacc gtgctgcgcc aaggtggggc tgaacaaggg gtcgtggacg     60
ccggaggagg acatgaggct cgtcgcctac attcagaagt acggccacgc caactggcgc    120
gccctgccca gcaagcagg tttgctccgg tgcgggaaga gctgccgact ccggtggatc    180
aactacctcc ggccggacct caagcgcggc aacttcaccg ccgaggagga ggagaccatc    240
atcaagcttc acggccttct cggcaacaag tggtcgaaga tcgcgtcgtg cctgccgggg    300
aggacggaca acgagatcaa gaacgtctgg aacacgcacc tcaagaagcg ggtgtcgccg    360
gagcagaaga agggtggggg caagagcaag aagaagacga cctgcaccga cgtgctcgtc    420
ccgtccccat cgccgtcgtc gtccaccacc accacgacca actgctccag cggcgactca    480
gccggcgagc agagcaacac gagcaaggag gaggaggagg agacggacaa gatcgagatc    540
cccatgctcg agctcgaccc ctgctgcttc gacttcgaca tgctggttga ccccgttgtc    600
ccggacacgt actgccccgc ggtgtcggcg tcggcgtcgg cgtcggcgcc gacgtcgccg    660
tgctcgtcca cgtccccgtc gtgcgcccgt gcaggcgtgg acccgctgct cgacctgccc    720
gaaatcgtgg acctcgggcc ggagctatgg agcatcatgg acggcggcgc cggcgacggg    780
tgcaccgaag cgccgccgcc ggcgtggagc aatgcggcgg cggcggcggc ggccaatgca    840
acagtggcca ccacgaccag cctggaggag gaggagggga aggagtggtg gttggaggac    900
ttggagaagg agctcgggct gtgggggccc acggacgact accactgcca cccgggccca    960
caaggtcagc ccggtcgcgc gggcccacca ccctccgccg ttgtggagga cccagtgtcg   1020
tgctacttcc aagcgggccc cacggcagcc gccacgtggc agggacacga gccctcggct   1080
gtcatcacga gtaaccccat ggattactac gtgtaa                             1116
```

<210> SEQ ID NO 43
<211> LENGTH: 1023
<212> TYPE: DNA
<213> ORGANISM: Oryza sativa

<400> SEQUENCE: 43

```
atggggaggg gacgagcgcc gtgctgcgcc aaggtggggc tgaacagggg ttcgtggacg     60
ccgcaggagg acatgcggct catcgcctac atccagaagc acgccacgc caactggcga    120
```

-continued

| | |
|---|---|
| gccctcccca agcaggccgg attgctgcgg tgcggcaaga gctgccgcct ccggtggatc | 180 |
| aactacctgc gccccgacct gaagcgcggc aacttcaccg ccgacgagga ggacaccatc | 240 |
| atcaagctgc acggcctact cgggaacaag tggtccaaga tcgcgtcgtg cctgcccggg | 300 |
| aggacggaca acgagatcaa gaacgtgtgg aacacccacc tgaagaagag ggtgtcgcag | 360 |
| agagagaagc caggtgacac caagaagaag ggcaaggccg cggacgccag cgacgacgcc | 420 |
| gacgcgcatt ccccgtcgtc gtcggcgtcc tcctcgacga cgacggcggc caataacaac | 480 |
| aacagcggcg acacggccgg cgagcagtgc ggcacgagca aggagcccga gaacgtcgac | 540 |
| gtgtccttct tcgagcaaga catcgacatc tcggacatgc tggtgacgc gcccacggag | 600 |
| gcgccgctgg tcgcggcgcc aatgccgccg tccccgtgct cgtcgtcctc cctgacgacg | 660 |
| acgacgtgcg tcgcgccgt gtcggacgag ctgctcgacc tgccggagat cgacatcgag | 720 |
| ccggatatat ggagcatcat cgacggctac ggcggcgatg agcccggcga cggcgatgca | 780 |
| acagtgccat gtaccgccag cccggggagag gaggagcag agtggtgggt agagaatttg | 840 |
| gagaaggagc tcggcctgtg ggggcccatg gacgagtccc tggcccatcc ggacccaccc | 900 |
| ggacaggttt gttacccggg cccactcacg gaaacagagg gggacccagt ctccacctac | 960 |
| ttccagtccg ggcccaccgc ctctccgctc caggagatcg catcacccgc cgttctctca | 1020 |
| tga | 1023 |

<210> SEQ ID NO 44
<211> LENGTH: 951
<212> TYPE: DNA
<213> ORGANISM: Oryza sativa

<400> SEQUENCE: 44

| | |
|---|---|
| atggggaggg caccttgctg tgacaaggca acagtgaaga aggggccatg gtcacctgag | 60 |
| gaggatgcaa tgctcaagaa ctacattgag gagcatggca ccgtggcaa ctggattgca | 120 |
| ctgcctcaca agattgggct gaagaggtgt ggcaagagct gcaggctaag gtggctgaat | 180 |
| tacctgaggc caaacataaa gcatggggac ttcaccccag aggaggacag catcatctgc | 240 |
| agcctctaca ttagcatagg gagcaggtgg tcaatcatag cagcacagct gccagggagg | 300 |
| acggacaacg atgtcaagaa ctactggaac acaaagctga agaagagact ccttggccgg | 360 |
| cgcaaggacc gcggcggcgg ccaccaccac cgcagccaga gcaccgccga cgatcttccg | 420 |
| gccggtggtg acggcggcat gaacgacggc ggcggcggcg cggagagcg gtcgctgagc | 480 |
| gcgtcggcga tggagaggat ccagctctgc atgcagctgc aggagctgca gaacccactg | 540 |
| tccatccacc acaaccccct tgctctctcat cagtggccaa gcaaggccac cattgatgat | 600 |
| cagaatcaca acaatgtcac tgtggctgaa catggaatgt caagctctgt gagcgaccac | 660 |
| caccgcctcg atgggcagca gctggagagc ggcgccggcg ccgccgccat gcagcaggcg | 720 |
| tcgccgtcga gcgcggcga gaactccaac gtcgtcgtcg ccatcgaggc cgagctccag | 780 |
| gagcttctct acgccggcgg cggcgcgatc gtcgacggcg gcgcgccgcc gcaggggat | 840 |
| gtggactggt ggagctatga tcagggaaag cagtcacctg tgacttgctg ggatttcacc | 900 |
| cctgaaacca gctccatctt ccaggattat gcaacagttt atgacatctg a | 951 |

<210> SEQ ID NO 45
<211> LENGTH: 957
<212> TYPE: DNA
<213> ORGANISM: Oryza sativa

<400> SEQUENCE: 45

```
atggggaggg cgccgtgctg cgacaaggcg agcgtgaaga gggggccgtg gtcgccggag      60
gaggacgagc tgctgcggag ctacgtccgc agccacggca ccgtggcaa ctggatcgcg      120
ctcccgcaga aagcagggct gaaccggtgc gggaagagct gtaggctgcg gtggctcaac      180
tacctccgcc cggacatcaa gcacggcggc tacaccgacc aggaggaccg gatcatctgt      240
tccctctaca actccatcgg aagcaggtgg tccatcatcg cgtcgaagct gcccggccgg      300
acggacaacg acgtcaagaa ttactggaat accaagctca agaagaaggc catggccatg      360
catcatcatc atcagccgcc gccgccgcag cagcaacact accaccacca ccaccaccac      420
cgtgtcgccg gcggtggcgc gcgcgtcacg ctcgtgtcgc ctccgcccgc cccgcagagc      480
caatgcgcgt ccatgcagcc gtcgccggcg tccgcctcct cgtccggcgg cgacgcgtgc      540
agcttcggcg ccgccgccat gtactccccc tccccgtcaa cccagcaggc gccacaggcg      600
gcgacgctcg cggtcgcggg gtacacctcc gtggcgacgg cggcggcggc ggcggcggtg      660
gcggcgcagc gctcgccgct cgacgagctg atctgccagg tgccaccacc tcccactact      720
accgccgccg actgctgggc cagcggcgtg accctcgacg acgtgttctt gcccgagctc      780
gtcggagccg gcgagttccc caacggcgac ctcttcggcg ggttcggccc gctgctccag      840
gacaggtcgt ccatggagct ctccgcgtgc tacttcccca cgccgcggc ggcggagatg      900
tggccggcgg ccacggacat cgtcaagccg gccgggctgt gccacagcct gacatga       957
```

<210> SEQ ID NO 46
<211> LENGTH: 795
<212> TYPE: DNA
<213> ORGANISM: Oryza sativa

<400> SEQUENCE: 46

```
atggggagga cgccgtgctg cgacagggag gcggtgaaga ggggcccgtg gtcgccggag      60
gaggacgacg cgctgcgcga ctacatcaac cgccacggca ccgccggcaa ctggatctcc      120
ctccccaaca aggccgggtt gaggaggtgc ggcaagagct gcaggctgcg gtggctcaac      180
tacctccgcc ccgacatccg ccatggcgcc ttcaccgacg aggaggacgc catcatcacc      240
tccctctact ccaagctcgg cagcaagtgg tcgaccatcg cggcgcagct ggagaggagg      300
acggacaacg acgtcaagaa ccactggaac accaagctca agcgccgcct cgccgccgcc      360
gccgcctgca cgcccttact gccgctcccg gcgccgccgc ccctcgccgc cacgcacacg      420
tcgccgtcgt cgtcgctgct gctcctcccg ccgctcgccg taccgaccgt caagaccgag      480
gcgtacacct gcgacgactt cctgcagcag ctgctgccga ccgccaccgc cgccacggcg      540
ctccgggatc ccttcgccga cggcgccgcc acggacggcg gctcgacgtc gcctccgcc      600
gcgtcgtcgg ggtccaactg gtcggcggac accggcgtcg tcgtcgtcgg tggcggcggc      660
ggcggcgggc tgttcccgga attctgcatg agctccgacg acctcgccgg cgccgccacg      720
gcggaggacg accacttcat cggcggcggc tactactacc ctctcgatcc gagcttgtca      780
tcatcactag tgtag                                                      795
```

SYNTHETIC DESALINATION GENETIC CIRCUIT IN PLANTS

CROSS-REFERENCE TO RELATED APPLICATIONS

This application is a 371 National Stage application of International Application No. PCT/US2018/024053, filed Mar. 23, 2018, which claims the priority of U.S. Provisional Appl. Ser. No. 62/475,642, filed Mar. 23, 2017, the entire disclosures of which are incorporated herein by reference in their entirety.

STATEMENT REGARDING FEDERALLY SPONSORED RESEARCH OR DEVELOPMENT

This invention was made with government support under grant HR0011-16-2-0005 awarded by the Department of Defense/Defense Advanced Research Projects Agency. The government has certain rights in the invention.

INCORPORATION OF SEQUENCE LISTING

A sequence listing contained in the file named "CSUV002WO.txt" which is 67 kilobytes (measured in MS-Windows®) and created on Mar. 23, 2018, is filed electronically herewith and incorporated by reference in its entirety.

FIELD OF THE INVENTION

The present disclosure relates to the field of biotechnology. More specifically, the disclosure relates to compositions and methods for generation of plants that can remove a salt or other impurity from water, for example plants that can remove sodium chloride from salt or sea water. As such, the present disclosure also provides methods for engineering crop plants, for example rice, for growth in saline water.

BACKGROUND

One of the greatest limits to humanity and sustainable life on Earth is fresh water. However, the majority of water on Earth is salt water. Physical structures assembled as commercial desalination systems, i.e., conventional desalination plants, are able to produce fresh water from salt water, but these structures are extremely expensive to build and maintain, use the energy equivalent of a city of 50,000 people, and generate massive amounts of salt brine that must be re-pumped out into the ocean. Therefore, the fresh water that is produced is very expensive, and not done in a sustainable manner.

What is needed are new compositions and methods for generation of fresh water from salt water, grey water, or otherwise contaminated water, for a relatively low cost and in a sustainable manner.

SUMMARY OF THE INVENTION

The present disclosure provides a transgenic plant genetically engineered to produce purified water, comprising genetically encoded physical barrier components, genetically encoded water filtering and transport components, and genetically encoded water retention and pumping components, wherein the plant produces purified water when grown in water containing an impurity, and wherein at least one of the components is exogenously provided to the plant.

In certain embodiments the genetically encoded physical barrier components comprise suberin and a Casparian Strip. In particular embodiments the suberin is encoded by a MYB41 gene that has been mutated to encode an aspartate residue at amino acid 251, for example SEQ ID NO:13. In various embodiments, the MYB41 gene is from a dicot plant, such as, but not limited to, *Arabidopsis thaliana, Eutrema salsugineum*, or *Brassica napus*. Examples of such MYB41 genes are provided herein as SEQ ID NO:14 and SEQ ID NO:15. In other embodiments, the MYB41 gene is from a monocot plant, such as, but not limited to, a rice plant. Examples of such MYB41 genes are provided herein as SEQ ID NO:41, SEQ ID NO:42 and SEQ ID NO:43. In some embodiments the Casparian Strip is encoded by a MYB36 gene. In certain embodiments the MYB36 gene is from a dicot plant, such as, but not limited to, *Arabidopsis thaliana, Eutrema salsugineum*, or *Brassica napus*. Examples of such MYB36 genes are provided herein as SEQ ID NO:10, SEQ ID NO:11 and SEQ ID NO:12. In further embodiments the MYB36 gene is from a monocot plant, such as, but not limited to, a rice plant. Examples of such MYB36 genes are provided herein as SEQ ID NO:44, SEQ ID NO:45 and SEQ ID NO:46.

In certain embodiments the genetically encoded water filtering and transport components comprise an aquaporin. In some embodiments the aquaporin has been codon optimized for expression in the plant. In various embodiments the aquaporin is a plasma membrane intrinsic protein (PIP) or a tonoplast intrinsic membrane protein (TIP). In some embodiments the genetically encoded water filtering components comprise a plurality of distinct aquaporins. In further embodiments the genetically encoded water filtering components comprise a PIP and a TIP. In particular embodiments the PIP is from a dicot plant, such as, but not limited to, *Avicennia officinalis, Aegiceras corniculatum* or *Bruguiera gymnorrhiza*. Examples of such PIPs are provided herein as SEQ ID NO:1, SEQ ID NO:2, SEQ ID NO:3, SEQ ID NO:4 and SEQ ID NO:5. In certain embodiments the plasma membrane intrinsic protein is encoded by the is AoPIP1.2 gene from *Avicennia officinalis* (SEQ ID NO:1) or BgPIP2 from *Bruguiera gymnorrhiza* (SEQ ID NO:3). In further embodiments the PIP is from a monocot plant, such as, but not limited to, a rice plant. Rice has 11 known PIPs, which are contemplated for use in various embodiments of the present disclosure. In some embodiments the TIP gene is from a dicot plant, such as, but not limited to, *Bruguiera gymnorrhiza, Kandelia candel*, and *Eutrema salsugineum*. Examples of such TIPs are provided herein as SEQ ID NO:6, SEQ ID NO:7, SEQ ID NO:8 and SEQ ID NO:9. In other embodiments the TIP gene is TsTIP1.2 from *Eutrema salsugineum* (SEQ ID NO:6). In further embodiments the TIP is from a monocot plant, such as, but not limited to, a rice plant. Rice has 10 known TIPs, which are contemplated for use in various embodiments of the present disclosure.

In certain embodiments the genetically encoded physical barrier components and the genetically encoded water filtering and transport components are expressed by a root epidermal promoter. In some embodiments the root epidermal promoter is from a dicot plant, such as, but not limited to, *Arabidopsis thaliana*. Examples of such promoters are provided herein as SEQ ID NO:27 and SEQ ID NO:28. In further embodiments the root epidermal promoter is an ABC transporter promoter, a *CLAVATA*3/ESR-related 14 (CLE14) promoter, or an iron regulated transporter (IRT2) promoter from *Arabidopsis thaliana*. In other embodiments the root epidermal promoter is from a monocot plant, such as, but not limited to, a rice plant. Examples of such rice root epidermal promoters are provided herein as Os02g51110 (SEQ ID NO:34) and Os03g01700 (SEQ ID NO:35) promoters. In additional embodiments the root epidermal promoter is a synthetic promoter, including, but not limited to, synthetic promoter pSynEpiProm 1.0 4-block (SEQ ID NO:32) and synthetic promoter pSynEpiProm 1.0 7-block (SEQ ID NO:33).

In certain embodiments the genetically encoded water retention and pumping components comprise a mannitol biosynthesis protein and a mannitol transport protein. Examples of mannitol biosynthesis protein genes are provided herein as SEQ ID NO:20, SEQ ID NO:21, SEQ ID NO:24, SEQ ID NO:25 and SEQ ID NO:26. Examples of mannitol transport protein genes are provided herein as SEQ ID NO:16, SEQ ID NO:17, SEQ ID NO:18, SEQ ID NO:22 and SEQ ID NO:23. In further embodiments the mannitol biosynthesis protein gene and/or the mannitol transport protein gene is from a dicot plant, such as, but not limited to, *Arabidopsis thaliana, Daucus carota, Brassica napus, Olea europaea, Methanohalophilus portucalensis* or *Apium graveolens*. In some embodiments the mannitol biosynthesis protein is encoded by a mannose-6-phosphate reductase gene. In particular embodiments the mannose-6-phosphate reductase gene from *Apium graveolens* has been codon optimized for expression in the plant, for example the sequence provided herein as SEQ ID NO:19. In other embodiments the mannitol transport protein is encoded by a mannitol transporter gene. In certain embodiments the mannitol transporter gene from *Apium graveolens* has been codon optimized for expression in the plant, for example the sequence provided herein as SEQ ID NO:16. In some embodiments the genetically encoded water retention and pumping components are expressed by a parenchyma-specific promoter. In particular embodiments the parenchyma-specific promoter is from a dicot plant, such as, but not limited to, *Arabidopsis thaliana*. In further embodiments the parenchyma-specific promoter is an XCP1 promoter (SEQ ID NO:31), a VND7 promoter (SEQ ID NO:30) or a CESA7 promoter (SEQ ID NO:29) from *Arabidopsis thaliana*.

In certain embodiments of the present disclosure the plant is a monocot plant, such as, but not limited to, a rice, wheat, barley, oats, rye, sorghum or maize plant. In other embodiments of the present disclosure the plant is a dicot plant, such as, but not limited to, a soybean, alfalfa, sunflower, cotton, canola, sugar beet, sweet potato, tomato, strawberry, tobacco, banana, grape, cucurbits, pepper, beach plum, wax myrtle, mesquite, salt cedar, crossvine, withe vine, acacia, or laurel fig plant. In further embodiments the plant is able to grow in salt or sea water. In various embodiments the plant produces purified water when grown in salt or sea water.

The present disclosure also provides a plant part from a transgenic plant genetically engineered to produce purified water, comprising genetically encoded physical barrier components, genetically encoded water filtering and transport components, and genetically encoded water retention and pumping components, wherein the plant produces purified water when grown in water containing an impurity, and wherein at least one of the components is exogenously provided to the plant. In various embodiments the plant part is a cell, meristem, root, leaf, node, pistil, anther, flower, seed, embryo, stalk or petiole.

The present disclosure further provides a method of producing purified water from salt or sea water, comprising growing a transgenic plant genetically engineered to produce purified water, comprising genetically encoded physical barrier components, genetically encoded water filtering and transport components, and genetically encoded water retention and pumping components, wherein the plant produces purified water when grown in water containing an impurity, and wherein at least one of the components is exogenously provided to the plant, in salt of sea water and collecting the purified water produced by the plant.

The present disclosure additionally provides a nucleic acid construct, comprising genetically encoded physical barrier components, genetically encoded water filtering and transport components, and genetically encoded water retention and pumping components. In certain embodiments components a) through c) are separately comprised in a plurality of nucleic acid vectors. In other embodiments components a) through c) are comprised in a single vector. In various embodiments any of components a) through c) are operably linked to a termination sequence. In other embodiments all of components a) through c) are operably linked to a termination sequence. In some embodiments any of components a) through c) are operably linked to a transcriptional enhancer sequence. In further embodiments all of components a) through c) are operably linked to a transcriptional enhancer sequence.

BRIEF DESCRIPTION OF THE DRAWINGS

FIG. 2A. Root cross section from line TKK649-8-14, expressing the MYB36 gene under control of the epidermal ABCtrans promoter, and the omega enhancer to enhance translation. The natural endodermal and synthetic epidermal Casparian strips are visible. FIG. 2B. Root cross section from line KJM322, containing the pCASP promoter driving a CASP1_GFP marker gene for membrane localization of the Casparian strip. Only the natural endodermal Casparian strip is visible.

FIG. 3A. Root cross section from line KJM325-3. Image shows natural endodermal and engineered epidermal suberin. KJM325-3 has the MYB41 phospho-mimic gene under control of the ABCtrans epidermal promoter. FIG. 3B.

Root cross section of a wild type plant. Image shows no staining outside of the naturally occurring endodermal suberin.

Figure 4:
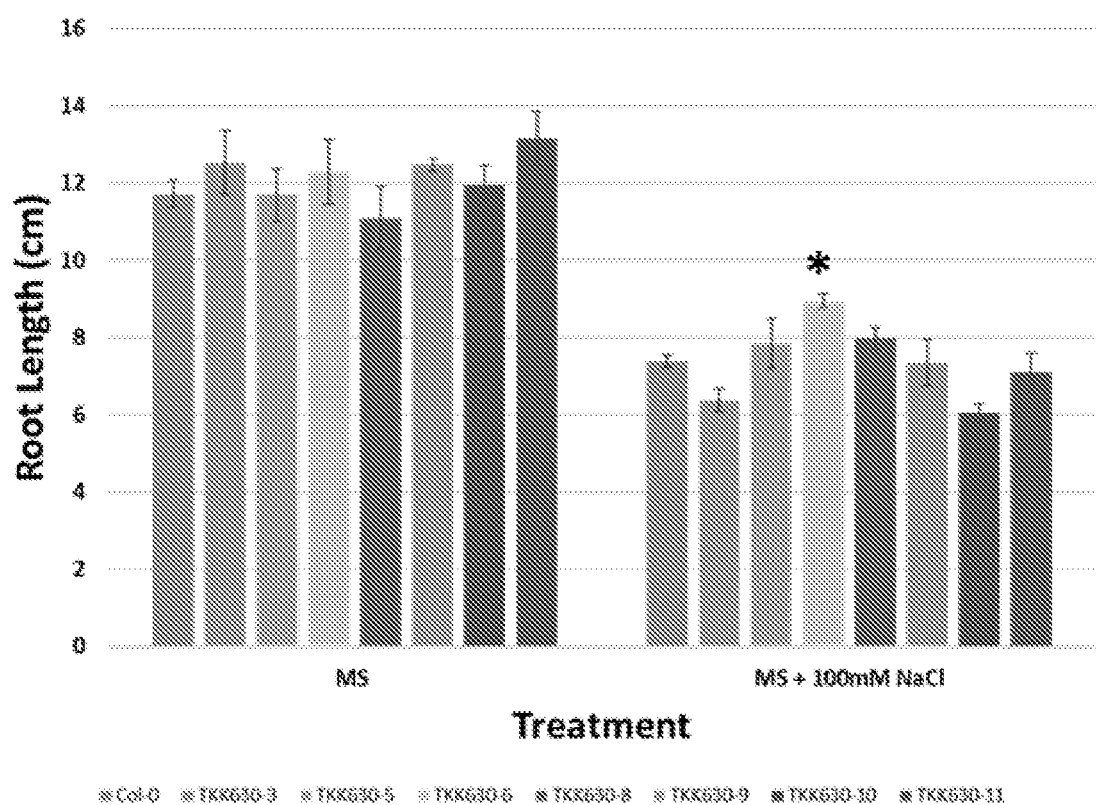

FIG. 4: Salt stress tolerance in T1 lines of TKK630, which has the mangrove PIP AoPIP1.2 expressed in the epidermis with the pABCtrans promoter. Root length was measured in lines grown in MS (left panel), and in MS plus 100 mM NaCl (right panel). Lines (from left to right) are Col-0, TKK630-3, TKK630-5, TKK630-6, TKK630-8, TKK630-9, TKK630-10 and TKK630-11.

Figure 5:
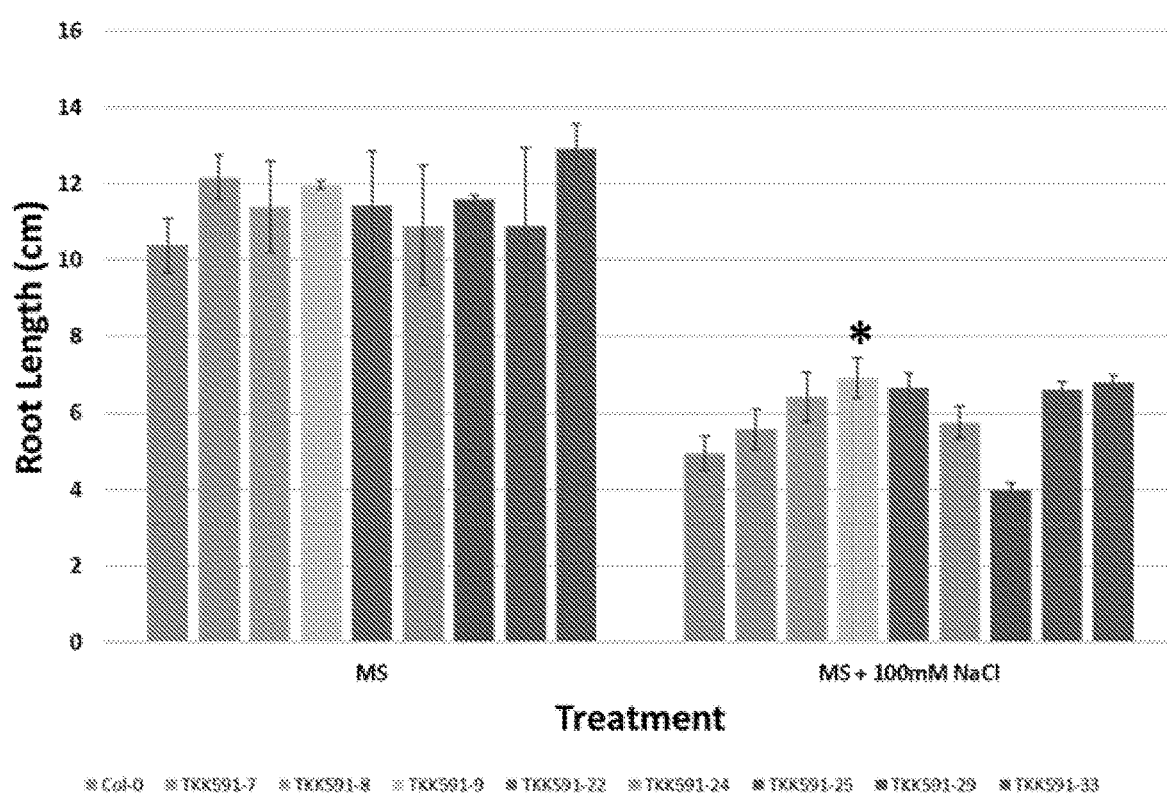

FIG. 5: Salt stress tolerance in T1 lines of TKK591, which has the mangrove PIP BgPIP2 expressed in the endodermis with the SCARECROW (SCR) promoter. Root length was measured in MS (left panel), and in MS plus 100 mM NaCl (right panel). Lines (from left to right) are Col 0, TKK591-7, TKK591-8, TKK591-9, TKK591-22, TKK591-24, TKK591-25, TKK591-29 and TKK591-33.

Figure 6:
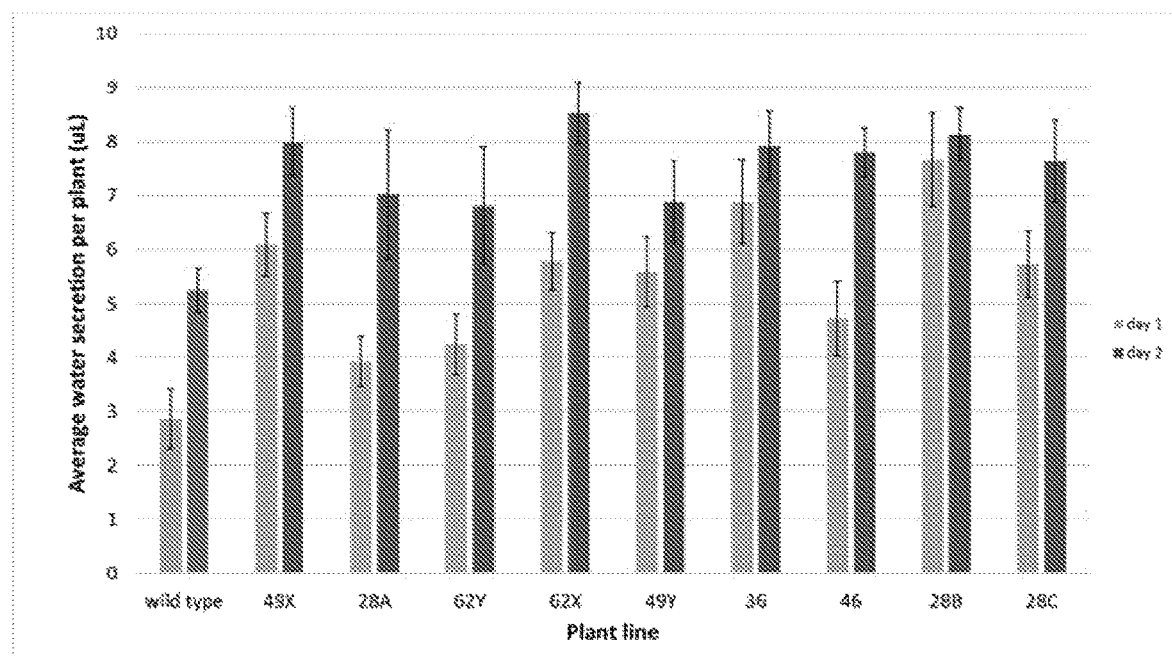

FIG. 6: Average water secretion per plant for wild type *Arabidopsis* and nine transgenic plant lines from transgenic line SGP105, which contains a gene for mannitol biosynthesis (mannose-6-phosphate-reductase (M6PR) under control of xylem promoter XCP1) and a gene for mannitol transport (MTR, under control of xylem promoter CESA7). Secreted water was collected from two healthy leaves each from ten plants per line and averaged per plant. Independent collections were made on two consecutive days. Data have been normalized on leaf area as calculated in ImageJ.

Figure 7A:
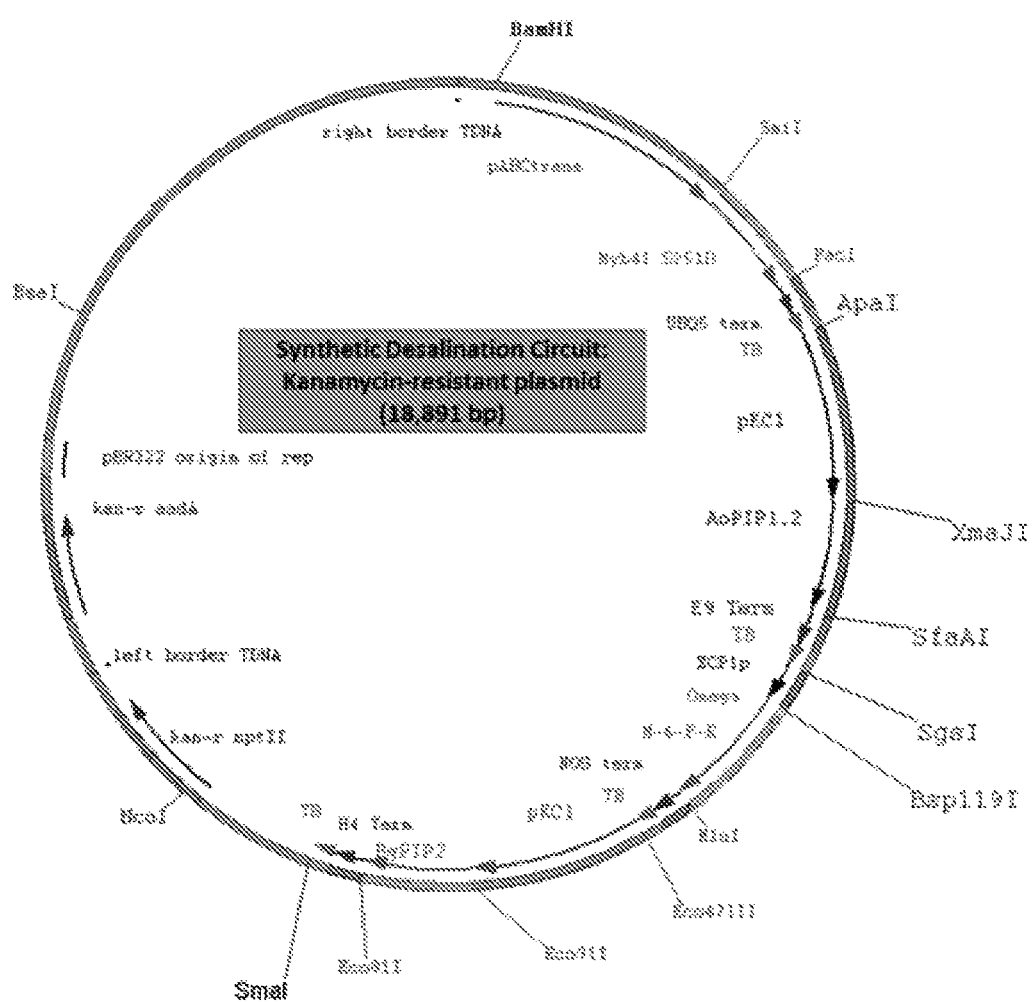
Figure 7B:
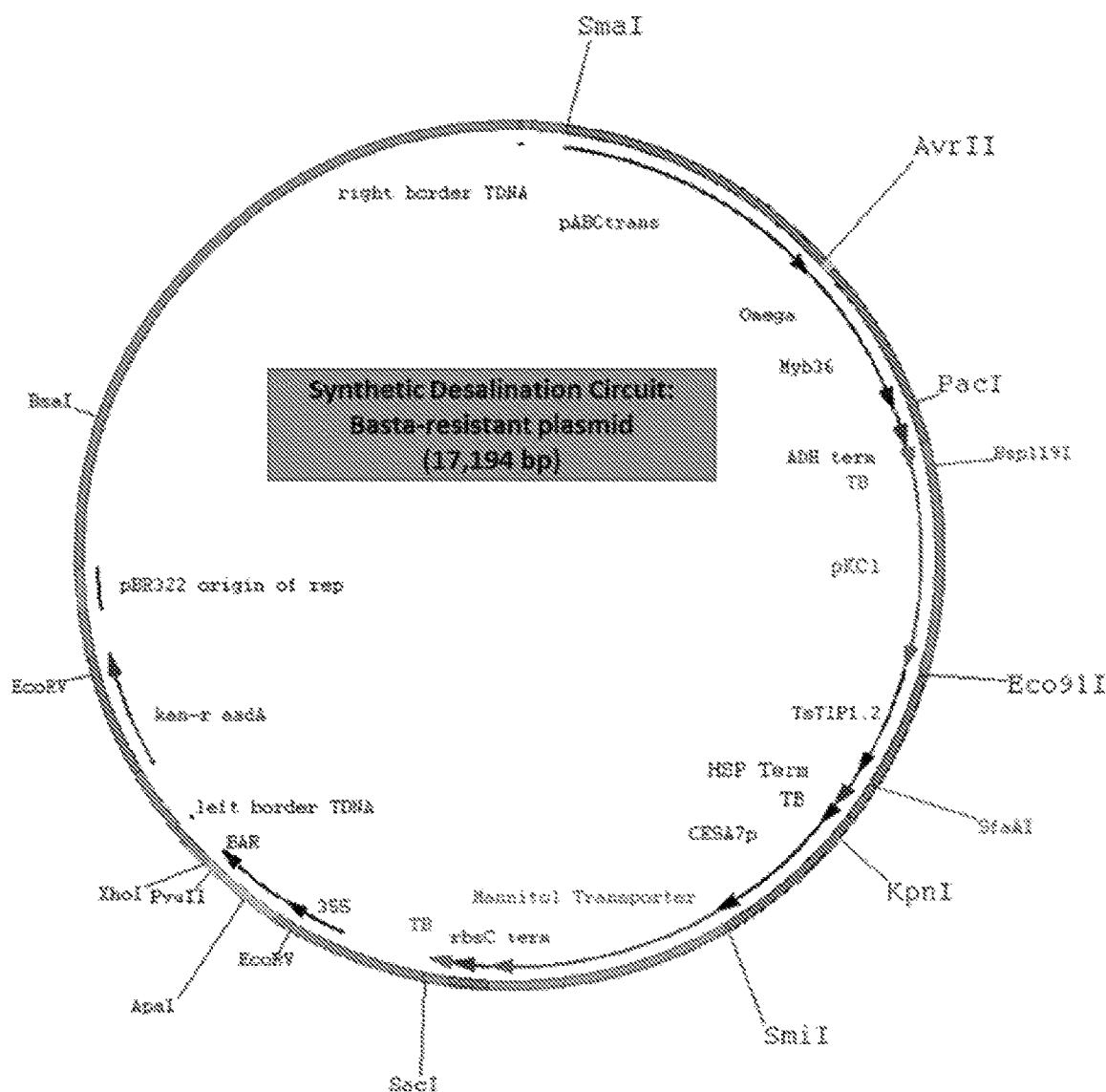

FIG. 7A and FIG. 7B: Two plasmids containing Version 1.0 of the complete synthetic desalination circuit. Because of the length of the full circuit (~19,000 kb) the genes have been divided between two plasmids, one that is Kanamycin-resistant (FIG. 7A) and one that is Basta resistant (FIG. 7B).

Figure 8:
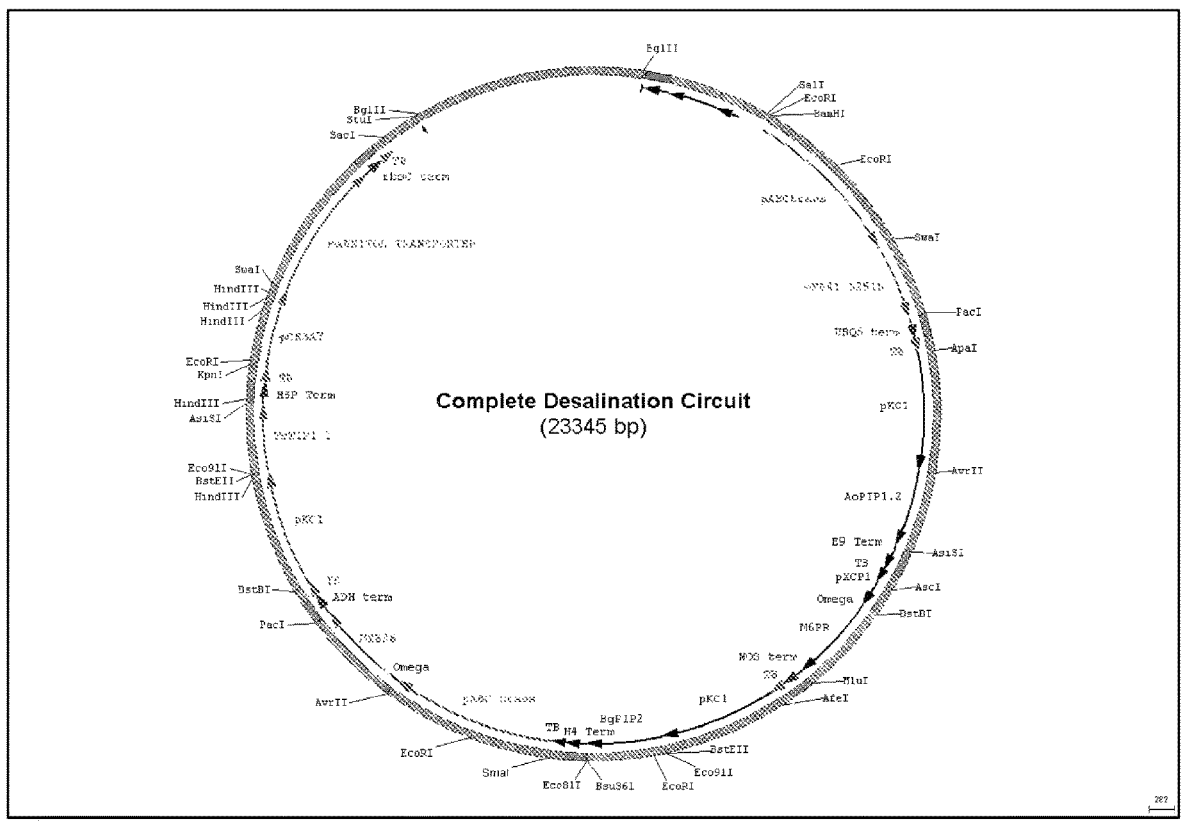

FIG. 8: The complete desalination gene circuit in one plant transformation plasmid. All individual components are insulated to prevent interference by upstream and downstream components with a specialized fragment, TB.

BRIEF DESCRIPTION OF THE SEQUENCES

SEQ ID NO:1: Aquaporin AoPIP1.2 from *Avicennia officinalis*, *Arabidopsis* codon optimized.
SEQ ID NO:2: Aquaporin AcPIP1 ortholog from *Aegiceras corniculatum*, *Arabidopsis* codon optimized.
SEQ ID NO:3: Aquaporin BgPIP2 from *Bruguiera gymnorrhiza*, *Arabidopsis* codon optimized.
SEQ ID NO:4: Aquaporin AcPIP2 ortholog from *Aegiceras corniculatum*, *Arabidopsis* codon optimized.
SEQ ID NO:5: Aquaporin AoPIP2 ortholog from *Avicennia officinalis*, *Arabidopsis* codon optimized.
SEQ ID NO:6: Aquaporin TsTIP1.2 from *Eutrema salsugineum*, *Arabidopsis* codon optimized.
SEQ ID NO:7: Aquaporin BgTIP ortholog from *Bruguiera gymnorrhiza*, *Arabidopsis* codon optimized.
SEQ ID NO:8: Aquaporin KcTIP ortholog from *Kandelia candel*, *Arabidopsis* codon optimized.
SEQ ID NO:9: Aquaporin TsTIP1.1 ortholog from *Eutrema salsugineum*, *Arabidopsis* codon optimized.
SEQ ID NO:10: Transcription factor AtMYB36 from *Arabidopsis thaliana*, for controlling production of water barrier.
SEQ ID NO:11: Transcription factor MYB36 ortholog from *Eutrema salsugineum*, for controlling production of water barrier.
SEQ ID NO:12: Transcription factor MYB36 ortholog from *Brassica napus*, for controlling production of water barrier.
SEQ ID NO:13: Transcription factor AtMYB41 S251D mutant from *Arabidopsis thaliana*, for controlling production of water barrier.
SEQ ID NO:14: Transcription factor MYB41-like ortholog from *Brassica napus*, for controlling production of water barrier.
SEQ ID NO:15: Transcription factor MYB41 ortholog from *Eutrema salsugineum*, for controlling production of water barrier.
SEQ ID NO:16: Mannitol transporter MaT2 (MTR) from *Apium graveolens*, *Arabidopsis* codon optimized.
SEQ ID NO:17: Mannitol transporter 1 ortholog from *Olea europaea*.
SEQ ID NO:18: Polyol transporter 5-like ortholog from *Daucus carota*.
SEQ ID NO:19: Mannose-6-phosphate reductase (M6PR) from *Apium graveolens*, *Arabidopsis* codon optimized.
SEQ ID NO:20: Putative NADPH dependent mannose 6-phosphate reductase ortholog from *Arabidopsis thaliana*.
SEQ ID NO:21: NADP-dependent D-sorbitol-6-phosphate dehydrogenase like ortholog from *Daucus carota*.
SEQ ID NO:22: AtPRO2 transporter (glycine betaine and proline transporter) from *Arabidopsis thaliana*.
SEQ ID NO:23: Proline transporter 2 ortholog from *Brassica napus*.
SEQ ID NO:24: Glycine Sarcosine N-methyltransferase (AtGSMT) from *Methanohalophilus portucalensis*, *Arabidopsis* codon optimized.
SEQ ID NO:25: Sarcosine Dimethylglycine N-Methyltransferase (AtSDMT) from *Methanohalophilus portucalensis*, *Arabidopsis* codon optimized.
SEQ ID NO:26: Delta 1-pyrroline-5-carboxylate synthase 1 (P5CS1) from *Arabidopsis thaliana*.
SEQ ID NO:27: pABC transporter promoter from *Arabidopsis thaliana*.
SEQ ID NO:28: pKC1 promoter from *Arabidopsis thaliana*.
SEQ ID NO:29: pCESA7 promoter from *Arabidopsis thaliana*.
SEQ ID NO:30: pVND7 promoter from *Arabidopsis thaliana*.
SEQ ID NO:31: pXCP1 promoter from *Arabidopsis thaliana*.
SEQ ID NO:32: Synthetic promoter pSynEpiProm 1.0 4-block.
SEQ ID NO:33: Synthetic promoter pSynEpiProm 1.0 7-block.
SEQ ID NO:34: Os02g51110 promoter from *Oryza sativa*.
SEQ ID NO:35: Os03g01700 promoter from *Oryza sativa*.
SEQ ID NO:36: 5'-UTR sequence AoPiP1.2 from *Oryza sativa*.
SEQ ID NO:37: 5'-UTR sequence Myb41 from *Oryza sativa*.
SEQ ID NO:38: 5'-UTR sequence BgPIP2 from *Oryza sativa*.
SEQ ID NO:39: 5'UTR sequence TsTIP1.2 from *Oryza sativa*.
SEQ ID NO:40: 5'UTR sequence Omega-Myb36 from *Oryza sativa*.
SEQ ID NO:41: Os07g37210.1 MYB41 homolog from *Oryza sativa*.
SEQ ID NO:42: Os04g50770.1 MYB41 homolog from *Oryza sativa*.
SEQ ID NO:43: Os02g46780.1 MYB41 homolog from *Oryza sativa*.

SEQ ID NO:44: Os08g15020.1 MYB36 homolog from *Oryza sativa*.
SEQ ID NO:45: Os01g49160.1 MYB36 homolog from *Oryza sativa*.
SEQ ID NO:46: Os01g09590.1 MYB36 homolog from *Oryza sativa*.

DETAILED DESCRIPTION

The present disclosure describes compositions and methods for removing salts and other impurities from water, for example removing NaCl from sea or salt water, and in filtering the entry of water into plants, provides a method to grow any and all types of crops, for example rice, under saline conditions.

Fresh water is an absolutely vital necessity for life on Earth. However, certain plants can actually live in salt water. Mangroves are land plants that live in salt water, tidal zones, hypersaline environments, and wetlands, and naturally desalinate seawater (Scholander, *Physiol. Plantarum* 21:251, 1968). Mangroves, as all land plants, must use pure water for life. However, mangroves retain the water that they desalinate (e.g., the vegetative portions of mangroves resemble desert plants).

The present disclosure provides a synthetic desalination gene circuit based, in part, on the natural processes used by mangroves that allow them to live in salt water. This gene circuit can be introduced into any plant species from model organisms in the laboratory to crop species to trees. Plants with this genetic circuit are able to filter 600 mM salt water (NaCl content greater than seawater, which is approximately 550 mM NaCl), and secrete pure water with ionic composition comparable to that of bottled water. As such, the presently described photosynthetically powered desalination system provides a pathway towards clean water for humanity and sustainable life on Earth. The design of the presently disclosed synthetic desalination circuit is based, in part, on how mangroves naturally desalinate sea water. This desalination ability is found in approximately 70 species of plants in 20 families. Therefore, the present desalination gene circuit takes advantage of the realization by the inventors that the desalination ability of mangroves likely involves adaptation and modification of natural plant features rather than independently evolving new desalination traits multiple times.

I. Recombinant DNA Molecules

As used herein, the term "nucleic acid" or "polynucleotide" refers to a single or double-stranded polymer of deoxyribonucleotide bases or ribonucleotide bases read from the 5' to the 3' end. A nucleic acid or polynucleotide may also optionally contain non-naturally occurring or altered nucleotide bases that permit correct read through by a polymerase and do not reduce expression of a polypeptide encoded by that nucleic acid. The terms "nucleotide sequence" or "nucleic acid sequence" refer to both the sense and antisense strands of a nucleic acid as either individual single strands or in the duplex. The term "ribonucleic acid" (RNA) is inclusive of RNAi (inhibitory RNA), dsRNA (double stranded RNA), siRNA (small interfering RNA), mRNA (messenger RNA), miRNA (micro-RNA), tRNA (transfer RNA, whether charged or discharged with a corresponding acylated amino acid), and cRNA (complementary RNA). The words "nucleic acid fragment," "nucleotide sequence fragment", or more generally "fragment" will be understood by those in the art as a functional term that includes genomic sequences, ribosomal RNA sequences, transfer RNA sequences, messenger RNA sequences, operon sequences, and smaller engineered nucleotide sequences that express or may be adapted to express, proteins, polypeptides or peptides. The nomenclature used herein is that required by Title 37 of the United States Code of Federal Regulations § 1.822 and set forth in the tables in WIPO Standard ST.25 (1998), Appendix 2, Tables 1 and 3.

As used herein, the terms "nucleic acid" and "polynucleotide" thus refer to a deoxyribonucleotide, ribonucleotide, or a mixed deoxyribonucleotide and ribonucleotide polymer in either single- or double-stranded form, and unless otherwise limited, would encompass known analogs of natural nucleotides that can function in a similar manner as naturally-occurring nucleotides. The polynucleotide sequences include the DNA strand sequence that is transcribed into RNA and the strand sequence that is complementary to the DNA strand that is transcribed. The polynucleotide sequences also include both full-length sequences as well as shorter sequences derived from the full-length sequences. Allelic variations of the exemplified sequences also fall within the scope of the present disclosure. The polynucleotide sequence includes both the sense and antisense strands either as individual strands or in the duplex.

As used herein, the term "recombinant nucleic acid," "recombinant polynucleotide" or "recombinant DNA molecule" refers to a polynucleotide that has been altered from its native state, such as by linkage to one or more other polynucleotide sequences to which the recombinant polynucleotide molecule is not normally linked to in nature. Such molecules may or may not be present, for example, in a host genome or chromosome.

The present disclosure further provides polynucleotides that are complementary in sequence to the polynucleotides disclosed herein. Polynucleotides and polypeptides of the disclosure can be provided in purified or isolated form.

The subject disclosure also concerns oligonucleotide probes and primers, such as polymerase chain reaction (PCR) primers, that can hybridize to a coding or non-coding sequence of a polynucleotide of the present disclosure. Oligonucleotide probes of the disclosure can be used in methods for detecting and quantitating nucleic acid sequences encoding the polypeptides of the disclosure. Oligonucleotide primers of the disclosure can be used in PCR methods and other methods involving nucleic acid amplification. In a preferred embodiment, a probe or primer of the disclosure can hybridize to a polynucleotide of the disclosure under stringent conditions. Probes and primers of the disclosure can optionally comprise a detectable label or reporter molecule, such as fluorescent molecules, enzymes, radioactive moiety (e.g., $^3$H, $^{35}$S, $^{125}$I, etc.), and the like. Probes and primers of the disclosure can be of any suitable length for the method or assay in which they are being employed. Typically, probes and primers of the disclosure will be 10 to 500 or more nucleotides in length. Probes and primers that are 10 to 20, 21 to 30, 31 to 40, 41 to 50, 51 to 60, 61 to 70, 71 to 80, 81 to 90, 91 to 100 or more nucleotides in length are contemplated within the scope of the disclosure. Probes and primers of the disclosure can have complete (100%) nucleotide sequence identity with the polynucleotide sequence, or the sequence identity can be less than 100%. For example, sequence identity between a probe or primer and a sequence can be 99%, 98%, 97%, 96%, 95%, 90%, 85%, 80%, 75%, 70% or any other percentage sequence identity allowing the probe or primer to hybridize under stringent conditions to a nucleotide sequence of a polynucleotide of the disclosure. In one embodiment, a probe or primer of the disclosure has 70% or greater, 75% or greater, 80% or greater, 85% or greater, 90% or greater, or 95% to 100% sequence identity with a nucleotide sequence provided herein, including the complement thereof.

Because of the degeneracy of the genetic code, a variety of different polynucleotide sequences can encode polypeptides or mutant polypeptides disclosed herein. All possible triplet codons (and where U also replaces T) and the amino acid encoded by each codon is well-known in the art. In addition, it is well within the capability of one of skill in the art to create alternative polynucleotide sequences encoding the same, or essentially the same, mutant polypeptides of the subject disclosure. These variant or alternative polynucleotide sequences are within the scope of the subject disclosure. As used herein, references to "essentially the same" sequence refers to sequences that encode amino acid substitutions, deletions, additions, or insertions that do not materially alter the functional activity of the polypeptide encoded by the polynucleotides of the present disclosure. Allelic variants of the nucleotide sequences encoding a wild-type or mutant polypeptide of the present disclosure are also encompassed within the scope of the disclosure.

Amino acids can be generally categorized in the following classes: non-polar, uncharged polar, basic, and acidic. Conservative substitutions whereby a polypeptide of the present disclosure having an amino acid of one class is replaced with another amino acid of the same class fall within the scope of the subject disclosure so long as the polypeptide having the substitution still retains substantially the same functional activity as the polypeptide that does not have the substitution. Functional activity may be determined as set forth in the Examples section below. Polynucleotides encoding a polypeptide having one or more amino acid substitutions in the sequence are contemplated within the scope of the present disclosure.

Table 1 provides a listing of examples of amino acids belonging to each class.

TABLE 1

Classes of Amino Adds

| | |
|---|---|
| Nonpolar | Ala, Val, Leu, Ile, Pro, Met, Phe, Trp, Gly, Cys |
| Uncharged Polar | Gly, Ser, Thr, Cys, Tyr, Asn, Gln |
| Acidic | Asp, Glu |
| Basic | Lys, Arg, His |

Glycine and cysteine are understood in the art to fall in both the nonpolar and uncharged polar classes. Substitution of amino acids other than those specifically exemplified or naturally present in the disclosed polypeptides are also contemplated within the scope of the present disclosure. For example, non-natural amino acids can be substituted for the amino acids of a polypeptide, so long as the polypeptide having the substituted amino acids retains substantially the same functional activity as the polypeptide in which amino acids have not been substituted. Examples of non-natural amino acids include, but are not limited to, ornithine, citrulline, hydroxyproline, homoserine, phenylglycine, taurine, iodotyrosine, 2,4-diaminobutyric acid, α-amino isobutyric acid, 4-aminobutyric acid, 2-amino butyric acid, γ-amino butyric acid, e-amino hexanoic acid, 6-amino hexanoic acid, 2-amino isobutyric acid, 3-amino propionic acid, norleucine, norvaline, sarcosine, homocitrulline, cysteic acid, t-butylglycine, t-butylalanine, phenylglycine, cyclohexylalanine, β-alanine, fluoro-amino acids, designer amino acids such as β-methyl amino acids, C-methyl amino acids, N-methyl amino acids, and amino acid analogues in general. Non-natural amino acids also include amino acids having derivatized side groups. Furthermore, any of the amino acids in the disclosed proteins or polypeptides can be of the D (dextrorotary) form or L (levorotary) form. Allelic variants of the disclosed polypeptides are also encompassed within the scope of the disclosure.

As used herein, "wild-type" means naturally occurring. A "wild-type DNA molecule," "wild-type protein" is a naturally occurring version of a DNA molecule or protein, that is, a version of a DNA molecule or protein pre-existing in nature. A wild-type version of a DNA molecule or protein may be useful for comparison with a recombinant or engineered DNA molecule or protein.

II. Methods of Modifying Nucleic Acids and Proteins

The subject disclosure also concerns variants of the polynucleotides of the present disclosure that encode functional polypeptides of the disclosure. Variant sequences include those sequences wherein one or more nucleotides of the sequence have been substituted, deleted, and/or inserted. The nucleotides that can be substituted for natural nucleotides of DNA have a base moiety that can include, but is not limited to, inosine, 5-fluorouracil, 5-bromouracil, hypoxanthine, 1-methylguanine, 5-methylcytosine, and tritylated bases. The sugar moiety of the nucleotide in a sequence can also be modified and includes, but is not limited to, arabinose, xylulose, and hexose. In addition, the adenine, cytosine, guanine, thymine, and uracil bases of the nucleotides can be modified with acetyl, methyl, and/or thio groups. Sequences containing nucleotide substitutions, deletions, and/or insertions can be prepared and tested using standard techniques known in the art.

As used herein, the term "percent sequence identity" or "percent identity" refers to the percentage of identical nucleotides in a linear polynucleotide sequence of a reference ("query") polynucleotide molecule (or its complementary strand) as compared to a test ("subject") polynucleotide molecule (or its complementary strand), or a linear polypeptide sequence of a reference polypeptide molecule as compared to a test polypeptide molecule, when the two sequences are optimally aligned (with appropriate nucleotide or amino acid insertions, deletions, or gaps totaling less than 20 percent of the reference sequence over the window of comparison). Optimal alignment of sequences for aligning a comparison window are well known to those skilled in the art and may be conducted by tools such as the local homology algorithm of Smith and Waterman, the homology alignment algorithm of Needleman and Wunsch, the search for similarity method of Pearson and Lipman, and preferably by computerized implementations of these algorithms such as GAP, BESTFIT, FASTA, and TFASTA available as part of the GCG® Wisconsin Package® (Accelrys Inc., Burlington, Mass.). Polynucleotides and polypeptides contemplated within the scope of the subject disclosure can also be defined in terms of identity and/or similarity ranges with those sequences of the disclosure specifically exemplified herein. In certain embodiments, the disclosure provides polypeptide sequences having at least about 70, 75, 80, 85, 90, 95, 96, 97, 98, 99, or 99.5 percent identity to a polypeptide sequences provided herein, including, but not limited to, those encoded by SEQ ID NOs:1-26. In certain embodiments, the disclosure provides polynucleotide sequences having at least about 70, 75, 80, 85, 90, 95, 96, 97, 98, 99, or 99.5 percent identity to a polynucleotide sequence provided herein, including, but not limited to, SEQ ID NOs:1-40. In addition to the nucleotide and amino acid sequences disclosed herein, homologous nucleic acid and amino acid sequences ("homologs") from other species are also contemplated for use in certain embodiments.

In certain embodiments, the disclosure provides polynucleotides encoding polypeptides comprising the amino acid sequence provided herein, or a fragment or variant thereof. In certain embodiments, the polynucleotides encode polypeptides comprising a variant or mutant of the amino acid sequence provided herein, or combinations, fragments, or variants thereof.

Fragments and variants of a mutant polypeptide of the present disclosure can be generated as described herein and tested for the presence of enzymatic activity as described herein, or using other standard techniques known in the art. Thus, an ordinarily skilled artisan can readily prepare and test fragments and variants of a mutant polypeptide of the disclosure and determine whether the fragment or variant retains functional activity relative to full-length or a non-variant mutant polypeptide. Fragments and variants of mutant polypeptides can be tested for activity, for example using methods disclosed herein or by other methods well-known in the art.

In certain embodiments, polypeptides of the disclosure, and functional peptide fragments thereof, can be used to generate antibodies that bind specifically to a polypeptide of the disclosure, and such antibodies are contemplated within the scope of the disclosure. The antibodies of the disclosure can be polyclonal or monoclonal and can be produced and isolated using standard methods known in the art.

Polypeptide fragments according to the disclosure typically comprise a contiguous span of at least about 20, about 25, about 30, about 35, about 40 or about 45 amino acids of a sequence disclosed herein, including, but not limited to, those encoded by SEQ ID NOs:1-26. In certain embodiments, polypeptide fragments comprise about 50, about 100, about 150, about 200, about 250, about 300, about 350, about 400 or about 450 amino acids of a sequence provided herein.

Fragments of a polypeptide of the disclosure can be obtained by cleaving the polypeptides of the disclosure with a proteolytic enzyme (such as trypsin, chymotrypsin, or collagenase) or with a chemical reagent, such as cyanogen bromide (CNBr). Alternatively, peptide or polypeptide fragments can be generated in a highly acidic environment, for example at pH 2.5. Peptide or polypeptide fragments can also be prepared by chemical synthesis or using host cells transformed with an expression vector comprising a polynucleotide encoding a fragment of a polypeptide of the disclosure, for example, a mutant polypeptide that is a fragment of an amino acid sequence provided herein.

III. Expression Constructs

Polynucleotides useful in the present disclosure can be provided in an expression construct. Expression constructs of the disclosure generally include regulatory elements that are functional in the intended host cell in which the expression construct is to be expressed. Thus, a person of ordinary skill in the art can select regulatory elements for use in bacterial host cells, yeast host cells, plant host cells, insect host cells, mammalian host cells, and human host cells. Regulatory elements include promoters, transcription termination sequences, translation termination sequences, enhancers, and polyadenylation elements. As used herein, the term "expression construct" refers to one or a combination of nucleic acid sequences that provides for transcription of an operably linked nucleic acid sequence. As used herein, "operably linked" means two DNA molecules linked in manner so that one may affect the function of the other. Operably-linked DNA molecules may be part of a single contiguous molecule and may or may not be adjacent. For example, a promoter is operably linked with a polypeptide-encoding DNA molecule in a DNA construct where the two DNA molecules are so arranged that the promoter may affect the expression of the DNA molecule.

As used herein, the term "heterologous" refers to the relationship between two or more items derived from different sources and thus not normally associated in nature. For example, a protein-coding recombinant DNA molecule is heterologous with respect to an operably linked promoter if such a combination is not normally found in nature. In addition, a particular recombinant DNA molecule may be heterologous with respect to a cell, seed, or organism into which it is inserted when it would not naturally occur in that particular cell, seed, or organism.

The term "transgene" refers to a DNA molecule artificially incorporated into the genome of an organism as a result of human intervention, such as by plant transformation methods. As used herein, the term "transgenic" means comprising a transgene, for example a "transgenic plant" refers to a plant comprising a transgene in its genome and a "transgenic trait" refers to a characteristic or phenotype conveyed or conferred by the presence of a transgene incorporated into the plant genome. As a result of such genomic alteration, the transgenic plant is something distinctly different from the related wild-type plant and the transgenic trait is a trait not naturally found in the wild-type plant. Transgenic plants of the present disclosure comprise the recombinant DNA molecules and proteins provided herein.

An expression construct of the disclosure can comprise a promoter sequence operably linked to a polynucleotide sequence encoding a modified polypeptide of the disclosure. Promoters can be incorporated into a polynucleotide using standard techniques known in the art. Multiple copies of promoters or multiple promoters can be used in an expression construct of the disclosure. In a preferred embodiment, a promoter can be positioned about the same distance from the transcription start site in the expression construct as it is from the transcription start site in its natural genetic environment. Some variation in this distance is permitted without substantial decrease in promoter activity. A transcription start site is typically included in the expression construct.

Embodiments of the disclosure further provide a recombinant DNA molecule encoding a polypeptide, wherein the recombinant DNA molecule is further defined as operably linked to a heterologous regulatory element. In specific embodiments, the heterologous regulatory element is a promoter functional in a plant cell. In further embodiments, the promoter is an inducible or root specific promoter.

If the expression construct is to be provided in or introduced into a plant cell, then plant viral promoters, such as, for example, a cauliflower mosaic virus (CaMV) 35S (including the enhanced CaMV 35S promoter (see, e.g., U.S. Pat. No. 5,106,739)), a CaMV 19S promoter or a cassava vein mosaic virus promoter can be used. Other promoters that can be used for expression constructs in plants include, but are not limited to, zein promoters including maize zein promoters, prolifera promoter, Ap3 promoter, heat shock promoters, T-DNA 1'- or 2'-promoter of *A. tumefaciens*, polygalacturonase promoter, chalcone synthase A (CHS-A) promoter from *petunia*, tobacco PR-1a promoter, ubiquitin promoter, actin promoter, alcA gene promoter, pin2 promoter (Xu, et al., *Plant Mol. Biol.* 22:573-588, 1993), maize WipI promoter, maize trpA gene promoter (U.S. Pat. No. 5,625,136), maize CDPK gene promoter, and RUBISCO SSU promoter (U.S. Pat. No. 5,034,322) can also be used. Constitutive promoters (such as the CaMV, ubiquitin, actin, or NOS promoter), developmentally-regulated promoters, and inducible promoters (such as those promoters than can be induced by heat, light, hormones, or chemicals) are also contemplated for use with polynucleotide expression constructs of the disclosure.

Expression constructs of the disclosure may optionally contain a transcription termination sequence, a translation termination sequence, a sequence encoding a signal peptide, and/or enhancer elements. Transcription termination regions can typically be obtained from the 3' untranslated region of a eukaryotic or viral gene sequence. Transcription termination sequences can be positioned downstream of a coding sequence to provide for efficient termination. A signal peptide sequence is a short amino acid sequence typically present at the amino terminus of a protein that is responsible for the relocation of an operably linked mature polypeptide to a wide range of post-translational cellular destinations, ranging from a specific organelle compartment to sites of protein action and the extracellular environment. Targeting gene products to an intended cellular and/or extracellular destination through the use of an operably linked signal peptide sequence is contemplated for use with the polypeptides of the disclosure. Classical enhancers are cis-acting elements that increase gene transcription and can also be included in the expression construct. Classical enhancer elements are known in the art, and include, but are not limited to, the CaMV 35S enhancer element, cytomegalovirus (CMV) early promoter enhancer element, and the SV40 enhancer element. Intron-mediated enhancer elements that enhance gene expression are also known in the art. These elements should be present within the transcribed region and are orientation dependent. Examples include the maize shrunken-1 enhancer element (Clancy and Hannah, *Plant Physiol.* 130:918-929, 2002). Expression constructs may optionally contain a 5'-untranslated region (5'-UTR), as described in further detail below.

IV. Transformation Methods

One aspect of the disclosure includes plant cells, plant tissues, plants, and seeds that comprise the recombinant DNA provided by the disclosure. Suitable methods for transformation of host plant cells for use with the current disclosure include virtually any method by which DNA can be introduced into a cell (for example, where a recombinant DNA construct is stably integrated into a plant chromosome) and are well-known in the art. For example, by direct delivery of DNA such as by PEG-mediated transformation of protoplasts, by desiccation/inhibition-mediated DNA uptake, by electroporation (U.S. Pat. No. 5,384,253, specifically incorporated herein by reference in its entirety), or by agitation with silicon carbide fibers (U.S. Pat. Nos. 5,302,523 and 5,464,765, both specifically incorporated herein by reference in its entirety).

Two effective methods for cell transformation are *Agrobacterium*-mediated transformation and microprojectile bombardment-mediated transformation. Microprojectile bombardment methods are illustrated, for example, in U.S. Pat. Nos. 5,550,318, 5,538,880, 6,160,208, and 6,399,861. *Agrobacterium*-mediated transformation methods are described, for example in U.S. Pat. No. 5,591,616. Transformation of plant material is practiced in tissue culture on nutrient media, for example a mixture of nutrients that allow cells to grow in vitro. Recipient cell targets include, but are not limited to, meristem cells, shoot tips, hypocotyls, calli, immature or mature embryos, and gametic cells such as microspores and pollen. Callus can be initiated from tissue sources including, but not limited to, immature or mature embryos, hypocotyls, seedling apical meristems, microspores and the like. Cells containing a transgenic nucleus are grown into transgenic plants.

In transformation, DNA is typically introduced into only a small percentage of target plant cells in any one transformation experiment. Marker genes are typically used to provide an efficient system for identification of those cells that are stably transformed by receiving and integrating a recombinant DNA molecule into their genomes. Preferred marker genes provide selective markers which confer resistance to a selective agent, such as an antibiotic or an herbicide. Any of the herbicides to which plants of this disclosure can be resistant is an agent for selective markers. Potentially transformed cells are exposed to the selective agent. In the population of surviving cells are those cells where, generally, the resistance-conferring gene is integrated and expressed at sufficient levels to permit cell survival. Cells can be tested further to confirm stable integration of the exogenous DNA. Commonly used selective marker genes include those conferring resistance to antibiotics such as kanamycin and paromomycin (nptII), hygromycin B (aph IV), spectinomycin (aadA) and gentamycin (aac3 and aacC4) or resistance to herbicides such as glufosinate (bar or pat), dicamba (DMO) and glypho sate (aroA or EPSPS). Examples of such selectable markers are illustrated in U.S. Pat. Nos. 5,550,318, 5,633,435, 5,780,708 and 6,118,047. Markers that provide an ability to visually screen transformants can also be employed, for example, a gene expressing a colored or fluorescent protein such as a luciferase or green fluorescent protein (GFP) or a gene expressing a beta-glucuronidase or uidA gene (GUS) for which various chromogenic substrates are known.

The present disclosure provides methods and constructs for regenerating a plant from a cell with modified genomic DNA resulting from genome editing. The regenerated plant can then be used to propagate additional plants. The disclosure thus provides plants produced by the methods disclosed herein. Plants of the present disclosure may be monocots or dicots, and may include, for example, rice, wheat, barley, oats, rye, sorghum, maize, soybean, alfalfa, sunflower, cotton, canola, sugar beet, sweet potato, tomato, strawberry, tobacco, banana, grape, curcubits and pepper plants, and may also include coastal woody shrub and vine species, such as beach plum, wax myrtle, mesquite, salt cedar, crossvine, with vine, acacia and laurel.

V. Breeding Plants of the Disclosure

In addition to direct transformation of a particular plant genotype with a construct prepared according to the current disclosure, transgenic plants may be made by crossing a plant having a selected DNA of the disclosure to a second plant lacking the construct. For example, a selected coding sequence can be introduced into a particular plant variety by crossing, without the need for ever directly transforming a plant of that given variety. Therefore, the current disclosure not only encompasses a plant directly transformed or regenerated from cells which have been transformed in accordance with the current disclosure, but also the progeny of such plants. As used herein, the term "progeny" denotes the offspring of any generation of a parent plant prepared in accordance with the instant disclosure, wherein the progeny comprises a selected DNA construct prepared in accordance with the disclosure. "Crossing" a plant to provide a plant line having one or more added transgenes relative to a starting plant line, as disclosed herein, is defined as the techniques that result in a transgene of the disclosure being introduced into a plant line by crossing a plant of a starting line with a plant of a donor plant line that comprises a transgene of the disclosure. To achieve this one could, for example, perform the following steps: (a) plant seeds of the first (starting line) and second (donor plant line that comprises a transgene of the disclosure) parent plants; (b) grow the seeds of the first and second parent plants into plants that bear flowers; (c) pollinate a flower from the first parent plant with pollen from the second parent plant; and (d) harvest seeds produced on the parent plant bearing the fertilized flower. Backcrossing is herein defined as the process including the steps of: (a) crossing a plant of a first genotype containing a desired gene, DNA sequence or element to a plant of a second genotype lacking the desired gene, DNA sequence or element; (b) selecting one or more progeny plant containing the desired gene, DNA sequence or element; (c) crossing the progeny plant to a plant of the second genotype; and (d) repeating steps (b) and (c) for the purpose of transferring a desired DNA sequence from a plant of a first genotype to a plant of a second genotype.

Introgression of a DNA element into a plant genotype is defined as the result of the process of backcross conversion. A plant genotype into which a DNA sequence has been introgressed may be referred to as a backcross converted genotype, line, inbred, or hybrid. Similarly, a plant genotype lacking the desired DNA sequence may be referred to as an unconverted genotype, line, inbred, or hybrid.

VI. Genome Editing

Targeted modification of plant genomes through the use of genome editing methods can be used to create improved mutant or transgenic plant lines through modification or insertion of plant genomic DNA. In addition, genome editing methods can enable targeted insertion of multiple nucleic acids of interest (a trait stack) into a plant genome. As used herein "site-directed integration" refers to genome editing methods the enable targeted insertion of one or more nucleic acids of interest into a plant genome. Suitable methods for altering a wild-type DNA sequence or a pre-existing transgenic sequence or for inserting DNA into a plant genome at a pre-determined chromosomal site include any method known in the art. Exemplary methods include the use of sequence specific nucleases, such as zinc-finger nucleases, engineered or native meganucleases, TALE-endonucleases, or an RNA-guided endonucleases (for example, a Clustered Regularly Interspersed Short Palindromic Repeat (CRISPR)/Cas9 system, a CRISPR/Cpf1 system, a CRISPR/CasX system, a CRISPR/CasY system, a CRISPR/Cascade system). Several embodiments relate to methods of genome editing by using single-stranded oligonucleotides to introduce precise base pair modifications in a plant genome, as described by Sauer et al., *Plant Physiology* 170(4):1917-1928 (2016). Methods of genome editing to modify, delete, or insert nucleic acid sequences into genomic DNA are known in the art. In the present disclosure, such methodology can be used to redirect expression of the MYB36 and MYB41 genes by altering the promoter sequences. Likewise, the coding sequences of the PIPs and TIPs can be modified, and the promoters altered for root expression as defined herein. In a similar fashion, the expression of the osmoticum biosynthesis and transporter genes can be redirected to xylem parenchyma by modification of the promoter sequences.

Several embodiments may therefore relate to a recombinant DNA construct comprising an expression cassette(s) encoding a site-specific nuclease and, optionally, any associated protein(s) to carry out genome modification. These nuclease-expressing cassette(s) may be present in the same molecule or vector as a donor template for templated editing or an expression cassette comprising nucleic acid sequence encoding a protein as described herein (in cis) or on a separate molecule or vector (in trans). Several methods for site-directed integration are known in the art involving different sequence-specific nucleases (or complexes of proteins or guide RNA or both) that cut the genomic DNA to produce a double strand break (DSB) or nick at a desired genomic site or locus. As understood in the art, during the process of repairing the DSB or nick introduced by the nuclease enzyme, the donor template DNA, transgene, or expression cassette may become integrated into the genome at the site of the DSB or nick. The presence of the homology arm(s) in the DNA to be integrated may promote the adoption and targeting of the insertion sequence into the plant genome during the repair process through homologous recombination, although an insertion event may occur through non-homologous end joining (NHEJ). As used herein, the term "double-strand break inducing agent" refers to any agent that can induce a double-strand break (DSB) in a DNA molecule. In some embodiments, the double-strand break inducing agent is a site-specific genome modification enzyme.

As used herein, the term "site-specific genome modification enzyme" refers to any enzyme that can modify a nucleotide sequence in a sequence-specific manner. In some embodiments, a site-specific genome modification enzyme modifies the genome by inducing a single-strand break. In some embodiments, a site-specific genome modification enzyme modifies the genome by inducing a double-strand break. In some embodiments, a site-specific genome modification enzyme comprises a cytidine deaminase. In some embodiments, a site-specific genome modification enzyme comprises an adenine deaminase. In the present disclosure, site-specific genome modification enzymes include endonucleases, recombinases, transposases, deaminases, helicases and any combination thereof. In some embodiments, the site-specific genome modification enzyme is a sequence-specific nuclease.

In one aspect, the endonuclease is selected from a meganuclease, a zinc-finger nuclease (ZFN), a transcription activator-like effector nucleases (TALEN), an Argonaute (non-limiting examples of Argonaute proteins include *Thermus thermophilus* Argonaute (TtAgo), *Pyrococcus furiosus* Argonaute (PfAgo), *Natronobacterium gregoryi* Argonaute (NgAgo), an RNA-guided nuclease, such as a CRISPR associated nuclease (non-limiting examples of CRISPR associated nucleases include Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, Cpf1, CasX, CasY, homologs thereof, or modified versions thereof).

In some embodiments, the site-specific genome modification enzyme is a recombinase. Non-limiting examples of recombinases include a tyrosine recombinase attached to a DNA recognition motif provided herein is selected from the group consisting of a Cre recombinase, a Gin recombinase, a Flp recombinase, and a Tnp1 recombinase. In an aspect, a Cre recombinase or a Gin recombinase provided herein is tethered to a zinc-finger DNA-binding domain, or a TALE DNA-binding domain, or a Cas9 nuclease. In another aspect, a serine recombinase attached to a DNA recognition motif provided herein is selected from the group consisting of a PhiC31 integrase, an R4 integrase, and a TP-901 integrase. In another aspect, a DNA transposase attached to a DNA binding domain provided herein is selected from the group consisting of a TALE-piggyBac and TALE-Mutator.

Any DNA of interest provided herein can be integrated into a target site of a chromosome sequence by introducing the DNA of interest and the provided site-specific genome modification enzymes. Any method provided herein can utilize any site-specific genome modification enzyme provided herein.

EXAMPLES

Example 1: Components of the Desalination Gene Circuit

Figure 1:
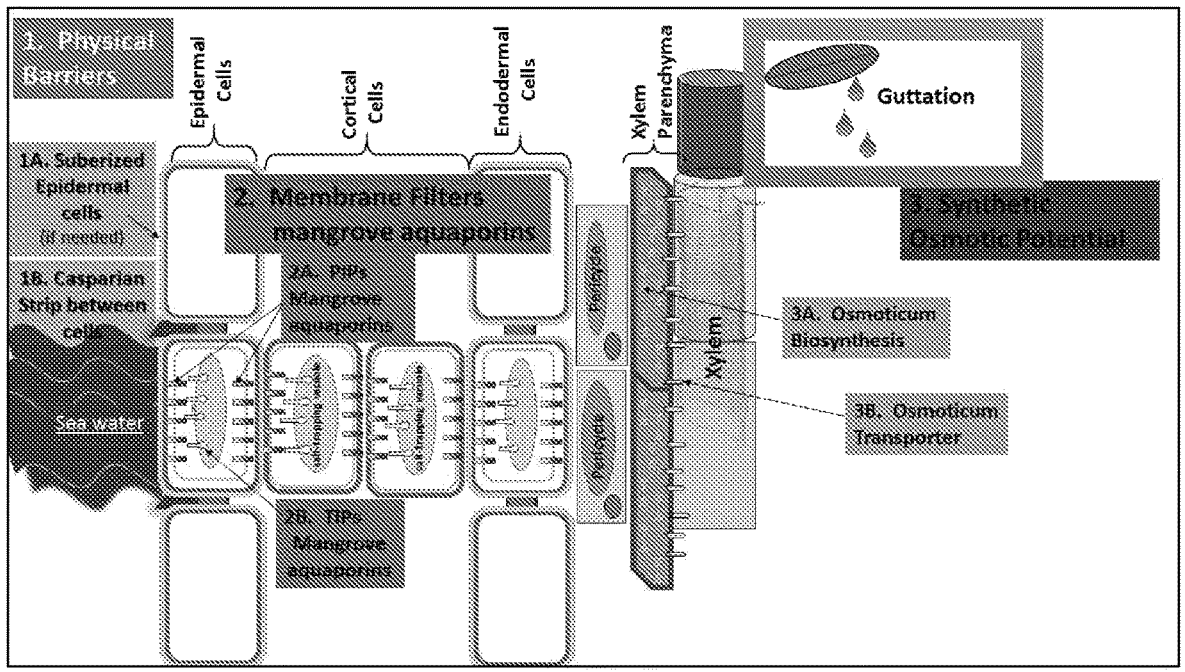
FIG. 1: Schematic of Synthetic Biological Desalination system. 1. Physical barriers are targeted to epidermal cells and enhanced in the endodermal cells. Suberin production (1A) provides a barrier in both epidermal (and other plant cells located toward the exterior side, such as exodermis and periderm) and endodermal cells while the Casparian strip (1B) provides a barrier between cells. 2. Membrane filters or biological water pumps and salt pumping traps are produced from two types of mangrove aquaporins, PIPs (2A, at membrane surface) and TIPs (2B, at the vacuole membrane to direct vacuolar accumulation of any salt that leaks through the physical barriers). 3. Synthetic osmotic potential is provided by mannitol biosynthesis gene (osmoticum biosynthesis; 3A) and mannitol transporter (osmoticum transporter; 3B) in specific cells, the xylem parenchyma. Because the apoplast (plant cell wall) of the xylem parenchyma is contiguous with the xylem transport cells (tracheary elements) the mannitol transporter moves sugars to the xylem transport cells producing a synthetic osmotic gradient.

The inventors separately designed, assembled and tested three complex components needed to encode a synthetic desalination circuit in plants. First, studies were performed to prove that each of these components was functional. After the three components were shown to be functional, they were assembled to produce a complete desalination gene circuit. Plants containing the complete desalination gene circuit survive in salt water with salinity levels greater than that of the ocean (600 mM NaCl) and secrete (via an engineered guttation) water with ionic composition comparable to that of bottled water. FIG. 1 shows a schematic of a synthetic system with the three components engineered to produce a synthetic desalination gene circuit.

Component #1: Genetically Encoded Physical or Structural (Moon, et al., Austr. J. Plant Physiol. 13:637-648, 1986) Barriers. Early work on how mangroves desalinate seawater suggested that a non-metabolic "ultra-filter" is involved (Scholander, 1968, supra). The presently described embodiment of the synthetic desalination gene circuit targets the biosynthesis of two biological structures to the epidermal cells of plant roots, where they form a physical barrier and ultra-filter for the penetration of salt. While the present example describes targeting expression to epidermal cells, those of skill in the art will recognize that expression can be targeted to any cell type toward the exterior of the root, including those that could be recognized as exodermis, periderm (such as the phellem (cork), phellogen (cork cambium) and phelloderm), rhytidome, or some types of bark. Regulatory genes direct production of two non-metabolic components: suberin, a water proofing and filtering component, and the Casparian Strip, a component forming a three-dimensional matrix that effectively plugs gaps between cells, somewhat analogous to tight junctions in mammalian cells (Geldner, Ann. Rev. Plant Biol. 64:531-558, 2013).

Root epidermal targeting components were developed by analysis and production of root epidermal promoters. While the bioinformatics and other literature (Moreno-Risueno, et al., Science 350:426-430, 2015) describes the existence of transcriptional promoters as "root epidermal specific," in planta analysis of nine natural promoters in plant roots showed that this characterization was not always accurate (Table 2).

TABLE 2

| Name | Gene id | Description | Analysis Status | Results |
| --- | --- | --- | --- | --- |
| ABCtrans | At3g53480 | ABC transporter | 162 independent transgenic plants from 7 lines screened; 95 plants from 6 lines promising enough to transfer to soil | Expresses primarily in root epidermis and xylem |
| AMT1; 5 | At3g24290 | Ammonium transporter | 20 independent transgenic plants screened | Non-specific root tissue expression |
| CLE14 | At1g63245 | CLAVATA3/ESR-RELATED 14 | 14 independent transgenic plants screened | Expresses primarily in root epidermis and xylem |
| DUF1 | At2g17070 | Natural epidermal promoter ("Domain of Unknown Function") | 20 independent transgenic plants screened | Non-specific root tissue expression |
| DUF2 | At2g17080 | Natural epidermal promoter ("Domain of Unknown Function") | 20 independent transgenic plants screened | Non-specific root tissue expression |
| IRT2 | At4g19680 | Iron regulated transporter 2 | 3 independent transgenic plants screened | Appears to express in root epidermis and xylem but more screens required |
| KC1 | At4g32650 | K+ rectifying channel 1; At potassium channel 1 | 3 independent transgenic plants screened | Non-specific root tissue expression |
| PGP4 | At2g47000 | P-glycoprotein 4; ATP-binding cassette B4 | 4 independent transgenic plants screened | Non-specific root tissue expression |
| WER | At5g14750 | WEREWOLF; MYB66 | has not been screened | N/A |

It was found that three root transcriptional promoters (ABCtrans (SEQ ID NO:27), CLE14 and IRT2) have strong preference for the root epidermis in some transgenic lines. In addition, two variants (4-block and 7-block; Table 3) of an initial synthetic promoter for the root epidermis (SynEpiProm Ver. 1.0) and an improved root synthetic epidermal promoter (SynEpiProm Ver. 2.0) were designed, assembled and tested. The 4-block (SEQ ID NO:32) and 7-block (SEQ ID NO:33) synthetic promoters express primarily in the root epidermis and xylem. Based on this analysis, the ABC transporter root epidermal promoter (SEQ ID NO:27) was initially chosen to direct expression of the synthetic suberin component and the synthetic Casparian Strip to the root epidermis.

TABLE 3

| Name | Gene id | Description | Analysis Status | Results |
| --- | --- | --- | --- | --- |
| SynEpiProm 1.0 4-block | synthetic | Synthetic promoter based on DUF1 and DUF2 | 21 independent transgenic plants screened | Expresses primarily in root epidermis and xylem |
| SynEpiProm 1.0 7-block | synthetic | Synthetic promoter based on DUF1 and DUF2 | 16 independent transgenic plants screened | Expresses primarily in root epidermis and xylem |

The Casparian Strip produces a three-dimensional matrix containing lignin, a plastic-like molecule that functions much like tight junctions in mammalian cells, effectively forming an impermeable barrier to fluid (i.e., plugging any gaps between cells) (Geldner, Curr. Biol. 23:R1025-1026, 2013). Expression of the Casparian Strip is controlled by the MYB36 transcription factor (Kamiya, et al., Proc. Natl. Acad. Sci. USA 112:10533-10538, 2015). The Casparian Strip is normally found in a specialized cell group in plant roots, the endodermis, a cylindrical-like group of cells that surrounds the vascular system. To direct formation of this three-dimensional matrix to the epidermis, the ABC transporter promoter was used in the presence or absence of a translational enhancer, the 5'-leader sequence (omega) of tobacco mosaic virus (TMV).

Figure 2:
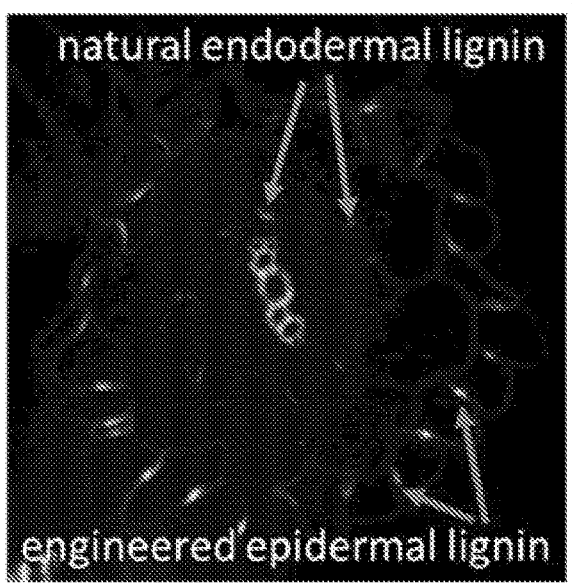
FIG. 2A and FIG. 2B: Evidence of epidermal Casparian strip in transgenic plants. Left panels, fluorescence microscopy image. Right panels, brightfield image overlaid with fluorescence microscopy image. Cross-sections were stained with berberine hemisulfate (a lignin stain) and aniline blue (to quench autofluorescence from root cells) and viewed on a confocal microscope.
Figure 2:
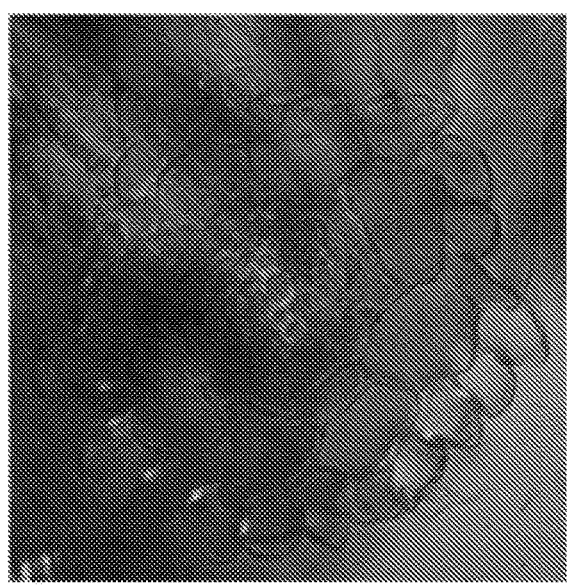
Figure 2:
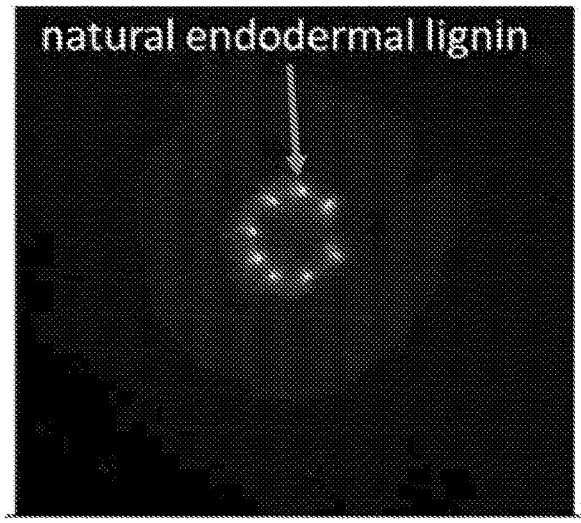
Figure 2:
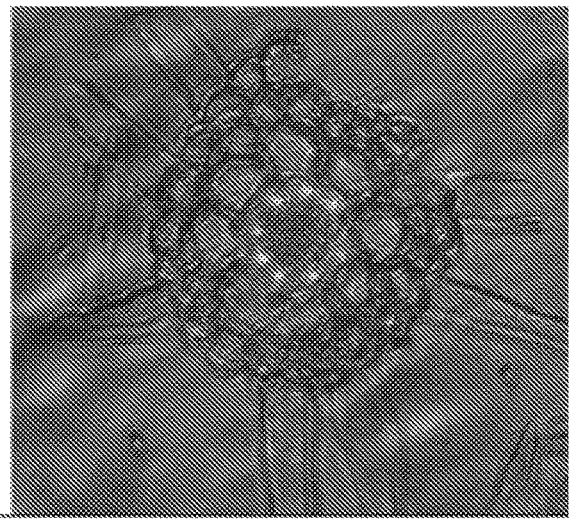

Root cross-sections from T1 plant TKK649-8-14, expressing the MYB36 gene (SEQ ID NO:10) under control of the epidermal ABC transporter promoter (SEQ ID NO:27), and the omega enhancer to enhance translation, were stained with berberine hemisulfate (a lignin stain) and aniline blue (to quench autofluorescence from root cells) (FIG. 2A). Lignin is the main component of the Casparian Strip. Fluorescence images showed staining of lignin in the epidermis (engineered expression), endodermis and vasculature (naturally occurring). Root cross-sections from plant line KJM322, containing the pCASP promoter driving a CASP1_GFP marker gene was studied for verification of membrane localization of the Casparian Strip, which is only found naturally in the endodermis (FIG. 2B).

Results showed that the ABC transporter promoter with the translational enhancer effectively directed expression of a synthetic Casparian Strip to the root epidermis. It is notable that some plant species with salt tolerance have a natural duplication of the Casparian Strip in the epidermis and epidermal-like cells (periderm) (Meyer, et al., J. Exp. Bot. 62:1911-1926, 2011).

Suberin is a lipid-phenolic biopolyester forming a protective barrier in the root endodermis and other parts of the plant. In brief, suberin is a type of somewhat water-proofing material made of complex hydrophobic molecules secreted by the plant outside the plasma membrane and inside the plant cell wall. Suberin varies between different plant stages, plant tissues and plant species (Vishwanath, et al., Plant Cell. Rep. 34:573-586, 2015). Suberin forms a series of layers or lamellae that function to inhibit entry of sodium chloride and other ions. Nature has been one of the best engineers in doing this, as water molecules, with a radius of 137 picometers (pm) (Zhang and Xu, Am. Mineral. 80:670-675, 1995), can move through the layers of suberin, while sodium ions solvated with water have a molecular radius of approximately 358 pm and are unable to move through the layers of suberin (Volkov, et al., Bioelectrochem. Bioenerg. 42:153-160, 1997). The synthetic suberin blocks movement of NaCl, but allows movement of molecules such as water. Expression of suberin can be controlled by expression of the MYB41 gene. Ectopic expression of the MYB41 genes in leaves induced production of suberin-like lamellae with a striking resemblance to lamellae normally found in the cell walls of suberized peridermal and endodermal cells from mature and young roots, respectively (Kosma, et al., Plant J. 80:216-229, 2014). However, the MYB41 promoter is not normally expressed in root epidermal cells (Brady, et al., Science 318:801-806, 2007); in addition, ectopic expression of the MYB41 gene in roots did not lead to enhanced production of suberin, with suberin only found in its natural location, in the endodermis.

Initially, MYB41 was the only factor shown to control the synthesis and deposition of suberin. Subsequently, there have been reports of other Arabidopsis MYB transcription factors besides MYB41 activating suberin biosynthesis. MYB107 and MYB9 homologs were identified as regulators of suberin in angiosperms (Lashbrooke, et al., Plant Cell 28:2097-2116, 2016) and MYB107 has been shown to control biosynthesis of suberin in the seed coat (Gou, et al., Plant Physiol. 173:1045-1058, 2017). A clade of MYB factors potentially involved in suberin formation has been identified that contains 15 Arabidopsis MYBs, including MYB41 (Lashbrooke, et al., 2016, supra). It is likely there is functional redundancy within this clade of Arabidopsis MYB factors, allowing spatial/temporal control of suberin biosynthesis by different MYB factors, induced by various developmental or environmental signals. As such, although the present example describes the use of MYB41, any of these other MYB factors are also contemplated for use in the present disclosure.

The MYB41 protein is known to be activated by phosphorylation through the mitogen activated protein kinase (MAPK) signaling pathway, a complex pathway involved in plant development and stress response (My, et al., Biochem. Biophys. Res. Commun. 422:181-186, 2012).

Two potential reasons were investigated as to why expressing MYB41 in root tissues (other than the endodermis) does not result in enhanced suberin synthesis. First, it is possible the root tissues other than the endodermis do not express the specific MAPKs that phosphorylate and activate MYB41. Second, it is possible that the perception of the stress hormone abscisic acid (ABA) and/or environmental stress is not strong enough in the root epidermis to activate MYB41. This was investigated in transgenic Arabidopsis roots containing the construct TKK644-1, a T-DNA with the ABC transporter promoter (SEQ ID NO:27) driving expression of the MYB41 gene. Transgenic roots were exposed to 10 mM ABA. The results provided evidence that suberin is not produced in response to the stress hormone ABA in Arabidopsis roots. Because the Arabidopsis roots were completely submerged in ABA, these data show that the MAPK responsible for phosphorylating and activating MYB41 is not active in the root epidermis.

Figure 3:
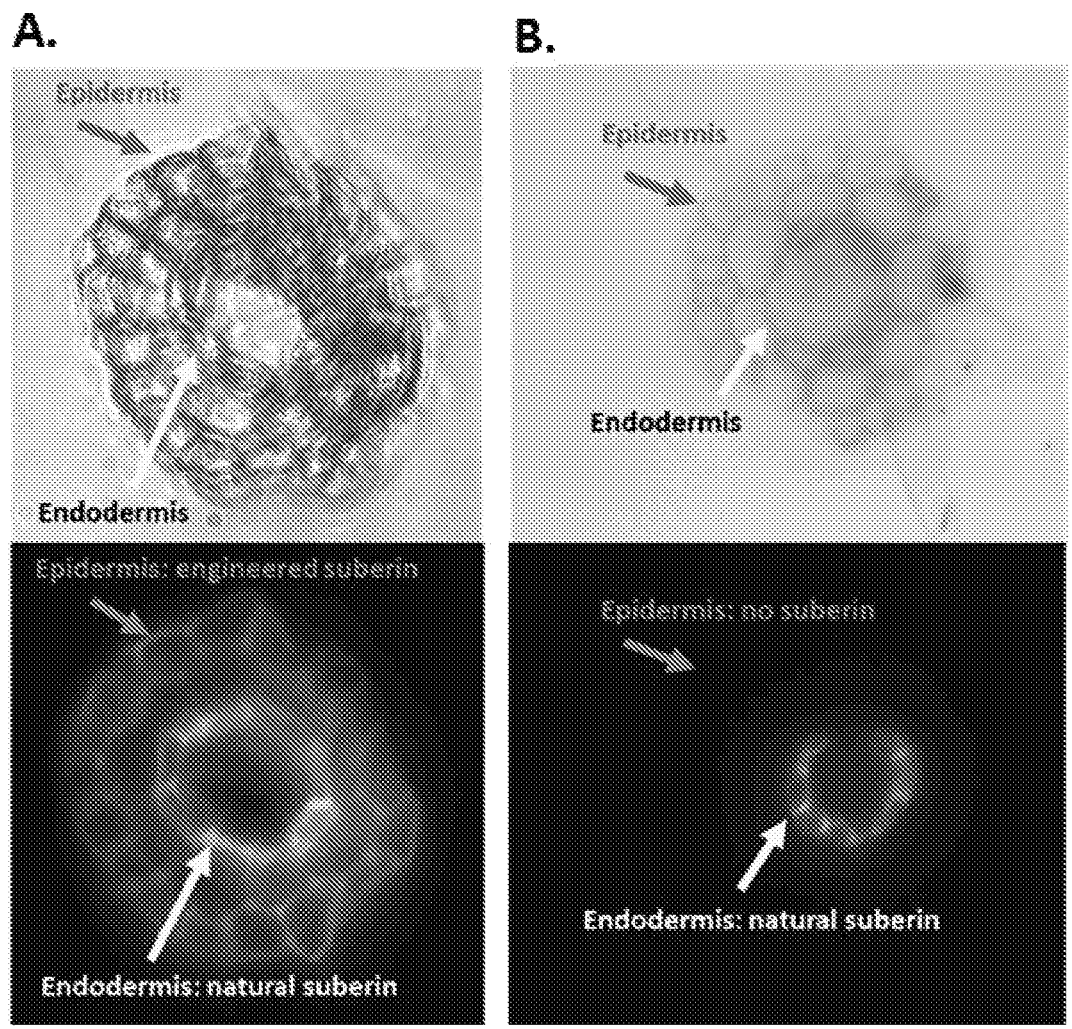
FIG. 3A and FIG. 3B: Evidence of epidermal suberin in root cross sections stained with fluorol yellow. Top panels: brightfield images. Bottom panels: fluorescence microscopy images.

The MYB41 protein is phosphorylated by MAPKs on serine 251. In some proteins mutating a serine residue to an aspartate residue mimics the structure of phospho-serine because of the structural similarity. To demonstrate that this would work for MYB41 in roots, a MYB41 gene was engineered to encode a MYB protein with an aspartate at residue 251 (MYB41 phospho-mimic; SEQ ID NO:13), which was then expressed in transgenic *Arabidopsis* plants under control of an ABC transporter promoter (SEQ ID NO:27). A root cross-section of an *Arabidopsis* plant transformed with the MYB41 phospho-mimic (plant line KJM325-3) under control of the ABC transporter epidermal promoter stained with fluorol yellow, which stains suberin, showed that both the naturally occurring endodermal suberin and the engineered epidermal suberin were visible (FIG. 3A). A root cross-section of wild-type *Arabidopsis*, stained with fluorol yellow, showed only the natural endodermal suberin (FIG. 3B). These results show that expression of MYB41 phospho-mimic with the ABC transporter promoter directed production of suberin in the *Arabidopsis* root epidermis.

Collectively, these three accomplishments allowed targeted expression of suberin and a synthetic Casparian Strip to the cells at the exterior of the root, the root epidermis. The synthetic Casparian Strip forms a water-tight junction that prevents salt water from penetrating between the root epidermal cells that contact the environment. Suberin forms a $Na^+$ filtering and partial water-proofing barrier in root epidermal cells. Hence, the first component is designed to filter salt, reduce detrimental effects of salt water exposure, and prevent water, salt water, or seawater or otherwise contaminated water from entering a plant between root epidermal cells. Thus, the suberin expressed in the root epidermis and the Casparian Strip "plugging" gaps between cells likely constitute the non-metabolic ultra-filter previously proposed (Scholander, 1968, supra).

Component #2: Genetically Encoded Water Transporting and Salt Collection System. While a non-metabolic filter was originally proposed to filter or desalinate seawater, later reports suggested the plant's membrane system (symplast) also plays a role in this process (Moon, et al., 1986, supra). To produce a synthetic water transport/salt collection system in plants, the present disclosure uses aquaporins, specialized proteins that transport water and sequester salt ions in vacuoles. Aquaporin genes from mangroves, were genetically encoded and expression was directed to cells in the root. Mangroves must be efficient at this process to survive continual flooding by the ocean and the hypersaline environments that build up in coastal areas, hence, genetic information available for mangrove aquaporins was used. Because complete genome information for any species of mangroves is still lacking, incomplete information for mangrove aquaporins was filled-in with genetic information for aquaporins from halophytes (salt loving plants; e.g., when lacking complete information from mangroves, halophyte sequences were used to complete the 5' codon region). In developing the synthetic desalination circuit, a variety of aquaporin genes were first assembled and tested in planta.

Then expression of two types of synthetic mangrove aquaporins was directed in cells throughout the root using a promoter (KCl) that was confirmed to be properly expressed throughout root cells. This provided a continuous symplastic pathway for water to move radially from the outer portion of the root to the vasculature, as well as increase the presence of salt-sequestering mangrove aquaporins, to target any NaCl that might enter the root, to the vacuole for safe exclusion of the salt.

Component 2A is reprogrammed mangrove aquaporins, specifically, PIPs (plasma membrane intrinsic proteins), that enable the desalination plants to transport water (not seawater) through the symplastic system of root cells. Data suggests that two PIPs are needed for correct function. Mangrove aquaporins were engineered and tested with drought and salt stress assays. The PIPs with the most promising function were AoPIP 1.2, derived from the mangrove species *Avicennia officinalis*, and BgPIP2, derived from the mangrove species *Bruguiera gymnorrhiza*. These mangrove aquaporins were targeted to the plasma membrane. Below, results are presented first for PIPs (drought and salt tolerance assays to verify function) and then for TIPs (tonoplast intrinsic membrane proteins), which is Component 2B (drought and salt tolerance assays to verify function).

Drought stress tolerance was studied in a transgenic *Arabidopsis* line where the mangrove aquaporin AoPIP1.2 (SEQ ID NO:1) was expressed in the epidermis using the ABC transporter promoter (SEQ ID NO:27). Plant line TKK630 (pABCtrans_AoPIP1.2) and wild-type plants were either watered regularly for 10 days or not watered (drought treatment) for 10 days. Some but not all drought-treated transgenic plants were more viable than the wild-type. The same drought-stressed plants were watered after the end of the 10 day drought treatment. Five of the seven transgenic lines recovered, while none of the wild-type plants recovered.

Drought stress tolerance was also studied in a transgenic *Arabidopsis* line where mangrove aquaporin AoPIP1.2 (SEQ ID NO:1) was expressed in the endodermis. Plant line TKK589 (pSCR_AoPIP1.2) and wild-type plants were either watered regularly for 11 days or not watered for 11 days (drought stress treatment). The transgenic plants tested under drought conditions remained viable after 11 days of no water. The drought-stressed transgenic lines were then watered after the end of the drought treatment; all of the transgenic lines recovered.

Drought stress tolerance was additionally studied in *Arabidopsis* plants expressing the mangrove aquaporin gene BgPIP2 (SEQ ID NO:3) using the ABC transporter promoter (SEQ ID NO:27). Plants from line TKK632 (ABCtrans_BgPIP2, an epidermal promoter driving a mangrove aquaporin) or wild-type plants were either watered regularly for 10 days or not watered for 10 days. After 10 days without water, the wild-type plants showed severe drought stress, while the TKK632 plants were still viable. This showed that the TKK632 plants were more tolerant to drought than the wild-type plants.

Table 4 summarizes the results of the drought tolerance assays in *Arabidopsis* plants with PIP genes.

TABLE 4

| Aquaporin | Results with epidermal (ABCtrans) promoter | Results with endodermal (SCR2.5k) promoter |
|---|---|---|
| AoPIP1.2 | Improved drought tolerance (line TKK630) | Improved drought tolerance (line TKK589) |
| BgPIP2 | Improved drought tolerance (TKK632) | Improved drought tolerance (line TKK591) |

FIG. 4 shows the results of salt stress tolerance in T1 lines of TKK630, which has the mangrove PIP AoPIP1.2 expressed in the epidermis with the pABC transporter promoter. A root bending assay was used to provide quantitative data on plant response to salt stress. Sterilized seeds were plated on MS solid media, vernalized for 3 days at 4° C. and grown in a growth chamber under normal growth conditions. Five day old wild-type and transgenic seedlings were transferred to plates with fresh MS media with or without 100 mM NaCl and grown vertically with the seedlings inverted. After five to six days, root length was measured for plants in MS (left panel), and in MS plus 100 mM NaCl (right panel). Of the seven transgenic lines assayed, TKK630-6 (asterisk) showed significantly improved salt tolerance relative to the wild-type plants.

FIG. 5 shows the results of salt stress tolerance in T1 lines of TKK591, which has the mangrove PIP BgPIP2 expressed in the endodermis with the SCARECROW (SCR) promoter. The root bending assay described above was used, and root length was measured in MS (left panel), and in MS plus 100 mM NaCl (right panel). Of the eight transgenic lines assayed, TKK591-9 (asterisk) showed significantly improved salt tolerance relative to the wild-type plants.

Table 5 summarizes the results of the salt tolerance assays in *Arabidopsis* plants with PIP genes.

TABLE 5

| Aquaporin | Results with epidermal (ABCtrans) promoter | Results with endodermal (SCR2.5k) promoter |
| --- | --- | --- |
| AoPIP1.2 | One T1 line showed improved salt tolerance (line TKK630) | No improvement over wild-type (TKK589) |
| BgPIP2 | No improvement over wild-type (TKK632) | One T1 line showed improved salt tolerance (TKK591) |

Component 2B is additional aquaporins, specifically, TIPs (Tonoplast intrinsic membrane proteins). While it was fully anticipated that mangrove TIPs would function, genomic information was lacking for these, and also the TIPs from *Kandelia candel* and *Bruguiera gymnorrhiza* did not show tissue specific expression with a C-terminal GFP fusion. Thus, characterized TIPs from a halophytic species, *Eutrema salsuginea* (salt cress) were used. As with the PIPs, the separate TIPs components were first assembled and tested for function in planta. The most promising TIPs were TsTIP 1.1 (SEQ ID NO:9) and TsTIP 1.2 (SEQ ID NO:6), both derived from *Eutrema salsugineum* (salt cress). Of these two, TsTIP1.2 resulted in more tolerant plants during salt and drought stress assays (see below).

Drought stress experiments were performed to test drought tolerance in *Arabidopsis* plants expressing a salt cress aquaporin gene. Plants from line TKK668 (pABCtrans_Ts TIP1.1, an epidermal promoter driving a salt cress aquaporin), line TKK669 (pABCtrans_TsTIP1.2, an epidermal promoter driving a salt cress aquaporin), and wild-type *Arabidopsis* controls were either watered daily for 10 days or not watered for 10 days. Then the drought-stressed plants were watered once at the end of 10 days and allowed to recover for one day. Most drought-stressed transgenic plants recovered viability after re-watering, in contrast to the wild-type plants, which were unable to recover.

Table 6 summarizes the results of the drought tolerance assays in *Arabidopsis* plants with TIP genes.

TABLE 6

| Aquaporin | Results with epidermal (ABCtrans) promoter | Results with endodermal (SCR2.5k) promoter |
| --- | --- | --- |
| TsTIP1.1 | Improved drought tolerance (line TKK668) | Improved drought tolerance (line TKK617) |
| TsTIP1.2 | Improved drought tolerance (line TKK669) | Improved drought tolerance (line TKK618) |

Studies were performed to test salt tolerance in transgenic *Arabidopsis* plants expressing a salt cress aquaporin gene. Plants from line TKK669 (pABCtrans_TsTIP1.2, an epidermal promoter driving a salt cress aquaporin) and wild-type *Arabidopsis* controls were either watered daily with tap water for 12 days or watered with 350 mM NaCl for 12 days. All but one salt-stressed transgenic plant, and no wild-type plants, showed continued growth in the presence of salt and 16 plants bolted, with seven plants setting seed.

Table 7 summarizes the results of the salt tolerance assays in *Arabidopsis* plants with TIP genes. Aquaporins AoPIP1.2, BgPIP2, and TsTIP1.2 were selected for use with the complete desalination circuit in the present Example.

TABLE 7

| Aquaporin | Results with epidermal (ABCtrans) promoter | Results with endodermal (SCR2.5k) promoter |
| --- | --- | --- |
| TsTIP1.1 | No improvement over wild-type (line TKK668) | No improvement over wild-type (line TKK617) |
| TsTIP1.2 | Most plants showed improved salt tolerance (line TKK669) | No improvement over wild-type (TKK618) |

Component #3: Retain Pure Water and Pump Water to Leaves for Collection. Because plants filtering water would still be surrounded by the salt water (or otherwise contaminated water), simple osmosis could drive the purified water out of the roots. To overcome this, a mechanism was engineered to allow the desalination plants to retain and pump (secrete) the purified water. A type of water secretion by plants known as guttation was used.

Mangroves maintain a high osmotic potential within their vascular tissue, which is thought to prevent the sea from recovering the filtered water by simple osmosis and allows water to be transported to the shoot and leaves. The presently described synthetic osmotic gradient in the vascular tissue involves two steps: first, targeting mannitol biosynthesis genes to vascular tissue cells capable of biosynthesizing a sugar (xylem parenchyma cells); and second, targeting a mannitol transporter to the apoplast of the xylem parenchyma cells. Because the xylem parenchyma apoplast is contiguous with the apoplast of the water transport cells (vessel elements, tracheary elements), mannitol synthesized in the xylem parenchyma will be transported to the xylem elements. The higher amount of mannitol in the vasculature drives the flow of water into the vasculature.

As before, expression of the transcriptional promoters was checked and verified to direct expression of the components. Multiple putative xylem and xylem parenchyma specific promoters were checked (Table 8), and initial efforts were focused on the XCP1 (SEQ ID NO:31) and CESA7 (SEQ ID NO:29) promoters.

TABLE 8

| Name | Gene ID | Description | Analysis Status | Results |
|---|---|---|---|---|
| CESA7 (SEQ ID NO: 29) | At5g17420 | Cellulose synthase catalytic subunit 7 | 11 independent transgenic plants screened | Xylem localization found in 4 or more plants |
| VND7 (SEQ ID NO: 30) | At1g71930 | Vascular-related NAC-domain protein 7 | 25 independent transgenic plants analyzed | Expression confirmed in whole root screens |
| XCP1 (SEQ ID NO: 31) | At4g35350 | Xylem cysteine peptidase 1 | 10 independent transgenic plants screened | Xylem localization found in 4 or more plants |

Component 3A is a mannitol biosynthesis gene (mannose-6-phosphate-reductase, M6PR; SEQ ID NO:19) under control of a xylem parenchyma-specific promoter (XCP1), which directs production of this specialized sugar to the xylem parenchyma. This gene causes the localized overproduction of sugar in a cytoplasmic cell in the vascular tissue (xylem parenchyma), sometimes called vessel associated cells (VACs).

Component 3B is a mannitol transporter gene (MTR; SEQ ID NO:16) under control of the xylem parenchyma specific CESA7 promoter. Expression of this gene is also targeted to the xylem parenchyma or VACs, but in such a way that it will pump mannitol to the apoplast (cell wall). Because the xylem parenchyma's apoplast is contiguous with the xylem's apoplast, mannitol will enter the xylem (dead cells). When plants pump an osmoticum such as mannitol into the apoplast, water follows to substantially increase osmotic pressure of the xylem. This prevents water purified by the plant from diffusing back out of the plant by osmosis.

FIG. 6 shows functional analysis of the water secretion component in independent transgenic plant lines. When treated with tap water, the transgenic lines with the water secretion component secrete (guttate) a greater volume of water, demonstrating functionality.

Once components 1, 2 and 3 described above were assembled, tested and functionally verified, all three components were assembled into a complete desalination genetic circuit. One version was assembled in which the complete circuit was contained in two plasmids for plant transformation (FIG. 7A and FIG. 7B) and a second version in which the complete circuit was contained in one plasmid (FIG. 8). Plants containing the synthetic desalination circuit survived and set seed even when watered with 600 mM NaCl (note seawater is approximately 550 mM NaCl with some other salts).

Table 9 shows analysis of water samples and plant-secreted water obtained from plants that were watered with tap water or 600 mM NaCl. When the water source for watering the plants was tap water, both control and transgenic plant secreted (guttated) water of high purity. In contrast, when the water source for watering the plants was 600 mM NaCl, control plants did not secrete any water, whereas the synthetic desalination plants secreted water with a salinity content comparable to that of bottled water. The control plants also showed the appearance of a purple-red color, indicating the control plants were highly stressed. The control plants typically died soon after salt water treatment.

TABLE 9

Plant Desalination: Data on plant secreted water and various samples

| | Water Samples | Conductivity (mS/cm) | Salt (%) | Total Dissolved Solids (ppm) |
|---|---|---|---|---|
| Measurement & Data with Various Water Samples | DI water | 0.03 | 0 | 2 |
| | Tap water | 0.127 | 0.01 | 68 |
| | Bottled Water | 0.1-0.3 | ~0.03 (varies by source) | 31-41 |
| | Seawater (~550 mM NaCl) | 50 | 3.5 | 35000 |

| | PLANTS | Conductivity (mS/cm) | Salt (%) | Total Dissolved Solids (ppm) |
|---|---|---|---|---|
| | | | Source: Top water | |
| Measurement of water secreted by plants | Control plants average ± Std | 0.267 ± 0.120 | 0.013 ± 0.008 | 142 ± 66 |
| | Tronsgenics average ± Std | 0.418 ± 0.192 | 0.023 ± 0.011 | 226 ± 104 |
| | | | Source: 600 mM NaCl | |
| | Control Plants | | Did not secrete any water | |
| | Desalination Plant TKK716-85 | 0.49 | 0.03 | 260 |
| | Desalination Plant TKK716-124 | 0.47 | 0.04 | 360 |

All measurements to date with a conductivity meter (Laqua twin, Horiba Scientific).

Collectively these data provide definitive evidence that plants genetically modified with the presently described synthetic desalination circuit can filter salt water and secrete (guttate) pure water. This photosynthetically powered desalination system can be used to purify salt water, seawater and also various types of contaminated water. This phytodesalination process provides a pathway toward sustainable human life on earth, and provides a means to grow crops and other plants under saline conditions.

The term "about" is used herein to indicate that a value includes the standard deviation of error for the device or method being employed to determine the value. The use of the term "or" in the claims is used to mean "and/or" unless explicitly indicated to refer to alternatives only or the alternatives are mutually exclusive, although the disclosure supports a definition that refers to only alternatives and to "and/or." When not used in conjunction closed wording in the claims or specifically noted otherwise, the words "a" and "an" denote "one or more."

The terms "comprise," "have," and "include" are open-ended linking verbs. Any forms or tenses of one or more of these verbs, such as "comprises," "comprising," "has," "having," "includes," and "including," are also open-ended. For example, any method that "comprises," "has" or "includes" one or more steps is not limited to possessing only those one or more steps and also covers other unlisted steps. Similarly, any cell that "comprises," "has" or "includes" one or more traits is not limited to possessing only those one or more traits and covers other unlisted traits.

While the disclosure has been described in connection with specific embodiments thereof, it will be understood that the present disclosure is capable of further modifications by one of skill in the art. It is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible. The present disclosure is therefore intended to encompass any variations, uses, or adaptations of the invention following, in general, the principles of the invention and including such departures from the present disclosure as come within known or customary practice within the art to which the invention pertains and as may be applied to the essential features herein before set forth.

All of the compositions and/or methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

All publications, patents, patent publications, and nucleic acid and amino acid sequences cited are incorporated by reference herein in their entirety for all purposes.

What is claimed is:

1. A transgenic plant genetically engineered to produce purified water, comprising:
   a) a MYB41 polypeptide comprising at least 95% amino acid sequence identity to the amino acid sequence encoded by the nucleotide sequence as set forth in SEQ ID NO: 13, wherein expression of said MYB41 polypeptide results in the biosynthesis of a genetically encoded physical barrier component suberin in said transgenic plant, and a MYB36 polypeptide sequence comprising at least 95% amino acid sequence identity to the amino acid sequence encoded by the nucleotide sequence as set forth in SEQ ID NO: 10, wherein expression of said MYB36 polypeptide results in the biosynthesis of a genetically encoded physical barrier component Casparian Strip in said transgenic plant, and wherein said suberin and said Casparian Strip are produced in the root epidermis of said transgenic plant;
   b) genetically encoded water filtering and transport components comprising an aquaporin polypeptide comprising at least 95% amino acid sequence identity to the amino acid sequence encoded by the nucleotide sequence as set forth in SEQ ID NO: 1, and wherein the aquaporin polypeptide is expressed in the root epidermis from a heterologous promoter operably linked to said nucleotide sequence of part b); and
   c) genetically encoded water retention and pumping components comprising a mannitol biosynthesis polypeptide comprising at least 95% amino acid sequence identity to the amino acid sequence encoded by the nucleotide sequence as set forth in SEQ ID NO: 19, and a mannitol transport polypeptide comprising at least 95% amino acid sequence identity to the amino acid sequence encoded by the nucleotide sequence as set forth in SEQ ID NO: 16, and wherein said mannitol biosynthesis polypeptide and said mannitol transporter polypeptide are expressed in the xylem parenchyma from a heterologous promoter operably linked to each of said nucleotide sequences of part c), wherein said transgenic plant, produces purified water when grown in water containing an impurity.

2. The transgenic plant of claim 1, wherein:
   a) the transgenic plant is a monocot plant;
   b) the transgenic plant is a rice, wheat, barley, oats, rye, sorghum or maize plant;
   c) the transgenic plant is a rice plant;
   d) the transgenic plant is a dicot plant; or
   e) the transgenic plant is a soybean, alfalfa, sunflower, cotton, canola, sugar beet, sweet potato, tomato, strawberry, tobacco, banana, grape, cucurbits, pepper, beach plum, wax myrtle, mesquite, salt cedar, crossvine, withe vine, acacia, or laurel fig plant.

3. The transgenic plant of claim 1, wherein said transgenic plant produces purified water when grown in salt or sea water.

4. A transgenic plant part from the transgenic plant of claim 1, and wherein the transgenic plant part comprises said transgenic polypeptides and said components of parts a), b) and c).

5. The transgenic plant part of claim 4, wherein the transgenic plant part is a cell, meristem, root, leaf, node, pistil, anther, flower, seed, embryo, stalk or petiole.

6. A method of producing purified water from salt or sea water, comprising growing the transgenic plant of claim 1 in salt of sea water and collecting the purified water produced by the transgenic plant.

* * * * *